(12) United States Patent
Bremond et al.

(10) Patent No.: US 10,301,655 B2
(45) Date of Patent: May 28, 2019

(54) METHOD FOR PRODUCING ACETOIN

(71) Applicant: ALDERYS, Orsay (FR)

(72) Inventors: Mélanie Bremond, Le Plessis Robinson (FR); Karine Jaillardon, St Michel sur Orge (FR); Dominique Louis, Forges les Bains (FR); Dominique Thomas, Gif sur Yvette (FR)

(73) Assignee: ALDERYS, Orsay (FR)

( * ) Notice: Subject to any disclaimer, the term of this patent is extended or adjusted under 35 U.S.C. 154(b) by 338 days.

(21) Appl. No.: 15/327,207

(22) PCT Filed: Jul. 23, 2015

(86) PCT No.: PCT/EP2015/066927
§ 371 (c)(1),
(2) Date: Jan. 18, 2017

(87) PCT Pub. No.: WO2016/012561
PCT Pub. Date: Jan. 28, 2016

(65) Prior Publication Data
US 2017/0159081 A1    Jun. 8, 2017

(30) Foreign Application Priority Data

Jul. 25, 2014 (EP) .................... 14306205

(51) Int. Cl.
| | | |
|---|---|---|
| *C12P 7/26* | (2006.01) | |
| *C12N 9/88* | (2006.01) | |
| *C12N 9/02* | (2006.01) | |
| *C12N 9/10* | (2006.01) | |

(52) U.S. Cl.
CPC .............. *C12P 7/26* (2013.01); *C12N 9/0036* (2013.01); *C12N 9/1022* (2013.01); *C12N 9/88* (2013.01); *C12Y 106/03001* (2013.01); *C12Y 202/01006* (2013.01); *C12Y 401/01001* (2013.01); *C12Y 401/01005* (2013.01)

(58) Field of Classification Search
CPC ........... C12P 7/26; C12N 9/88; C12N 9/1022; C12N 9/0036
See application file for complete search history.

(56) References Cited

FOREIGN PATENT DOCUMENTS

| WO | 2011/041426 A1 | 4/2011 |
|---|---|---|
| WO | 2013/076144 A2 | 5/2013 |

OTHER PUBLICATIONS

Bae et al. 2016; Efficient production of acetoin in *Saccharomyces cerevisiae* by disruption of 2,3-butanediol dehydrogenase and expression of NADH oxidase. At www.nature.com/articles/srep27667.pdf.*
Jiazhang Lian et al: "Metabolic engineering of a *Saccharomyces cerevisiae* strain capable of simultaneously utilizing glucose and galactose to produce enantiopure (2R,3R)-butanediol", Metabolic Engineering, vol. 23, pp. 92-99, May 1, 2014.
Shubo Li et al: "Enhancement of acetoin production in *Candida glabrata* by in silico-aided metabolic engineering", Microbial Cell Factories, Biomed Central, London, NL, vol. 13, No. 1, p. 55, Apr. 13, 2014.
Zhikun Wang et al: "Production of pyruvate inthrough adaptive evolution and rational cofactor metabolic engineering", Biochemical Engineering Journal, Elsevier, Amsterdam, NL, vol. 67, pp. 126-131, Jun. 10, 2012.
Heux S et al: "Cofactor engineering in *Saccharomyces cerevisiae*: Expression of a H20-forming NADH oxidase and impact on redox metabolism", Metabolic Engineering, Academic Press, US, vol. 8, No. 4, pp. 303-314, 206-07-01.

* cited by examiner

*Primary Examiner* — Karen Cochrane Carlson
(74) *Attorney, Agent, or Firm* — W & C IP

(57) ABSTRACT

The present invention relates to a recombinant yeast having a reduced pyruvate decarboxylase activity, in the genome of which has been inserted: —one or more nucleic acids encoding an acetolactate synthase or ALS, —one or more nucleic acids en coding an acetolactate decarboxylase or ALD, and—one or more copies of a nucleic acids encoding a NADH oxidase or NOXE.

18 Claims, 1 Drawing Sheet

Specification includes a Sequence Listing.

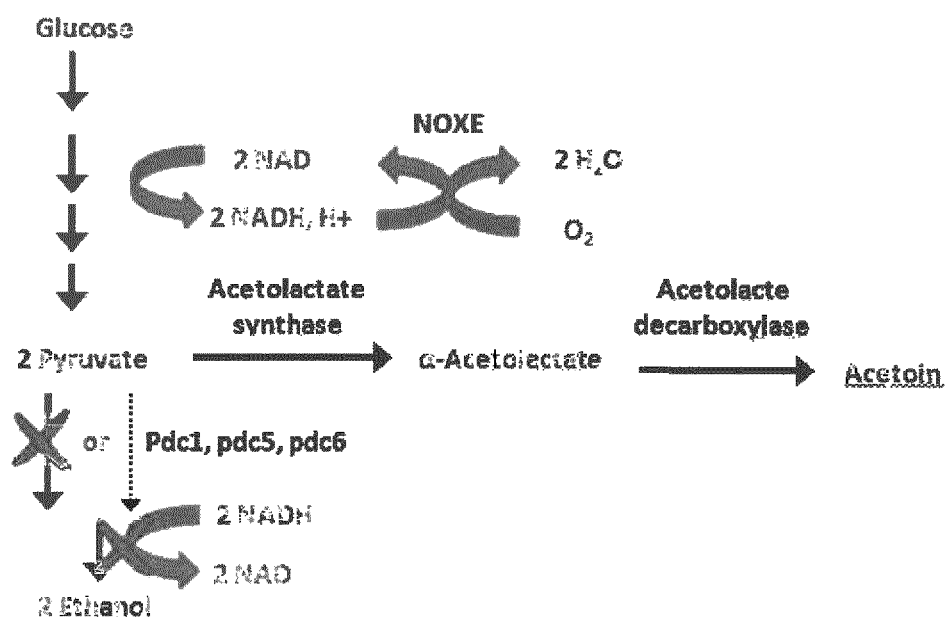

SEQUENCE LISTING

<160> NUMBER OF SEQ ID NOS: 52

<210> SEQ ID NO 1
<211> LENGTH: 1716
<212> TYPE: DNA
<213> ORGANISM: Bacillus subtilis

<400> SEQUENCE: 1

| | | | | | | |
|---|---|---|---|---|---|---|
| atgtctacca | aagcaacaaa | agagcaaaag | agccttgtga | agaatagagg | tgcagaactt | 60 |
| gtcgttgatt | gcttggtaga | acagggagtc | actcacgttt | tcgggatacc | cggcgctaaa | 120 |
| atcgacgccg | tgtttgacgc | tttacaggat | aagggaccag | agatcattgt | tgctagacat | 180 |
| gaacagaatg | cagcgttcat | ggctcaagct | gtaggtagac | ttactgggaa | acccggtgtg | 240 |
| gttttggtta | ctagtggacc | aggtgcatca | aatctagcaa | caggtttgtt | aacagcgaat | 300 |
| acagagggag | atcctgttgt | tgcattagca | ggaaacgtta | tcagagcgga | tagactgaaa | 360 |
| agaacccatc | aatcattgga | taatgctgca | ttatttcagc | caattacgaa | atattccgtc | 420 |
| gaagtacagg | atgtgaagaa | catacctgaa | gctgtaacta | atgcgtttcg | tatagcttct | 480 |
| gctggtcaag | ctggtgcagc | ttttgtttcg | tttccgcaag | acgttgtcaa | cgaggttacg | 540 |
| aacactaaga | atgtgagagc | agtagcagcc | ccaaaattag | gaccagctgc | tgatgatgct | 600 |
| atatcagctg | ctattgctaa | gattcagaca | gccaaactac | ctgttgtctt | agtaggtatg | 660 |
| aaaggtgcag | ggcagaagc | aatcaaggca | gttagaaaac | tgttgaagaa | ggttcaattg | 720 |
| ccgtttgtgg | aaacctatca | agccgcaggg | acttttgtcta | gggatctaga | agatcaatac | 780 |
| ttcggtagaa | tagggttgtt | cagaaatcaa | cctggcgact | tgttactgga | acaagccgat | 840 |
| gtcgtgctta | caattggtta | cgatccgatt | gaatatgacc | ccaaattttg | gaatattaat | 900 |

```
ggtgatagga ctattatcca cttagacgag attattgccg atattgacca tgcttatcaa    960
cctgatctgg aactgatagg tgatattcca agtactatca accatataga gcatgatgcc   1020
gtcaaagtgg aatttgccga agagaacag aagatcctat ccgatctaaa gcagtacatg   1080
catgaaggcg aacaagttcc agcagattgg aaatccgata gagcacatcc attggaaatt   1140
gtcaaagaat tgagaaatgc agttgatgac catgttacag ttacttgtga cataggtagt   1200
cacgctattt ggatgtctag gtacttcaga tcttatgagc cattaacgtt gatgatatcc   1260
aatggcatgc aaacccttgg agtcgcttta ccatgggcca ttggtgcgtc gttagtaaag   1320
ccaggagaga aagtcgtttc tgtgtcaggt gatggtggtt tcttgttctc tgccatggaa   1380
ttggaaaccg ccgttcgttt gaaagcccct atagtacaca tcgtgtggaa tgattcgacc   1440
tatgacatgg tcgcgtttca acaattgaag aagtacaacc gtacttcagc tgttgatttc   1500
ggcaacattg acattgtgaa gtacgcggaa agctttggcg ccacaggcct aagagtcgaa   1560
tcacctgatc aattagcaga tgtacttagg caagggatga acgctgaagg acctgtaatt   1620
atcgacgtac ctgttgacta tagcgacaac atcaatttag ccagtgataa attacccaaa   1680
gagtttggtg agctaatgaa acgaaagct ttgtaa                              1716
```

<210> SEQ ID NO 2
<211> LENGTH: 571
<212> TYPE: PRT
<213> ORGANISM: Bacillus subtilis

<400> SEQUENCE: 2

```
Met Ser Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
```

|     |     |     |     |     |     |     |     |     |     |     |     |     |     |     |
|-----|-----|-----|-----|-----|-----|-----|-----|-----|-----|-----|-----|-----|-----|-----|
| 225 | | | | | 230 | | | | | 235 | | | | 240 |

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 3
<211> LENGTH: 1995
<212> TYPE: DNA
<213> ORGANISM: Nicotiana tabacum

<400> SEQUENCE: 3
atggctgctg ctgcagctgc tccatctcca tcttttttcta aaaccttgtc ctcctcctct    60
tccaaatctt ctactttgtt gccaagatct actttcccat ttccacatca tcccataaag   120
actactccac caccattgca tttgactcca actcatattc actcccaaag aagaagattc   180

```
accatctcca acgttatttc taccacccaa aaggtttctg aaactcaaaa ggctgaaacc    240
ttcgtttcta gatttgctcc agatgaacct agaaagggtt ctgatgtttt ggttgaagct    300
ttggaaagag aaggtgttac cgatgttttt gcttatccag gtggtgcttc tatggaaatt    360
catcaagctt tgaccagatc ctccatcatt agaaatgttt tgccaagaca tgaacaaggt    420
ggtgttttcg ctgctgaagg ttatgctaga gctactggtt ttccaggtgt atgtattgct    480
acttctggtc caggtgctac taatttggtt tctggtttgg ctgatgcttt gttggattct    540
gttccaatcg ttgctattac tggtcaagtt ccaagaagaa tgattggtac agatgctttc    600
caagaaaccc caattgtcga agttactaga tctattacca agcacaacta cttggttatg    660
gacgttgaag atatcccaag agttgttaga gaagcatttt tcttggctag atctggtaga    720
ccaggtccag ttttgattga tgttccaaag gatatccaac aacaattggt tatcccagat    780
tgggaccaac ctatgagatt gccaggttat atgtctagat gccaaagtt gccaaacgaa    840
atgttgttag aacaaatcgt cagattgatc tccgaatcta aaaagccagt cttgtatgtt    900
ggtggtggtt gttctcaatc tagtgaagaa ttgagaagat tcgtcgaatt gaccggtatt    960
ccagttgctt ctacattgat gggtttgggt gcttttccaa ctggtgatga attgtctttg   1020
tctatgttgg gtatgcacgg tactgtttat gctaattacg ctgttgattc ctccgatttg   1080
ttgttagctt ttggtgttag attcgatgat agagtcactg gtaagttgga agcttttgct   1140
tctagagcta agatcgttca tatcgacatt gattccgctg aaatcggtaa aaacaagcaa   1200
ccacatgttt ctatttgcgc cgatattaag ttggcattgc aaggtttgaa cagtatcttg   1260
gaatccaaag aaggtaaatt gaagttggac ttctctgctt ggagacaaga attgacagtt   1320
caaaaggtta agtacccatt gaacttcaag actttcggtg atgctattcc accacaatac   1380
gctattcaag ttttggatga attgaccaac ggttccgcta ttatttcaac tggtgttggt   1440
caacatcaaa tgtgggctgc tcaatattac aagtacagaa aacctagaca atggttgact   1500
tctggtggtt taggtgctat gggttttggt ttgccagctg ctattggtgc tgctgttggt   1560
agacctgatg aagttgttgt agatattgat ggtgacggtt ccttcattat gaacgtccaa   1620
gaattggcta ccatcaaggt tgaaaatttg ccagtcaaga tcatgttatt gaacaatcaa   1680
cacttgggta tggtcgtcca atgggaagat agatttttaca aagctaatag agcccacacc   1740
tacttgggta atccatctaa tgaagctgaa atcttcccaa acatgttgaa gtttgctgaa   1800
gcttgtggtg ttccagctgc aagagttact catagagatg atttgagagc tgccatccaa   1860
aagatgttgg atactccagg tccatacttg ttggatgtta ttgtcccaca tcaagaacat   1920
gtcttgccaa tgattccatc tggtggtgcc tttaaagatg ttattactga aggtgacggt   1980
agatcctctt actga                                                    1995
```

<210> SEQ ID NO 4
<211> LENGTH: 664
<212> TYPE: PRT
<213> ORGANISM: Nicotiana tabacum

<400> SEQUENCE: 4

Met Ala Ala Ala Ala Ala Ala Pro Ser Pro Ser Phe Ser Lys Thr Leu
1               5                   10                  15

Ser Ser Ser Ser Ser Lys Ser Ser Thr Leu Leu Pro Arg Ser Thr Phe
            20                  25                  30

Pro Phe Pro His His Pro His Lys Thr Thr Pro Pro Pro Leu His Leu
        35                  40                  45

```
Thr Pro Thr His Ile His Ser Gln Arg Arg Phe Thr Ile Ser Asn
 50                  55                  60

Val Ile Ser Thr Thr Gln Lys Val Ser Glu Thr Gln Lys Ala Glu Thr
 65                  70                  75                  80

Phe Val Ser Arg Phe Ala Pro Asp Glu Pro Arg Lys Gly Ser Asp Val
                 85                  90                  95

Leu Val Glu Ala Leu Glu Arg Glu Gly Val Thr Asp Val Phe Ala Tyr
                100                 105                 110

Pro Gly Gly Ala Ser Met Glu Ile His Gln Ala Leu Thr Arg Ser Ser
                115                 120                 125

Ile Ile Arg Asn Val Leu Pro Arg His Glu Gln Gly Gly Val Phe Ala
130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175

Leu Leu Asp Ser Val Pro Ile Val Ala Ile Thr Gly Gln Val Pro Arg
                180                 185                 190

Arg Met Ile Gly Thr Asp Ala Phe Gln Glu Thr Pro Ile Val Glu Val
                195                 200                 205

Thr Arg Ser Ile Thr Lys His Asn Tyr Leu Val Met Asp Val Glu Asp
                210                 215                 220

Ile Pro Arg Val Val Arg Glu Ala Phe Phe Leu Ala Arg Ser Gly Arg
225                 230                 235                 240

Pro Gly Pro Val Leu Ile Asp Val Pro Lys Asp Ile Gln Gln Gln Leu
                245                 250                 255

Val Ile Pro Asp Trp Asp Gln Pro Met Arg Leu Pro Gly Tyr Met Ser
                260                 265                 270

Arg Leu Pro Lys Leu Pro Asn Glu Met Leu Leu Glu Gln Ile Val Arg
                275                 280                 285

Leu Ile Ser Glu Ser Lys Lys Pro Val Leu Tyr Val Gly Gly Gly Cys
                290                 295                 300

Ser Gln Ser Ser Glu Glu Leu Arg Arg Phe Val Glu Leu Thr Gly Ile
305                 310                 315                 320

Pro Val Ala Ser Thr Leu Met Gly Leu Gly Ala Phe Pro Thr Gly Asp
                325                 330                 335

Glu Leu Ser Leu Ser Met Leu Gly Met His Gly Thr Val Tyr Ala Asn
                340                 345                 350

Tyr Ala Val Asp Ser Ser Asp Leu Leu Leu Ala Phe Gly Val Arg Phe
                355                 360                 365

Asp Asp Arg Val Thr Gly Lys Leu Glu Ala Phe Ala Ser Arg Ala Lys
                370                 375                 380

Ile Val His Ile Asp Ile Asp Ser Ala Glu Ile Gly Lys Asn Lys Gln
385                 390                 395                 400

Pro His Val Ser Ile Cys Ala Asp Ile Lys Leu Ala Leu Gln Gly Leu
                405                 410                 415

Asn Ser Ile Leu Glu Ser Lys Glu Gly Lys Leu Lys Leu Asp Phe Ser
                420                 425                 430

Ala Trp Arg Gln Glu Leu Thr Val Gln Lys Val Lys Tyr Pro Leu Asn
                435                 440                 445

Phe Lys Thr Phe Gly Asp Ala Ile Pro Pro Gln Tyr Ala Ile Gln Val
450                 455                 460

Leu Asp Glu Leu Thr Asn Gly Ser Ala Ile Ile Ser Thr Gly Val Gly
```

```
                465                 470                 475                 480
Gln His Gln Met Trp Ala Ala Gln Tyr Tyr Lys Tyr Arg Lys Pro Arg
                    485                 490                 495
Gln Trp Leu Thr Ser Gly Gly Leu Gly Ala Met Gly Phe Gly Leu Pro
                500                 505                 510
Ala Ala Ile Gly Ala Ala Val Gly Arg Pro Asp Glu Val Val Asp
            515                 520                 525
Ile Asp Gly Asp Gly Ser Phe Ile Met Asn Val Gln Glu Leu Ala Thr
        530                 535                 540
Ile Lys Val Glu Asn Leu Pro Val Lys Ile Met Leu Leu Asn Asn Gln
545                 550                 555                 560
His Leu Gly Met Val Val Gln Trp Glu Asp Arg Phe Tyr Lys Ala Asn
                565                 570                 575
Arg Ala His Thr Tyr Leu Gly Asn Pro Ser Asn Glu Ala Glu Ile Phe
            580                 585                 590
Pro Asn Met Leu Lys Phe Ala Glu Ala Cys Gly Val Pro Ala Ala Arg
                595                 600                 605
Val Thr His Arg Asp Asp Leu Arg Ala Ala Ile Gln Lys Met Leu Asp
        610                 615                 620
Thr Pro Gly Pro Tyr Leu Leu Asp Val Ile Val Pro His Gln Glu His
625                 630                 635                 640
Val Leu Pro Met Ile Pro Ser Gly Gly Ala Phe Lys Asp Val Ile Thr
                645                 650                 655
Glu Gly Asp Gly Arg Ser Ser Tyr
                660

<210> SEQ ID NO 5
<211> LENGTH: 1746
<212> TYPE: DNA
<213> ORGANISM: Paenibacillus polymyxa

<400> SEQUENCE: 5
atgtccgcac aaatacctga agttagaagt acaaatgaat tgagagaaaa atggatgaag      60
cctgaagtaa tcactggttc cgaaatattg ttaagatcat tgttattgga aggtgtcgat     120
tgtgtatttg gttatccagg tggtgctgtc ttgtacatct atgatgcaat gtacggtttt     180
aaagacttca gcatgttttt aaccagacac gaacaaggtg ctatacatgc tgcagatggt     240
tatgccagag cttccggtaa agtaggtgtt tgcatcgcaa caagtggtcc aggtgccacc     300
aatttggtta ctggtatcgc aacagccttt atggattctg ttcctttggt tgtcattact     360
ggtaacgtca tttcttcatt aatcggtaca gatgcattcc aagaagccga cataactggt     420
atcacaatgc caataactaa gcactcatat ttggttagag atgtcgaaga cttgcctaga     480
ataatccatg aagcatttca catagcaaat acaggtagaa agggtccagt tttgatagat     540
atccctaaag acatatccgc cgctcaaacc ttattcgtac acaaaccggt cctgttact      600
atgagaggtt acaacccaaa ggttttgcct aacaagatac aattggataa attgacacaa     660
gccatctccg aagctgaaag accattcatt ttggcaggtg gtggtgtagt ttatagtggt     720
ggtcatgaag cctatacgaa atttgttaga aagactgaaa tccctatcac tacaaccta      780
ttgggtttag gtggtttccc atcaggtcat gaattgtgga ctggtatgcc tggtatgcac     840
ggtacataca cctccaatca agcaatacaa caatctgatt tgttgatctg tattggtgct     900
agatttgatg acagagttac tggtaaattg atggtttcg caccacaagc caaaattgta     960
catatagata tcgaccctgc agaaataggt aaaaatgttg cagccgatat tccaatagta    1020
```

-continued

```
ggtgacgtta aggctgtctt agaattattg aaccaagatg ttaagagagc cgatagagct   1080
gacgcatgga gagcacaaat ccaacattgg aagaacgaaa agccatattc ctacaaggat   1140
agtgaaacag ttttgaaacc tcaatgggtc gtagaattat ggatgaaaac tacaaagggt   1200
ggtgctattg tcaccactga cgtaggtcaa caccaaatgt gggctgcaca atactacaag   1260
tttaatcaac caagatcatg ggttacatca ggtggtttag gtactatggg ttttggtttc   1320
ccatctgcta ttggtgcaca aatggccaat cctgatagat tggttatctc tattaacggt   1380
gacggtggta tgcaaatgtg ttcacaagaa ttagctattt gcgctattaa taacatccca   1440
gtaaagatcg ttatcattaa taccaagtt ttgggtatgg tcagacaatg caagaattg    1500 atctataaca acagatactc tcatattgat ttggctggtt cacctgactt tgtcaaattg   1560
gccgaagcct atggtgtaaa gggtttaaga gcaaccaata aggaagaagc cagaagagct   1620
tggcaagaag cattggatac tccaggtcct gttgtcgtag aatttgttgt ctctaaagaa   1680
gaaaacgttt atccaatggt tacacaaggt tccacaatag accaaatgtt gatgggtgac   1740
gaatga                                                               1746
```

<210> SEQ ID NO 6
<211> LENGTH: 581
<212> TYPE: PRT
<213> ORGANISM: Paenibacillus polymyxa

<400> SEQUENCE: 6

```
Met Ser Ala Gln Ile Pro Glu Val Arg Ser Thr Asn Glu Leu Arg Glu
1               5                   10                  15

Lys Trp Met Lys Pro Glu Val Ile Thr Gly Ser Glu Ile Leu Leu Arg
            20                  25                  30

Ser Leu Leu Leu Glu Gly Val Asp Cys Val Phe Gly Tyr Pro Gly Gly
        35                  40                  45

Ala Val Leu Tyr Ile Tyr Asp Ala Met Tyr Gly Phe Lys Asp Phe Lys
    50                  55                  60

His Val Leu Thr Arg His Glu Gln Gly Ala Ile His Ala Ala Asp Gly
65                  70                  75                  80

Tyr Ala Arg Ala Ser Gly Lys Val Gly Val Cys Ile Ala Thr Ser Gly
                85                  90                  95

Pro Gly Ala Thr Asn Leu Val Thr Gly Ile Ala Thr Ala Phe Met Asp
            100                 105                 110

Ser Val Pro Leu Val Val Ile Thr Gly Asn Val Ile Ser Ser Leu Ile
        115                 120                 125

Gly Thr Asp Ala Phe Gln Glu Ala Asp Ile Thr Gly Ile Thr Met Pro
    130                 135                 140

Ile Thr Lys His Ser Tyr Leu Val Arg Asp Val Glu Asp Leu Pro Arg
145                 150                 155                 160

Ile Ile His Glu Ala Phe His Ile Ala Asn Thr Gly Arg Lys Gly Pro
                165                 170                 175

Val Leu Ile Asp Ile Pro Lys Asp Ile Ser Ala Ala Gln Thr Leu Phe
            180                 185                 190

Val Pro Gln Thr Gly Pro Val Thr Met Arg Gly Tyr Asn Pro Lys Val
        195                 200                 205

Leu Pro Asn Lys Ile Gln Leu Asp Lys Leu Thr Gln Ala Ile Ser Glu
    210                 215                 220

Ala Glu Arg Pro Phe Ile Leu Ala Gly Gly Gly Val Val Tyr Ser Gly
225                 230                 235                 240
```

Gly His Glu Ala Leu Tyr Glu Phe Val Arg Lys Thr Glu Ile Pro Ile
                245                 250                 255

Thr Thr Thr Leu Leu Gly Leu Gly Gly Phe Pro Ser Gly His Glu Leu
            260                 265                 270

Trp Thr Gly Met Pro Gly Met His Gly Thr Tyr Thr Ser Asn Gln Ala
        275                 280                 285

Ile Gln Gln Ser Asp Leu Leu Ile Cys Ile Gly Ala Arg Phe Asp Asp
    290                 295                 300

Arg Val Thr Gly Lys Leu Asp Gly Phe Ala Pro Gln Ala Lys Ile Val
305                 310                 315                 320

His Ile Asp Ile Asp Pro Ala Glu Ile Gly Lys Asn Val Ala Ala Asp
                325                 330                 335

Ile Pro Ile Val Gly Asp Val Lys Ala Val Leu Glu Leu Leu Asn Gln
            340                 345                 350

Asp Val Lys Arg Ala Asp Arg Ala Asp Ala Trp Arg Ala Gln Ile Gln
        355                 360                 365

His Trp Lys Asn Glu Lys Pro Tyr Ser Tyr Lys Asp Ser Glu Thr Val
    370                 375                 380

Leu Lys Pro Gln Trp Val Val Glu Leu Leu Asp Glu Thr Thr Lys Gly
385                 390                 395                 400

Gly Ala Ile Val Thr Thr Asp Val Gly Gln His Gln Met Trp Ala Ala
                405                 410                 415

Gln Tyr Tyr Lys Phe Asn Gln Pro Arg Ser Trp Val Thr Ser Gly Gly
            420                 425                 430

Leu Gly Thr Met Gly Phe Gly Phe Pro Ser Ala Ile Gly Ala Gln Met
        435                 440                 445

Ala Asn Pro Asp Arg Leu Val Ile Ser Ile Asn Gly Asp Gly Gly Met
450                 455                 460

Gln Met Cys Ser Gln Glu Leu Ala Ile Cys Ala Ile Asn Asn Ile Pro
465                 470                 475                 480

Val Lys Ile Val Ile Asn Asn Gln Val Leu Gly Met Val Arg Gln
                485                 490                 495

Trp Gln Glu Leu Ile Tyr Asn Asn Arg Tyr Ser His Ile Asp Leu Ala
            500                 505                 510

Gly Ser Pro Asp Phe Val Lys Leu Ala Glu Ala Tyr Gly Val Lys Gly
        515                 520                 525

Leu Arg Ala Thr Asn Lys Glu Glu Ala Arg Arg Ala Trp Gln Glu Ala
    530                 535                 540

Leu Asp Thr Pro Gly Pro Val Val Val Glu Phe Val Val Ser Lys Glu
545                 550                 555                 560

Glu Asn Val Tyr Pro Met Val Thr Gln Gly Ser Thr Ile Asp Gln Met
                565                 570                 575

Leu Met Gly Asp Glu
            580

<210> SEQ ID NO 7
<211> LENGTH: 860
<212> TYPE: DNA
<213> ORGANISM: Brevibacillus brevis

<400> SEQUENCE: 7
atgggtaaga agaacattat tacctctatc acctccttgg ctttggttgc tggtttgtct    60
ttgactgctt tgctgctac tactgctact gttccagctc accagctaa acaagaatct   120

```
aaaccagctg ttgctgctaa tccagctcct aagaatgttt tgttccaata ctctaccatc   180
aacgccttga tgtttgggtca atttgaaggt gatttgacct tgaaggactt gaagttgaga   240
ggtgatatgg gtttgggtac tatcaatgat ttggacggtg aaatgatcca aatgggtact   300
aagttctacc aaatcgattc taccggtaag ttgtctgaat tgccagaatc tgttaagact   360
ccattcgctg ttactactca cttcgaacct aagaaaaga ctaccttgac caacgtccaa    420
gactacaatc aattgaccaa gatgttggaa gaaaagttcg aaaacaagaa cgttttctac   480
gccgttaagt tgactggtac tttcaaaatg gttaaggcta gaaccgttcc taagcaaact   540
agaccatatc cacaattgac tgaagtcacc aagaagcaat ccgaatttga attcaagaac   600
gtcaagggta ctttgatcgg tttttacact ccaaattatg ctgctgcttt gaacgttcca   660
ggttttcact tgcatttcat taccgaagat aagacctctg gtggtcatgt tttgaacttg   720
caatttgata acgccaactt ggaaatctcc ccaatccatg aatttgatgt tcaattgcca   780
cacaccgatg atttcgctca ttctgatttg actcaagtta ctacctccca agttcatcaa   840
gctgaatctg aaagaaagta                                               860

<210> SEQ ID NO 8
<211> LENGTH: 286
<212> TYPE: PRT
<213> ORGANISM: Brevibacillus brevis

<400> SEQUENCE: 8

Met Gly Lys Lys Asn Ile Ile Thr Ser Ile Thr Ser Leu Ala Leu Val
1               5                   10                  15

Ala Gly Leu Ser Leu Thr Ala Phe Ala Ala Thr Thr Ala Thr Val Pro
                20                  25                  30

Ala Pro Pro Ala Lys Gln Glu Ser Lys Pro Ala Val Ala Ala Asn Pro
            35                  40                  45

Ala Pro Lys Asn Val Leu Phe Gln Tyr Ser Thr Ile Asn Ala Leu Met
        50                  55                  60

Leu Gly Gln Phe Glu Gly Asp Leu Thr Leu Lys Asp Leu Lys Leu Arg
65                  70                  75                  80

Gly Asp Met Gly Leu Gly Thr Ile Asn Asp Leu Asp Gly Glu Met Ile
                85                  90                  95

Gln Met Gly Thr Lys Phe Tyr Gln Ile Asp Ser Thr Gly Lys Leu Ser
            100                 105                 110

Glu Leu Pro Glu Ser Val Lys Thr Pro Phe Ala Val Thr Thr His Phe
        115                 120                 125

Glu Pro Lys Glu Lys Thr Thr Leu Thr Asn Val Gln Asp Tyr Asn Gln
    130                 135                 140

Leu Thr Lys Met Leu Glu Glu Lys Phe Glu Asn Lys Asn Val Phe Tyr
145                 150                 155                 160

Ala Val Lys Leu Thr Gly Thr Phe Lys Met Val Lys Ala Arg Thr Val
                165                 170                 175

Pro Lys Gln Thr Arg Pro Tyr Pro Gln Leu Thr Glu Val Thr Lys Lys
            180                 185                 190

Gln Ser Glu Phe Glu Phe Lys Asn Val Lys Gly Thr Leu Ile Gly Phe
        195                 200                 205

Tyr Thr Pro Asn Tyr Ala Ala Ala Leu Asn Val Pro Gly Phe His Leu
    210                 215                 220

His Phe Ile Thr Glu Asp Lys Thr Ser Gly Gly His Val Leu Asn Leu
225                 230                 235                 240
```

Gln Phe Asp Asn Ala Asn Leu Glu Ile Ser Pro Ile His Glu Phe Asp
                245                 250                 255

Val Gln Leu Pro His Thr Asp Asp Phe Ala His Ser Leu Thr Gln
        260                 265                 270

Val Thr Thr Ser Gln Val His Gln Ala Glu Ser Glu Arg Lys
    275                 280                 285

<210> SEQ ID NO 9
<211> LENGTH: 783
<212> TYPE: DNA
<213> ORGANISM: Enterobacter aerogenes

<400> SEQUENCE: 9

```
atgatgatgc actcctccgc ctgcgactgt gaagcaagtt tatgcgaaac attgagaggt      60
ttttccgcca agcacccaga ttccgttata tatcaaacat ccttgatgag tgctttgtta     120
tctggtgtct acgaaggtga cactacaatc gcagacttgt tagctcatgg tgactttggt     180
ttgggtactt ttaatgaatt agacggtgaa atgatcgcat tttcttcaca agtttaccaa     240
ttgagagctg atggttcagc aagagctgca aaaccagaac aaaagacacc ttttgcagtc     300
atgacctggt tccaaccaca atacagaaaa acttttgatg ccccagtttc aagacaacaa     360
attcacgatg taatagacca acaaatccct tcagataatt tgttttgtgc cttgagaata     420
gacggtaact tcagacatgc tcacaccaga actgttccaa gacaaactcc acctatagaa     480
gccatgacag atgtattgga tgaccaacct gtttttagat tcaatcaaag agaaggtgtt     540
ttagtcggtt ttagaacccc acaacacatg caaggtatca acgtagcagg ttatcatgaa     600
cacttcatta ctgatgacag acaaggtggt ggtcatttgt tagattacca attggaatcc     660
ggtgttttga cattcggtga atccacaag ttgatgattg atttgccagc cgacagtgct     720
ttcttacaag ccaacttaca cccatcaaac ttagacgccg caatcagatc agtagaaaac     780
taa                                                                   783
```

<210> SEQ ID NO 10
<211> LENGTH: 260
<212> TYPE: PRT
<213> ORGANISM: Enterobacter aerogenes

<400> SEQUENCE: 10

Met Met Met His Ser Ser Ala Cys Asp Cys Glu Ala Ser Leu Cys Glu
1               5                   10                  15

Thr Leu Arg Gly Phe Ser Ala Lys His Pro Asp Ser Val Ile Tyr Gln
            20                  25                  30

Thr Ser Leu Met Ser Ala Leu Leu Ser Gly Val Tyr Glu Gly Asp Thr
        35                  40                  45

Thr Ile Ala Asp Leu Leu His Gly Asp Phe Gly Leu Gly Thr Phe
    50                  55                  60

Asn Glu Leu Asp Gly Glu Met Ile Ala Phe Ser Ser Gln Val Tyr Gln
65                  70                  75                  80

Leu Arg Ala Asp Gly Ser Ala Arg Ala Ala Lys Pro Glu Gln Lys Thr
                85                  90                  95

Pro Phe Ala Val Met Thr Trp Phe Gln Pro Gln Tyr Arg Lys Thr Phe
            100                 105                 110

Asp Ala Pro Val Ser Arg Gln Gln Ile His Asp Val Ile Asp Gln Gln
        115                 120                 125

Ile Pro Ser Asp Asn Leu Phe Cys Ala Leu Arg Ile Asp Gly Asn Phe
    130                 135                 140

```
Arg His Ala His Thr Arg Thr Val Pro Arg Gln Thr Pro Tyr Arg
145                 150                 155                 160

Ala Met Thr Asp Val Leu Asp Asp Gln Pro Val Phe Arg Phe Asn Gln
            165                 170                 175

Arg Glu Gly Val Leu Val Gly Phe Arg Thr Pro Gln His Met Gln Gly
        180                 185                 190

Ile Asn Val Ala Gly Tyr His Glu His Phe Ile Thr Asp Asp Arg Gln
    195                 200                 205

Gly Gly Gly His Leu Leu Asp Tyr Gln Leu Glu Ser Gly Val Leu Thr
210                 215                 220

Phe Gly Glu Ile His Lys Leu Met Ile Asp Leu Pro Ala Asp Ser Ala
225                 230                 235                 240

Phe Leu Gln Ala Asn Leu His Pro Ser Asn Leu Asp Ala Ala Ile Arg
                245                 250                 255

Ser Val Glu Asn
            260

<210> SEQ ID NO 11
<211> LENGTH: 666
<212> TYPE: DNA
<213> ORGANISM: Lactococcus lactis

<400> SEQUENCE: 11
atgtcatcga gaatctttca acacaatacc ttcacaactt tgagtagcgg attttacaaa     60
ggcacaatca cgttgaaaga agccttagaa cacggatcag ttggcatagg tacattagat    120
actgcaaatg gtgaagttac catcatcaac ggtatagcct atcatggaga ttcggaaaac    180
catgtgagat ggtggaaaga ggatgaaacg atgccttatg tcgctatggt tgaacatcaa    240
cccattgcaa agttcactga ttcctctgtg tcaaatagcg aagatttcct atccgcttta    300
accaaaaggt ttccaaccgt taatactgcc tacacaattg tcatgactgg tcagtttaag    360
gaagtaactg tctcttctaa accagcgaac aatactagac atatgacga ataatggct     420 gatcaaccgt actttacaaa ggagaacatt agtggtacaa tggttggtgt atgggctcct    480
aaacatctta ctgatctatt tgggttaggc tttcaccttc acttcgtttc tgacgataag    540
acgtttactg cacatgtaca gaatttcatt acagagaatc tggaaattga tagggaaa     600 attaccaaga ttgaccaaga atttcctgat gatgacgaga cttcgacca acatttgttc    660 caataa                                                                666

<210> SEQ ID NO 12
<211> LENGTH: 221
<212> TYPE: PRT
<213> ORGANISM: Lactococcus lactis

<400> SEQUENCE: 12

Met Ser Ser Arg Ile Phe Gln His Asn Thr Phe Thr Thr Leu Ser Ser
1               5                   10                  15

Gly Phe Tyr Lys Gly Thr Ile Thr Leu Lys Glu Ala Leu Glu His Gly
            20                  25                  30

Ser Val Gly Ile Gly Thr Leu Asp Thr Ala Asn Gly Glu Val Thr Ile
        35                  40                  45

Ile Asn Gly Ile Ala Tyr His Gly Asp Ser Glu Asn His Val Arg Leu
    50                  55                  60

Val Glu Glu Asp Glu Thr Met Pro Tyr Val Ala Met Val Glu His Gln
65                  70                  75                  80
```

```
Pro Ile Ala Lys Phe Thr Asp Ser Ser Val Ser Asn Ser Glu Asp Phe
            85                  90                  95

Leu Ser Ala Leu Thr Lys Arg Phe Pro Thr Val Asn Thr Ala Tyr Thr
            100                 105                 110

Ile Val Met Thr Gly Gln Phe Lys Glu Val Thr Val Ser Ser Lys Pro
            115                 120                 125

Ala Asn Asn Thr Arg Pro Tyr Asp Glu Ile Met Ala Asp Gln Pro Tyr
            130                 135                 140

Phe Thr Lys Glu Asn Ile Ser Gly Thr Met Val Gly Val Trp Ala Pro
145                 150                 155                 160

Lys His Leu Thr Asp Leu Phe Gly Leu Gly Phe His Leu His Phe Val
            165                 170                 175

Ser Asp Asp Lys Thr Phe Thr Ala His Val Gln Asn Phe Ile Thr Glu
            180                 185                 190

Asn Leu Glu Ile Glu Ile Gly Lys Ile Thr Lys Ile Asp Gln Glu Phe
            195                 200                 205

Pro Asp Asp Asp Glu Asn Phe Asp Gln His Leu Phe Gln
            210                 215                 220

<210> SEQ ID NO 13
<211> LENGTH: 1341
<212> TYPE: DNA
<213> ORGANISM: Lactococcus lactis

<400> SEQUENCE: 13
atgggtattg tcgtaatagg tactaaccat gccggaatag ctacagcaaa taccttaatc      60
gaccaatatc caggacatga aattgttatg attgacagaa actcgaatat gagttatctt     120
ggctgtggta cagcgatttg ggttgggaga caaatcgaga aacctgatga acttttctat     180
gcaaaagcag aagatttcga aaagaagggt gttaaaatcc tgaccgagac tgaagtgtca     240
gaaatcgact ttaccaacaa aatgatatat gccaaaagca agactgggga gaaaatcacg     300
gaatcttatg ataagctagt attggcaaca ggaagcagac caatcatacc caatttgcct     360
ggtaaagatc ttaaaggaat tcatttctta aagttattcc aggaaggtca agccattgac     420
gaagaattcg caaagaatga cgtgaaaaga atcgcggtaa ttggtgctgg ttatattgga     480
acagagatag ctgaagcagc taaacgtaga gggaagaag tgttgttgtt tgatgctgaa     540
agtacctcat tagcgtcata ctacgacgaa gaatttgcca aaggcatgga tgaaaatttg     600
gcacaacacg ggattgagtt gcactttggt gaacttgccc aagagttcaa ggcaaatgaa     660
gaaggtcatg tctcccagat tgttacaaac aaatccactt atgatgtgga tctggtcatc     720
aattgcatag gatttactgc caattcagcc ttagctggtg agcatctaga aacgtttaag     780
aacggtgcca taaaggttaa taagcatcaa caatctagtg atccagacgt gtatgcagtt     840
ggtgatgttg caactatcta ctctaacgct ttgcaagact ttacttacat cgctttagct     900
agcaatgctg ttagatcagg cattgttgct ggacacaata ttggcggtaa atccatagaa     960
tctgtcggtg ttcagggtag taacggcatt tctatattcg gatacaatat gacaagtact    1020
ggtttatcag taaaagctgc taagaagatt ggtctagaag tctccttttc tgattttgaa    1080
gataagcaaa aggcttggtt tctgcatgag aacaatgatt cggtcaaaat aaggatcgta    1140
tacgaaacaa atccaggag aataattggc gcacaattgg catcgaaatc agagattata    1200
gcgggcaaca ttaacatgtt ctctttagcc attcaggaaa gaaaacgat tgatgagtta    1260 gcccctattgg atttgttctt tctgcctcac tttaactctc cgtacaatta tatgaccgta    1320
```
gctgcgttga atgctaaata a                                                                      1341

<210> SEQ ID NO 14
<211> LENGTH: 446
<212> TYPE: PRT
<213> ORGANISM: Lactococcus lactis

<400> SEQUENCE: 14

Met Gly Ile Val Val Ile Gly Thr Asn His Ala Gly Ile Ala Thr Ala
1               5                   10                  15

Asn Thr Leu Ile Asp Gln Tyr Pro Gly His Glu Ile Val Met Ile Asp
            20                  25                  30

Arg Asn Ser Asn Met Ser Tyr Leu Gly Cys Gly Thr Ala Ile Trp Val
        35                  40                  45

Gly Arg Gln Ile Glu Lys Pro Asp Glu Leu Phe Tyr Ala Lys Ala Glu
    50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Asp Leu Lys Gly Ile His
        115                 120                 125

Phe Leu Lys Leu Phe Gln Glu Gly Gln Ala Ile Asp Glu Glu Phe Ala
    130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Gln Glu Phe Lys Ala Asn Glu Glu Gly His Val
    210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asn Lys His Gln Gln Ser
            260                 265                 270

Ser Asp Pro Asp Val Tyr Ala Val Gly Asp Val Ala Thr Ile Tyr Ser
        275                 280                 285

Asn Ala Leu Gln Asp Phe Thr Tyr Ile Ala Leu Ala Ser Asn Ala Val
    290                 295                 300

Arg Ser Gly Ile Val Ala Gly His Asn Ile Gly Gly Lys Ser Ile Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Lys Ile Gly Leu
            340                 345                 350

Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
     370                 375                 380

Ser Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415

Ile Asp Glu Leu Ala Leu Leu Asp Leu Phe Phe Leu Pro His Phe Asn
            420                 425                 430

Ser Pro Tyr Asn Tyr Met Thr Val Ala Ala Leu Asn Ala Lys
        435                 440                 445

<210> SEQ ID NO 15
<211> LENGTH: 1380
<212> TYPE: DNA
<213> ORGANISM: Streptococcus pneumoniae

<400> SEQUENCE: 15

| | | | | | |
|---|---|---|---|---|---|
| atgtctaaga | tagtggtagt | tggtgctaac | catgcaggaa | ctgcttgcat | caatacgatg | 60 |
| ttggataatt | tcggcaatga | aaatgagata | gtggtgtttg | atcagaattc | caacatcagc | 120 |
| tttctaggtt | gtggtatggc | gttatggatt | ggggagcaaa | tagatggtgc | tgaagggttg | 180 |
| ttttactcag | acaaagagaa | attggaagcc | aaaggtgcca | agtctacat | gaattcgcca | 240 |
| gtcctgagta | tagactatga | caacaaagtg | gtaactgcag | aagtagaagg | caaagagcac | 300 |
| aaagaatcct | atgagaaact | gatctttgct | actggttcaa | caccgatttt | accacctatt | 360 |
| gaaggagtcg | agatcgttaa | aggtaataga | gaatttaagg | ccacacttga | aaacgtacaa | 420 |
| tttgttaagt | tgtatcagaa | tgctgaagaa | gtcatcaaca | agctttcaga | taaaagccag | 480 |
| catttagata | ggattgctgt | tgttggaggt | ggatacattg | tgttgaatt | ggctgaagcc | 540 |
| tttgaaagac | taggaaaaga | agttgtgtta | gttgacattg | tggacactgt | cttaaacggg | 600 |
| tattatgaca | agatttcac | ccaaatgatg | gccaagaatc | ttgaggatca | aacattaga | 660 |
| cttgctttag | ccaaacagt | gaaggctatt | gaaggcgatg | gtaaggtaga | aggttgatt | 720 |
| acagacaagg | agtctttcga | tgttgacatg | gtcattttag | cagtaggatt | tagaccaaac | 780 |
| actgctttgg | cagatgggaa | aattgaattg | tttagaaatg | gtgcttttct | ggtggataag | 840 |
| aaacaagaaa | cttcaatacc | cgatgtttat | gcagttggtg | attgtgcaac | agtctatgat | 900 |
| aatgccagaa | aggatacttc | ctacatagca | ttggcatcta | atgcagttag | aacgggcatt | 960 |
| gttggtgctt | ataatgcctg | tggtcatgaa | ttggagggca | ttggtgtcca | aggttctaat | 1020 |
| ggtatatcga | tttatggcct | tcatatggtt | agtaccggat | tgactctgga | aaggccaaa | 1080 |
| gctgctggat | acaatgcgac | agaaacaggt | ttcaacgatt | tacagaagcc | agagtttatg | 1140 |
| aaacacgaca | accatgaagt | agcgatcaaa | atcgtatttg | acaaggattc | tcgtgaaatt | 1200 |
| ctaggggcac | aaatggtttc | acacgatata | gcgataagta | tgggcatcca | tatgttctct | 1260 |
| ctagcgattc | aagaacatgt | taccatagat | aaattagcat | taaccgatct | attcttcttg | 1320 |
| cctcatttca | caaaaccta | caattacatc | acgatggcag | ctttgaccgc | cgaaaagtaa | 1380 |

<210> SEQ ID NO 16
<211> LENGTH: 459
<212> TYPE: PRT
<213> ORGANISM: Streptococcus pneumoniae

<400> SEQUENCE: 16

Met Ser Lys Ile Val Val Val Gly Ala Asn His Ala Gly Thr Ala Cys

-continued

```
  1               5                  10                 15
Ile Asn Thr Met Leu Asp Asn Phe Gly Asn Glu Asn Glu Ile Val Val
               20                 25                 30
Phe Asp Gln Asn Ser Asn Ile Ser Phe Leu Gly Cys Gly Met Ala Leu
               35                 40                 45
Trp Ile Gly Glu Gln Ile Asp Gly Ala Glu Gly Leu Phe Tyr Ser Asp
               50                 55                 60
Lys Glu Lys Leu Glu Ala Lys Gly Ala Lys Val Tyr Met Asn Ser Pro
 65                70                 75                 80
Val Leu Ser Ile Asp Tyr Asp Asn Lys Val Val Thr Ala Glu Val Glu
               85                 90                 95
Gly Lys Glu His Lys Glu Ser Tyr Glu Lys Leu Ile Phe Ala Thr Gly
              100                105                110
Ser Thr Pro Ile Leu Pro Pro Ile Glu Gly Val Glu Ile Val Lys Gly
              115                120                125
Asn Arg Glu Phe Lys Ala Thr Leu Glu Asn Val Gln Phe Val Lys Leu
              130                135                140
Tyr Gln Asn Ala Glu Glu Val Ile Asn Lys Leu Ser Asp Lys Ser Gln
145               150                155                160
His Leu Asp Arg Ile Ala Val Val Gly Gly Tyr Ile Gly Val Glu
              165                170                175
Leu Ala Glu Ala Phe Glu Arg Leu Gly Lys Glu Val Val Leu Val Asp
              180                185                190
Ile Val Asp Thr Val Leu Asn Gly Tyr Tyr Asp Lys Asp Phe Thr Gln
              195                200                205
Met Met Ala Lys Asn Leu Glu Asp His Asn Ile Arg Leu Ala Leu Gly
              210                215                220
Gln Thr Val Lys Ala Ile Glu Gly Asp Gly Lys Val Glu Arg Leu Ile
225               230                235                240
Thr Asp Lys Glu Ser Phe Asp Val Asp Met Val Ile Leu Ala Val Gly
              245                250                255
Phe Arg Pro Asn Thr Ala Leu Ala Asp Gly Lys Ile Glu Leu Phe Arg
              260                265                270
Asn Gly Ala Phe Leu Val Asp Lys Lys Gln Glu Thr Ser Ile Pro Asp
              275                280                285
Val Tyr Ala Val Gly Asp Cys Ala Thr Val Tyr Asp Asn Ala Arg Lys
              290                295                300
Asp Thr Ser Tyr Ile Ala Leu Ala Ser Asn Ala Val Arg Thr Gly Ile
305               310                315                320
Val Gly Ala Tyr Asn Ala Cys Gly His Glu Leu Glu Gly Ile Gly Val
              325                330                335
Gln Gly Ser Asn Gly Ile Ser Ile Tyr Gly Leu His Met Val Ser Thr
              340                345                350
Gly Leu Thr Leu Glu Lys Ala Lys Ala Gly Tyr Asn Ala Thr Glu
              355                360                365
Thr Gly Phe Asn Asp Leu Gln Lys Pro Glu Phe Met Lys His Asp Asn
              370                375                380
His Glu Val Ala Ile Lys Ile Val Phe Asp Lys Asp Ser Arg Glu Ile
385               390                395                400
Leu Gly Ala Gln Met Val Ser His Asp Ile Ala Ile Ser Met Gly Ile
              405                410                415
His Met Phe Ser Leu Ala Ile Gln Glu His Val Thr Ile Asp Lys Leu
              420                425                430
```

Ala Leu Thr Asp Leu Phe Phe Leu Pro His Phe Asn Lys Pro Tyr Asn
        435                 440                 445

Tyr Ile Thr Met Ala Ala Leu Thr Ala Glu Lys
    450                 455

<210> SEQ ID NO 17
<211> LENGTH: 1341
<212> TYPE: DNA
<213> ORGANISM: Enterococcus faecalis

<400> SEQUENCE: 17
atgtctgtgg ttgtcgtagg ctgtacacat gctggtacta gtgcagtgaa atctatccta      60
gctaatcatc ccgaagctga agtcactgtt tatgaacgta atgacaacat atccttcttg     120
tcttgtggaa ttgcacttta tgttggaggt gtagttaaga atgctgccga cttattttac     180
agcaatcctg aggaattagc cagtttagga gccactgtga aaatggaaca caacgtagaa     240
gagatcaatg tcgatgataa gacagttacg gcaaagaatc tacaaacagg tgcaacagaa     300
accgtatcct acgataagtt ggtcatgact actggaagtt ggcctataat tccaccaata     360
cccggaattg atgctgagaa cattctactt tgcaagaatt attctcaagc gaatgtcatt     420
atcgaaaagg ccaaagatgc gaaaagagtc gttgtcgttg gtggtggcta tattggtata     480
gagttagttg aagcttttgt tgaaagcggt aaacaggtga ccctagttga tggtctagac     540
aggattttga caagtatttt ggacaaaccg tttactgatg ttttagaaaa ggagttagtt     600
gatagaggtg tgaacttagc cttaggtgaa atgtccaac agtttgtagc tgatgaacag      660
ggaaaagttg caaaagttat cactccatct caagaattcg aagcagacat ggtcataatg     720
tgtgttggct ttagaccaaa taccgaactt tgaaagaca agttgatat gttgcctaac       780
ggtgcaattg aggttaacga gtatatgcaa acgtccaatc cagatatctt tgctgctggt     840
gattcagccg tagtgcatta caacccatcg caaacgaaga attatattcc cttagcgact     900
aatgcagtaa cacagggtat gttggtgggg agaaacttga cagaacagaa acttgcctat     960
agaggcaccc aagtacgtc tggcttgtac ttgttcggtt ggaaaattgg ctcaacagga    1020
gtaaccaaag aatcggcaaa attgaatggg ttagatgttg aagctacagt ctttgaggat    1080
aactatagac ctgaattcat gccaacaacc gaaaaggtgc tgatggagct ggtgtacgaa    1140
aaggggactc aaaggatagt aggtgggcaa ttgatgtcca aatacgatat cactcaatca    1200
gcgaatacac tttcattggc tgtacagaac aaaatgaccg ttgaagatct ggctatttca    1260
gacttcttct tcaaccgca ctttgaccgt ccttggaatt acttaaattt gctagcccaa    1320
gcagctctgg agaacatgta a                                              1341

<210> SEQ ID NO 18
<211> LENGTH: 446
<212> TYPE: PRT
<213> ORGANISM: Enterococcus faecalis

<400> SEQUENCE: 18

Met Ser Val Val Val Gly Cys Thr His Ala Gly Thr Ser Ala Val
1               5                  10                  15

Lys Ser Ile Leu Ala Asn His Pro Glu Ala Glu Val Thr Val Tyr Glu
                20                  25                  30

Arg Asn Asp Asn Ile Ser Phe Leu Ser Cys Gly Ile Ala Leu Tyr Val
            35                  40                  45

Gly Gly Val Val Lys Asn Ala Ala Asp Leu Phe Tyr Ser Asn Pro Glu

```
            50                  55                  60
Glu Leu Ala Ser Leu Gly Ala Thr Val Lys Met Glu His Asn Val Glu
 65                  70                  75                  80

Glu Ile Asn Val Asp Asp Lys Thr Val Thr Ala Lys Asn Leu Gln Thr
                 85                  90                  95

Gly Ala Thr Glu Thr Val Ser Tyr Asp Lys Leu Val Met Thr Thr Gly
            100                 105                 110

Ser Trp Pro Ile Ile Pro Pro Ile Pro Gly Ile Asp Ala Glu Asn Ile
        115                 120                 125

Leu Leu Cys Lys Asn Tyr Ser Gln Ala Asn Val Ile Ile Glu Lys Ala
130                 135                 140

Lys Asp Ala Lys Arg Val Val Val Gly Gly Tyr Ile Gly Ile
145                 150                 155                 160

Glu Leu Val Glu Ala Phe Val Glu Ser Gly Lys Gln Val Thr Leu Val
                165                 170                 175

Asp Gly Leu Asp Arg Ile Leu Asn Lys Tyr Leu Asp Lys Pro Phe Thr
            180                 185                 190

Asp Val Leu Glu Lys Glu Leu Val Asp Arg Gly Val Asn Leu Ala Leu
        195                 200                 205

Gly Glu Asn Val Gln Gln Phe Val Ala Asp Glu Gln Gly Lys Val Ala
210                 215                 220

Lys Val Ile Thr Pro Ser Gln Glu Phe Glu Ala Asp Met Val Ile Met
225                 230                 235                 240

Cys Val Gly Phe Arg Pro Asn Thr Glu Leu Leu Lys Asp Lys Val Asp
                245                 250                 255

Met Leu Pro Asn Gly Ala Ile Glu Val Asn Glu Tyr Met Gln Thr Ser
            260                 265                 270

Asn Pro Asp Ile Phe Ala Ala Gly Asp Ser Ala Val Val His Tyr Asn
        275                 280                 285

Pro Ser Gln Thr Lys Asn Tyr Ile Pro Leu Ala Thr Asn Ala Val Arg
290                 295                 300

Gln Gly Met Leu Val Gly Arg Asn Leu Thr Glu Gln Lys Leu Ala Tyr
305                 310                 315                 320

Arg Gly Thr Gln Gly Thr Ser Gly Leu Tyr Leu Phe Gly Trp Lys Ile
                325                 330                 335

Gly Ser Thr Gly Val Thr Lys Glu Ser Ala Lys Leu Asn Gly Leu Asp
            340                 345                 350

Val Glu Ala Thr Val Phe Glu Asp Asn Tyr Arg Pro Glu Phe Met Pro
        355                 360                 365

Thr Thr Glu Lys Val Leu Met Glu Leu Val Tyr Glu Lys Gly Thr Gln
370                 375                 380

Arg Ile Val Gly Gly Leu Met Ser Lys Tyr Asp Ile Thr Gln Ser
385                 390                 395                 400

Ala Asn Thr Leu Ser Leu Ala Val Gln Asn Lys Met Thr Val Glu Asp
                405                 410                 415

Leu Ala Ile Ser Asp Phe Phe Phe Gln Pro His Phe Asp Arg Pro Trp
            420                 425                 430

Asn Tyr Leu Asn Leu Leu Ala Gln Ala Ala Leu Glu Asn Met
        435                 440                 445

<210> SEQ ID NO 19
<211> LENGTH: 1356
<212> TYPE: DNA
<213> ORGANISM: Lactobacillus brevis
```

<400> SEQUENCE: 19

```
atgtctaagg ttaccgtggt aggttgtaca catgccggta cttttgcaat caaacagatt    60
ttggcagaac atcctgatgc agaagtaaca gtctatgaga gaaatgacgt gattagcttc   120
ttgtcgtgtg catagcgtt gtacttgggt gggaaagttg ctgaccctca agggcttttc   180
tactcatcac cagaagagtt acaaaagctt ggggcgaatg tccaaatgaa ccacaacgtt   240
ttagcgatag atccagatca aaagactgtt actgttgaag atctaacgag tcatgctcag   300
acaacagaat cctatgacaa gttagtcatg acttcaggtt cttggccgat agttcccaaa   360
ataccaggta ttgactccga tagagtcaag ctgtgcaaga attgggctca tgcacaagct   420
ttgattgaag atgctaaaga agcgaaaaga attactgtca ttggcgctgg ttatatcggt   480
gccgaattgg ccgaagcgta ttctactaca ggtcacgacg taacgttgat agacgcaatg   540
gatagagtaa tgcccaaata ctttgatgca gattttaccg atgtcattga gcaagattat   600
cgtgatcatg gagtgcaatt agccttgagt gaaactgttg aatcgtttac agacagtgct   660
acaggattga ccataaagac tgacaagaat agttacgaaa cagatcttgc catcttatgc   720
attggcttta gaccaaatac ggatctgctg aaaggaaaag ttgatatggc accaaatggt   780
gctattatta ccgatgacta tatgcgttcc tctaatccgg acatatttgc tgcaggagac   840
tctgctgcag ttcactataa ccctacacac cagaatgcat atatcccact agccacaaat   900
gctgtgagac aaggtatatt agtaggcaag aatttggtca aaccgaccgt taaatacatg   960
ggtacgcaaa gctcttcagg tcttgccctg tacgatagga ctattgtttc gaccggctta  1020
acgctagcag cagctaaaca acagggtgtt aatgctgaac aggtgatcgt tgaggacaat  1080
tatagacctg agtttatgcc ttcaactgaa cccgtgctaa tgagcttagt ctttgatcca  1140
gatactcata ggatcttagg aggagctttg atgtccaaat acgatgtatc ccagtctgca  1200
aacaccttgt ctgtgtgtat ccaaaacgag aatactattg atgacttagc catggttgat  1260
atgcttttcc aacctaactt cgatagacca ttcaactatc taaacatttt ggctcaagct  1320
gctcaagcca aagtagctca atcagtaaac gcctag                             1356
```

<210> SEQ ID NO 20
<211> LENGTH: 451
<212> TYPE: PRT
<213> ORGANISM: Lactobacillus brevis

<400> SEQUENCE: 20

```
Met Ser Lys Val Thr Val Val Gly Cys Thr His Ala Gly Thr Phe Ala
1               5                   10                  15

Ile Lys Gln Ile Leu Ala Glu His Pro Asp Ala Glu Val Thr Val Tyr
            20                  25                  30

Glu Arg Asn Asp Val Ile Ser Phe Leu Ser Cys Gly Ile Ala Leu Tyr
        35                  40                  45

Leu Gly Gly Lys Val Ala Asp Pro Gln Gly Leu Phe Tyr Ser Ser Pro
    50                  55                  60

Glu Glu Leu Gln Lys Leu Gly Ala Asn Val Gln Met Asn His Asn Val
65                  70                  75                  80

Leu Ala Ile Asp Pro Asp Gln Lys Thr Val Thr Val Glu Asp Leu Thr
                85                  90                  95

Ser His Ala Gln Thr Thr Glu Ser Tyr Asp Lys Leu Val Met Thr Ser
            100                 105                 110

Gly Ser Trp Pro Ile Val Pro Lys Ile Pro Gly Ile Asp Ser Asp Arg
```

```
            115                 120                 125
Val Lys Leu Cys Lys Asn Trp Ala His Ala Gln Ala Leu Ile Glu Asp
            130                 135                 140

Ala Lys Glu Ala Lys Arg Ile Thr Val Ile Gly Ala Gly Tyr Ile Gly
145                 150                 155                 160

Ala Glu Leu Ala Glu Ala Tyr Ser Thr Thr Gly His Asp Val Thr Leu
                165                 170                 175

Ile Asp Ala Met Asp Arg Val Met Pro Lys Tyr Phe Asp Ala Asp Phe
            180                 185                 190

Thr Asp Val Ile Glu Gln Asp Tyr Arg Asp His Gly Val Gln Leu Ala
        195                 200                 205

Leu Ser Glu Thr Val Glu Ser Phe Thr Asp Ser Ala Thr Gly Leu Thr
210                 215                 220

Ile Lys Thr Asp Lys Asn Ser Tyr Glu Thr Asp Leu Ala Ile Leu Cys
225                 230                 235                 240

Ile Gly Phe Arg Pro Asn Thr Asp Leu Leu Lys Gly Lys Val Asp Met
                245                 250                 255

Ala Pro Asn Gly Ala Ile Ile Thr Asp Asp Tyr Met Arg Ser Ser Asn
            260                 265                 270

Pro Asp Ile Phe Ala Ala Gly Asp Ser Ala Ala Val His Tyr Asn Pro
        275                 280                 285

Thr His Gln Asn Ala Tyr Ile Pro Leu Ala Thr Asn Ala Val Arg Gln
    290                 295                 300

Gly Ile Leu Val Gly Lys Asn Leu Val Lys Pro Thr Val Lys Tyr Met
305                 310                 315                 320

Gly Thr Gln Ser Ser Ser Gly Leu Ala Leu Tyr Asp Arg Thr Ile Val
                325                 330                 335

Ser Thr Gly Leu Thr Leu Ala Ala Ala Lys Gln Gln Gly Val Asn Ala
            340                 345                 350

Glu Gln Val Ile Val Glu Asp Asn Tyr Arg Pro Glu Phe Met Pro Ser
        355                 360                 365

Thr Glu Pro Val Leu Met Ser Leu Val Phe Asp Pro Asp Thr His Arg
    370                 375                 380

Ile Leu Gly Gly Ala Leu Met Ser Lys Tyr Asp Val Ser Gln Ser Ala
385                 390                 395                 400

Asn Thr Leu Ser Val Cys Ile Gln Asn Glu Thr Ile Asp Asp Leu
                405                 410                 415

Ala Met Val Asp Met Leu Phe Gln Pro Asn Phe Asp Arg Pro Phe Asn
            420                 425                 430

Tyr Leu Asn Ile Leu Ala Gln Ala Gln Ala Lys Val Ala Gln Ser
        435                 440                 445

Val Asn Ala
    450

<210> SEQ ID NO 21
<211> LENGTH: 550
<212> TYPE: DNA
<213> ORGANISM: Artificial Sequence
<220> FEATURE:
<223> OTHER INFORMATION: Synthetic pENO2

<400> SEQUENCE: 21
cgctcagcat ctgcttcttc ccaaagatga acgcggcgtt atgtcactaa cgacgtgcac      60
caacttgcgg aaagtggaat cccgttccaa aactggcatc cactaattga tacatctaca     120
```

```
caccgcacgc cttttttctg aagcccactt tcgtggactt tgccatatgc aaaattcatg    180
aagtgtgata ccaagtcagc atacacctca ctagggtagt ttctttggtt gtattgatca    240
tttggttcat cgtggttcat taatttttt tctccattgc tttctggctt tgatcttact     300
atcatttgga ttttgtcga aggttgtaga attgtatgtg acaagtggca ccaagcatat     360
ataaaaaaaa aaagcattat cttcctacca gagttgattg ttaaaaacgt atttatagca    420
aacgcaattg taattaattc ttattttgta tcttttcttc ccttgtctca atctttatt    480 tttattttat ttttctttc ttagtttctt tcataacacc aagcaactaa tactataaca    540
tacaataata                                                            550

<210> SEQ ID NO 22
<211> LENGTH: 419
<212> TYPE: DNA
<213> ORGANISM: Artificial Sequence
<220> FEATURE:
<223> OTHER INFORMATION: Synthetic pTEF2.Kl

<400> SEQUENCE: 22
ctctctcgca ataacaatga acactgggtc aatcatagcc tacacaggtg aacagagtag    60
cgtttataca gggtttatac ggtgattcct acggcaaaaa ttttcatt ctaaaaaaaa      120 aaagaaaaat ttttctttcc aacgctagaa ggaaagaaa aatctaatta aattgatttg    180 gtgatttct gagagttccc ttttcatat atcgaatttt gaatataaaa ggagatcgaa    240 aaaattttc tattcaatct gttttctggt tttatttgat agttttttg tgtattatta    300 ttatggatta gtactggttt atgggtttt ttctgtataa cttcttttta ttttagtttg    360
tttaatctta ttttgagtta cattatagtt ccctaactgc aagagaagta acattaaaa    419

<210> SEQ ID NO 23
<211> LENGTH: 598
<212> TYPE: DNA
<213> ORGANISM: Artificial Sequence
<220> FEATURE:
<223> OTHER INFORMATION: Synthetic pTEF3

<400> SEQUENCE: 23
ggctgataat agcgtataaa caatgcatac tttgtacgtt caaaatacaa tgcagtagat    60
atatttatgc atattacata taatacatat cacataggaa gcaacaggcg cgttggactt    120
ttaattttcg aggaccgcga atccttacat cacacccaat cccccacaag tgatccccca    180
cacaccatag cttcaaaatg tttctactcc ttttttactc ttccagattt tctcggactc    240
cgcgcatcgc cgtaccactt caaaacaccc aagcacagca tactaaattt cccctctttc    300
ttcctctagg gtgtcgttaa ttacccgtac taaaggtttg gaaagaaaaa aagagaccgc    360
ctcgtttctt tttcttcgtc gaaaaaggca ataaaaattt ttatcacgtt ctttttcttt    420
gaaaattttt ttttttgatt tttttctctt tcgatgacct cccattgata tttaagttaa    480
taaacggtct tcaatttctc aagtttcagt ttcattttc ttgttctatt acaacttttt    540
ttacttcttg ctcattagaa agaaagcata gcaatctaat ctaagtttta attacaaa     598

<210> SEQ ID NO 24
<211> LENGTH: 700
<212> TYPE: DNA
<213> ORGANISM: Artificial Sequence
<220> FEATURE:
<223> OTHER INFORMATION: Synthetic pADH1

<400> SEQUENCE: 24
```

```
gggtgtacaa tatggacttc ctcttttctg gcaaccaaac ccatacatcg ggattcctat      60
aataccttcg ttggtctccc taacatgtag gtggcggagg ggagatatac aatagaacag     120
ataccagaca agacataatg ggctaaacaa gactacacca attacactgc ctcattgatg     180
gtggtacata acgaactaat actgtagccc tagacttgat agccatcatc atatcgaagt     240
ttcactaccc tttttccatt tgccatctat tgaagtaata ataggcgcat gcaacttctt     300
ttcttttttt ttcttttctc tctcccccgt tgttgtctca ccatatccgc aatgacaaaa     360
aaatgatgga agacactaaa ggaaaaaatt aacgacaaag acagcaccaa cagatgtcgt     420
tgttccagag ctgatgaggg gtatctcgaa gcacacgaaa ctttttcctt ccttcattca     480
cgcacactac tctctaatga gcaacggtat acggccttcc ttccagttac ttgaatttga     540
aataaaaaaa agtttgctgt cttgctatca agtataaata gacctgcaat tattaatctt     600
ttgtttcctc gtcattgttc tcgttccctt tcttccttgt ttcttttcct gcacaatatt     660
tcaagctata ccaagcatac aatcaactat ctcatataca                           700

<210> SEQ ID NO 25
<211> LENGTH: 549
<212> TYPE: DNA
<213> ORGANISM: Artificial Sequence
<220> FEATURE:
<223> OTHER INFORMATION: Synthetic pGPM1

<400> SEQUENCE: 25
gccaaacttt tcggttaaca catgcagtga tgcacgcgcg atggtgctaa gttacatata     60
tatatatata tatatatata tatatatata gccatagtga tgtctaagta acctttatgg    120
tatatttctt aatgtggaaa gatactagcg cgcgcaccca cacacaagct tcgtcttttc    180
ttgaagaaaa gaggaagctc gctaaatggg attccacttt ccgttccctg ccagctgatg    240
gaaaaaggtt agtggaacga tgaagaataa aagagagat ccactgaggt gaaatttcag     300
ctgacagcga gtttcatgat cgtgatgaac aatggtaacg agttgtggct gttgccaggg    360
agggtggttc tcaacttta atgtatggcc aaatcgctac ttgggtttgt tatataacaa     420
agaagaaata atgaactgat tctcttcctc cttcttgtcc tttcttaatt ctgttgtaat    480
taccttcctt tgtaattttt tttgtaatta ttcttcttaa taatccaaac aaacacacat    540
attacaata                                                             549

<210> SEQ ID NO 26
<211> LENGTH: 650
<212> TYPE: DNA
<213> ORGANISM: Artificial Sequence
<220> FEATURE:
<223> OTHER INFORMATION: Synthetic pFBA1

<400> SEQUENCE: 26
acgcaagccc taagaaatga ataacaatac tgacagtact aaataattgc ctacttggct     60
tcacatacgt tgcatacgtc gatatagata ataatgataa tgacagcagg attatcgtaa    120
tacgtaatag ttgaaaatct caaaaatgtg tgggtcatta cgtaaataat gataggaatg    180
ggattcttct attttccctt tttccattct agcagccgtc gggaaaacgt ggcatcctct    240
ctttcgggct caattggagt cacgctgccg tgagcatcct ctctttccat atctaacaac    300
tgagcacgta accaatggaa aagcatgagc ttagcgttgc tccaaaaaag tattggatgg    360
ttaataccat ttgtctgttc tcttctgact ttgactcctc aaaaaaaaaa aatctacaat    420
```

```
caacagatcg cttcaattac gccctcacaa aaactttttt ccttcttctt cgcccacgtt    480
aaattttatc cctcatgttg tctaacggat ttctgcactt gatttattat aaaaagacaa    540
agacataata cttctctatc aatttcagtt attgttcttc cttgcgttat tcttctgttc    600
ttcttttcct tttgtcatat ataaccataa ccaagtaata catattcaaa              650

<210> SEQ ID NO 27
<211> LENGTH: 700
<212> TYPE: DNA
<213> ORGANISM: Artificial Sequence
<220> FEATURE:
<223> OTHER INFORMATION: Synthetic pPDC1

<400> SEQUENCE: 27
ttatttacct atctctaaac ttcaacacct tatatcataa ctaatatttc ttgagataag     60
cacactgcac ccataccttc cttaaaaacg tagcttccag ttttttggtgg ttccggcttc   120 cttcccgatt ccgcccgcta aacgcatatt tttgttgcct ggtggcattt gcaaaatgca   180
taacctatgc atttaaaaga ttatgtatgc tcttctgact tttcgtgtga tgaggctcgt   240
ggaaaaaatg aataatttat gaatttgaga caattttgt gttgttacgg tatttactta   300 tggataatc aatcaattga ggattttatg caaatatcgt ttgaatattt ttccgaccct   360
ttgagtactt tcttcataa ttgcataata ttgtccgctg ccccttttc tgttagacgg    420 tgtcttgatc tacttgctat cgttcaacac caccttattt tctaactatt ttttttttag   480
ctcatttgaa tcagcttatg gtgatggcac attttttgcat aaacctagct gtcctcgttg   540
aacataggaa aaaaaaatat ataaacaagg ctctttcact ctccttgcaa tcagatttgg    600
gtttgttccc tttattttca tatttcttgt catattcctt tctcaattat tattttctac    660
tcataacctc acgcaaaata acacagtcaa atcaatcaaa                         700

<210> SEQ ID NO 28
<211> LENGTH: 700
<212> TYPE: DNA
<213> ORGANISM: Artificial Sequence
<220> FEATURE:
<223> OTHER INFORMATION: Synthetic pPGK1

<400> SEQUENCE: 28
gtgagtaagg aaagagtgag gaactatcgc atacctgcat ttaaagatgc cgatttgggc     60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa agaacaaaa ctgaaaaac ccagacacgc    240 tcgacttcct gtcttcctat tgattgcagc ttccaatttc gtcacacaac aaggtcctag   300
cgacggctca caggttttgt aacaagcaat cgaaggttct ggaatggcgg gaaagggttt   360
agtaccacat gctatgatgc ccactgtgat ctccagagca agttcgttc gatcgtactg    420 ttactctctc tctttcaaac agaattgtcc gaatcgtgtg acaacaacag cctgttctca    480
cacactcttt tcttctaacc aagggggtgg tttagtttag tagaacctcg tgaaacttac    540
atttacatat atataaactt gcataaattg gtcaatgcaa gaaatacata tttggtctttt   600 tctaattcgt agtttttcaa gttcttagat gctttcttt tctctttttt acagatcatc    660
aaggaagtaa ttatctactt tttacaacaa atataaaaca                         700

<210> SEQ ID NO 29
<211> LENGTH: 535
```

```
<212> TYPE: DNA
<213> ORGANISM: Artificial Sequence
<220> FEATURE:
<223> OTHER INFORMATION: Synthetic pRPLA1

<400> SEQUENCE: 29
tcaagttgga tactgatctg atctctccgc cctactacca gggaccctca tgattaccgc      60
tcgaatgcga cgtttcctgc ctcataaaac tggcttgaaa atatttattc gctgaacagt     120
agcctagctt ataaaaattt catttaatta atgtaatatg aaaactcaca tgccttctgt     180
ttctaaaatt gtcacagcaa gaaataacat taccatacgt gatcttatta aactctagta     240
tcttgtctaa tacttcattt aaaagaagcc ttaaccctgt agcctcatct atgtctgcta     300
catatcgtga ggtacgaata tcgtaagatg ataccacgca actttgtaat gatttttttt     360
ttttcatttt ttaaagaatg cctttacatg gtatttgaaa aaaatatctt tataaagttt     420
gcgatctctt ctgttctgaa taattttttag taaaagaaat caaaagaata aagaaatagt     480
ccgctttgtc caatacaaca gcttaaaccg attatctcta aaataacaag aagaa          535

<210> SEQ ID NO 30
<211> LENGTH: 383
<212> TYPE: DNA
<213> ORGANISM: Artificial Sequence
<220> FEATURE:
<223> OTHER INFORMATION: Synthetic pTEF1

<400> SEQUENCE: 30
gtttagcttg cctcgtcccc gccgggtcac ccggccagcg acatggaggc ccagaatacc      60
ctccttgaca gtcttgacgt gcgcagctca ggggcatgat gtgactgtcg cccgtacatt     120
tagcccatac atccccatgt ataatcattt gcatccatac attttgatgg ccgcacggcg     180
cgaagcaaaa attacggctc ctcgctgcag acctgcgagc agggaaacgc tcccctcaca     240
gacgcgttga attgtcccca cgccgcgccc ctgtagagaa atataaaagg ttaggatttg     300
ccactgaggt tcttctttca tatacttcct tttaaaatct tgctacgata cagttctcac     360
atcacatccg aacataaaca acc                                             383

<210> SEQ ID NO 31
<211> LENGTH: 574
<212> TYPE: DNA
<213> ORGANISM: Artificial Sequence
<220> FEATURE:
<223> OTHER INFORMATION: Synthetic pTDH3

<400> SEQUENCE: 31
ctgctgtaac ccgtacatgc ccaaaatagg gggcgggtta cacagaatat ataacatcgt      60
aggtgtctgg gtgaacagtt tattcctggc atccactaaa tataatggag cccgcttttt     120
aagctggcat ccagaaaaaa aaagaatccc agcaccaaaa tattgttttc ttcaccaacc     180
atcagttcat aggtccattc tcttagcgca actacagaga acaggggcac aaacaggcaa     240
aaaacgggca caacctcaat ggagtgatgc aacctgcctg gagtaaatga tgacacaagg     300
caattgaccc acgcatgtat ctatctcatt ttcttacacc ttctattacc ttctgctctc     360
tctgatttgg aaaaagctga aaaaaaaggt tgaaaccagt tccctgaaat tattccccta     420
cttgactaat aagtatataa agacggtagg tattgattgt aattctgtaa atctatttct     480
taaacttctt aaattctact tttatagtta gtcttttttt tagttttaaa acaccaagaa     540
cttagtttcg aataaacaca cataaacaaa caaa                                 574
```

<210> SEQ ID NO 32
<211> LENGTH: 300
<212> TYPE: DNA
<213> ORGANISM: Artificial Sequence
<220> FEATURE:
<223> OTHER INFORMATION: Synthetic tTHD2

<400> SEQUENCE: 32

```
atttaactcc ttaagttact ttaatgattt agtttttatt attaataatt catgctcatg    60
acatctcata tacacgttta taaaacttaa atagattgaa aatgtattaa agattcctca   120
gggattcgat ttttttggaa gttttttgttt tttttttcctt gagatgctgt agtatttggg   180
aacaattata caatcgaaag atatatgctt acattcgacc gttttagccg tgatcattat   240
cctatagtaa cataacctga agcataactg acactactat catcaatact tgtcacatga   300
```

<210> SEQ ID NO 33
<211> LENGTH: 300
<212> TYPE: DNA
<213> ORGANISM: Artificial Sequence
<220> FEATURE:
<223> OTHER INFORMATION: Synthetic tCYC1

<400> SEQUENCE: 33

```
acaggcccct tttcctttgt cgatatcatg taattagtta tgtcacgctt acattcacgc    60
cctcctccca catccgctct aaccgaaaag gaaggagtta gacaacctga agtctaggtc   120
cctatttatt ttttttaata gttatgttag tattaagaac gttatttata tttcaaattt   180
ttcttttttt tctgtacaaa cgcgtgtacg catgtaacat tatactgaaa accttgcttg   240
agaaggtttt gggacgctcg aaggctttaa tttgcaagct tcgcagttta cactctcatc   300
```

<210> SEQ ID NO 34
<211> LENGTH: 300
<212> TYPE: DNA
<213> ORGANISM: Artificial Sequence
<220> FEATURE:
<223> OTHER INFORMATION: Synthetic tTDH3

<400> SEQUENCE: 34

```
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt ctttttcgcc acatgtaata tctgtagtag   180
atacctgata cattgtggat gctgagtgaa attttagtta ataatggagg cgctcttaat   240
aattttgggg atattggctt ttttttttaa agtttacaaa tgaattttttt ccgccaggat   300
```

<210> SEQ ID NO 35
<211> LENGTH: 354
<212> TYPE: DNA
<213> ORGANISM: Artificial Sequence
<220> FEATURE:
<223> OTHER INFORMATION: Synthetic tADH1

<400> SEQUENCE: 35

```
actagttcta gagcggccgc caccgcggtg ggcgaatttc ttatgattta tgatttttat    60
tattaaataa gttataaaaa aaataagtgt atacaaattt taaagtgact cttaggtttt   120
aaaacgaaaa ttcttattct tgagtaactc tttcctgtag gtcaggttgc tttctcaggt   180
atagcatgag gtcgctctta ttgaccacac ctctaccggc atgccgagca aatgcctgca   240
aatcgctccc catttcaccc aattgtagat atgctaactc cagcaatgag ttgatgaatc   300
```

```
tcggtgtgta ttttatgtcc tcagaggaca acacctgttg taatcgttct tcca        354
```

<210> SEQ ID NO 36
<211> LENGTH: 299
<212> TYPE: DNA
<213> ORGANISM: Artificial Sequence
<220> FEATURE:
<223> OTHER INFORMATION: Synthetic tTPI1

<400> SEQUENCE: 36

```
gattaatata attatataaa aatattatct tcttttcttt atatctagtg ttatgtaaaa   60
taaattgatg actacggaaa gcttttttat attgtttctt tttcattctg agccacttaa  120
atttcgtgaa tgttcttgta agggacggta gatttacaag tgatacaaca aaaagcaagg  180
cgcttttttct aataaaaaga agaaaagcat ttaacaattg aacacctcta tatcaacgaa  240
gaatattact ttgtctctaa atccttgtaa aatgtgtacg atctctatat gggttactc    299
```

<210> SEQ ID NO 37
<211> LENGTH: 299
<212> TYPE: DNA
<213> ORGANISM: Artificial Sequence
<220> FEATURE:
<223> OTHER INFORMATION: Synthetic tMET25

<400> SEQUENCE: 37

```
gtgtgcgtaa tgagttgtaa aattatgtat aaacctactt tctctcacaa gtactatact   60
tttataaaac gaactttatt gaatgaata tccttttttt cccttgttac atgtcgtgac   120
tcgtactttg aacctaaatt gttctaacat caaagaacag tgttaattcg cagtcgagaa  180
gaaaaatatg gtgaacaaga ctcatctact tcatgagact actttacgcc tcctataaag  240
ctgtcacact ggataaattt attgtaggac caagttacaa aagaggatga tggaggttt    299
```

<210> SEQ ID NO 38
<211> LENGTH: 305
<212> TYPE: DNA
<213> ORGANISM: Artificial Sequence
<220> FEATURE:
<223> OTHER INFORMATION: Synthetic tENO2

<400> SEQUENCE: 38

```
ggatcctaaa gtgctttaa ctaagaatta ttagtcttt ctgcttattt tttcatcata    60
gtttagaaca ctttatatta acgaatagtt tatgaatcta tttaggttta aaaattgata  120
cagttttata agttactttt tcaaagactc gtgctgtcta ttgcataatg cactggaagg  180
ggaaaaaaaa ggtgcacacg cgtggctttt tcttgaattt gcagtttgaa aaataactac  240
atggatgata agaaaacatg gagtacagtc actttgagaa ccttcaatca gctggtaacg  300
tcttc                                                              305
```

<210> SEQ ID NO 39
<211> LENGTH: 300
<212> TYPE: DNA
<213> ORGANISM: Artificial Sequence
<220> FEATURE:
<223> OTHER INFORMATION: Synthetic tMET3

<400> SEQUENCE: 39

```
tcgtcataaa atgctcccat ctcaaaagta gggcaaaatt catgatcgac cgcgcaaaat   60
aaatagattt gcaaataagt tttgtatgta catttattaa tatatataat atatcaaaag  120
```

| | |
|---|---|
| aaaaaaatca aaaaaaaaaa aaaaaaaaaa ttgcactctt attcagtcat caattacaaa | 180 |
| acctagagat agcgatggtg catattcaat aaaaaactcc ttatactgtc gagaaagctt | 240 |
| attattggta cttctcgaag atactaaaaa aggttaattt ttggagacgg aggcaatagc | 300 |

<210> SEQ ID NO 40
<211> LENGTH: 301
<212> TYPE: DNA
<213> ORGANISM: Artificial Sequence
<220> FEATURE:
<223> OTHER INFORMATION: Synthetic tPGK1

<400> SEQUENCE: 40

| | |
|---|---|
| attgaattga attgaaatcg atagatcaat ttttttcttt tctctttccc catcctttac | 60 |
| gctaaaataa tagtttattt tatttttga atatttttta tttatatacg tatatataga | 120 |
| ctattattta tcttttaatg attattaaga ttttattaa aaaaaaattc gctcctcttt | 180 |
| taatgccttt atgcagtttt tttttcccat tcgatatttc tatgttcggg ttcagcgtat | 240 |
| tttaagttta ataactcgaa aattctgcgt tcgttaaagc tttcgagaag gatattattt | 300 |
| a | 301 |

<210> SEQ ID NO 41
<211> LENGTH: 700
<212> TYPE: DNA
<213> ORGANISM: Artificial Sequence
<220> FEATURE:
<223> OTHER INFORMATION: Synthetic pPYK1

<400> SEQUENCE: 41

| | |
|---|---|
| aaaaggaaag attattgaaa gagaaagaaa gaaaaaaaaa aaatgtacac ccagacatcg | 60 |
| ggcttccaca atttcggctc tattgttttc catctctcgc aacggcggga ttcctctatg | 120 |
| gcgtgtgatg tctgtatctg ttacttaatc cagaaactgg cacttgaccc aactctgcca | 180 |
| cgtgggtcgt tttgccatcg acagattggg agattttcat agtagaattc agcatgatag | 240 |
| ctacgtaaat gtgttccgca ccgtcacaaa gtgttttcta ctgttctttc ttctttcgtt | 300 |
| cattcagttg agttgagtga gtgctttgtt caatggatct tagctaaaat gcatattttt | 360 |
| tctcttggta aatgaatgct tgtgatgtct tccaagtgat ttcctttcct tcccatatga | 420 |
| tgctaggtac cttagtgtc ttcctaaaaa aaaaaaagg ctcgccatca aaacgatatt | 480 |
| cgttggcttt tttttctgaa ttataaatac tctttggtaa cttttcattt ccaagaacct | 540 |
| cttttttcca gttatatcat ggtccccttt caaagttatt ctctactctt tttcatattc | 600 |
| attctttttc atcctttggt tttttattct taacttgttt attattctct cttgtttcta | 660 |
| tttacaagac accaatcaaa acaaataaaa catcatcaca | 700 |

<210> SEQ ID NO 42
<211> LENGTH: 500
<212> TYPE: DNA
<213> ORGANISM: Artificial Sequence
<220> FEATURE:
<223> OTHER INFORMATION: Synthetic pTPI1

<400> SEQUENCE: 42

| | |
|---|---|
| atttaaactg tgaggacctt aatacattca gacacttctg cggtatcacc ctacttattc | 60 |
| ccttcgagat tatatctagg aacccatcag gttggtggaa gattacccgt tctaagactt | 120 |
| ttcagcttcc tctattgatg ttacacctgg acacccctt tctggcatcc agttttaat | 180 |
| cttcagtggc atgtgagatt ctccgaaatt aattaaagca atcacacaat tctctcggat | 240 |

```
accacctcgg ttgaaactga caggtggttt gttacgcatg ctaatgcaaa ggagcctata    300
tacctttggc tcggctgctg taacagggaa tataaagggc agcataattt aggagtttag    360
tgaacttgca acatttacta ttttcccttc ttacgtaaat attttctttt ttaattctaa    420
atcaatcttt ttcaattttt tgtttgtatt cttttcttgc ttaaatctat aactacaaaa    480
aacacataca taaactaaaa                                                500

<210> SEQ ID NO 43
<211> LENGTH: 300
<212> TYPE: DNA
<213> ORGANISM: Artificial Sequence
<220> FEATURE:
<223> OTHER INFORMATION: Synthetic tDIT1

<400> SEQUENCE: 43
taaagtaaga gcgctacatt ggtctacctt tttgttcttt tacttaaaca ttagttagtt     60
cgttttcttt ttctcatttt tttatgtttc cccccaaag ttctgatttt ataatatttt    120
atttcacaca attccattta acagaggggg aatagattct ttagcttaga aaattagtga    180
tcaatatata tttgcctttc ttttcatctt ttcagtgata ttaatggttt cgagacactg    240
caatggccct agttgtctaa gaggatagat gttactgtca aagatgatat tttgaatttc    300

<210> SEQ ID NO 44
<211> LENGTH: 33
<212> TYPE: DNA
<213> ORGANISM: Artificial Sequence
<220> FEATURE:
<223> OTHER INFORMATION: Synthetic loxP

<400> SEQUENCE: 44
ataacttcgt ataatgtatg ctatacgaag tta                                   33

<210> SEQ ID NO 45
<211> LENGTH: 2085
<212> TYPE: DNA
<213> ORGANISM: Artificial Sequence
<220> FEATURE:
<223> OTHER INFORMATION: Synthetic nucleic acid HAA-1

<400> SEQUENCE: 45
atggtcttga taaatggcat aaagtatgcc tgtgagaggt gcataagagg ccatagagta     60
acaacatgca atcatacaga tcaaccgctt atgatgatca aacccaaagg tagaccttcc    120
actacatgcg actattgtaa acaacttcga aaaacaaga atgcaaatcc tgaaggtgtt    180
tgcacgtgtg gccggctaga gaagaaaaaa ctggcacaga aagccaaaga agaagcaaga    240
gctaaagcca agaaaaaca agaaaaacag tgtacctgcg ggactgatga ggtttgcaaa    300
tatcatgctc aaaagagaca tctaagaaag tccccttcaa gttctcaaaa gaaaggaaga    360
tccatttctc gttctcaacc aatgtttgaa agggtattgt cttctacttc acttgacagc    420
aatatgttat ccggccacgg agcactatca gatacctcta gcatactgac gagcacattt    480
ttagacagtg agccgggtgt tggtaaaatt caaaagatt accatcatgt cccttcattg    540
gcctccattt catccttaca atcctcgcaa tcgttagatc aaaatttcag tataccacaa    600
agcccgccgt tatcttcaat gtcatttaat tttctcacgg gaaatatcaa tgaaaccaac    660
caaaatcaca gtaatcatca gcattcaaaa tcaggcaata actggcaaga tagttcggta    720
agcttgccag cgaaagctga ttcacgtctt aacatgatgg ataaaaacaa ctctgtgggt    780
```

```
cttgacctat taggccattc aaaacgaata tcgccgatat caaactctcg tgtgggcgaa    840
gttagcgttc cgctagaaga atatattcct tctgacattg atggggttgg aagagttact   900
gataaaagct ctttggtcta cgattggcca tttgatgaaa gtattgagag aaatttcagt   960
acaaccgcaa ccgctgcaac tggtgaaagt aagttcgaca ttaacgacaa ctgtaataga  1020
attaatagca aaagttatag taagactaat agtatgaatg gaaacggtat gaacaatagc  1080
aataataata atatcaacag taatggcaac gacaagaaca ataacaactc ttctagacaa  1140
gaacatcaag gaaatggact atttgacatg tttacagatt catcgtcgat ttcaacgctt  1200
tcccgtgcaa acttattatt gcaagaaaaa attggttcgc aagaaaactc tgtcaaacaa  1260
gaaaactatt cgaaaaatcc tcaacttcgt catcaattaa cttccagaag tagatcattt  1320
attcatcatc cggcaaacga gtatttgaag aatacttttg gaaattcaca tagtaatgac  1380
atcggaaagg gagttgaagt gctatctttg acaccgagtt ttatggatat tcccgaaaaa  1440
gaaagagaaa cggaaagatc gccatcatcc aattacatta ctgacagacc tttcactcga  1500
aaacctagat cttctagcat tgacgtaaac ataggtatcc cacctatggc accaacaacc  1560
gtagcgacat ctcccggtgc attgaacaat gccgtagcaa gcaatctcga cgatcaactg  1620
agtttaacat cactaaactc tcagccatca tcgatagcaa atatgatgat ggacccttca  1680
aacctagctg agcaaagttc tattcattca gttcctcagt caataaactc tccgagaatg  1740
cctaaaactg gaagtcgcca agacaagaac attcacacta agaaggaaga agaaatccg   1800 ctaaataaca tacacgatct gtcacaattg gaaaatgtac cagacgagat gaaccaaatg  1860
ttctccccac cattaaaaag tatgaataga ccggatgcca taaggaaaaa ttcatctagt  1920
agtaatttca taatccaagg aaatagcatg atctctacgc cttccggaag gaatgacctt  1980
ccagatacct ctccaatgag tagtattcaa acagcgtcac caccaagtca attactgacc  2040
gatcaaggat ttgcggattt ggataatttc atgtcttcgt tatga                  2085
```

<210> SEQ ID NO 46
<211> LENGTH: 694
<212> TYPE: PRT
<213> ORGANISM: Artificial Sequence
<220> FEATURE:
<223> OTHER INFORMATION: Synthetic amino acid HAA-1

<400> SEQUENCE: 46

```
Met Val Leu Ile Asn Gly Ile Lys Tyr Ala Cys Glu Arg Cys Ile Arg
1               5                   10                  15

Gly His Arg Val Thr Thr Cys Asn His Thr Asp Gln Pro Leu Met Met
            20                  25                  30

Ile Lys Pro Lys Gly Arg Pro Ser Thr Thr Cys Asp Tyr Cys Lys Gln
        35                  40                  45

Leu Arg Lys Asn Lys Asn Ala Asn Pro Glu Gly Val Cys Thr Cys Gly
    50                  55                  60

Arg Leu Glu Lys Lys Leu Ala Gln Lys Ala Lys Glu Glu Ala Arg
65                  70                  75                  80

Ala Lys Ala Lys Glu Lys Gln Arg Lys Gln Cys Thr Cys Gly Thr Asp
                85                  90                  95

Glu Val Cys Lys Tyr His Ala Gln Lys Arg His Leu Arg Lys Ser Pro
            100                 105                 110

Ser Ser Ser Gln Lys Lys Gly Arg Ser Ile Ser Arg Ser Gln Pro Met
        115                 120                 125

Phe Glu Arg Val Leu Ser Ser Thr Ser Leu Asp Ser Asn Met Leu Ser
```

```
            130                 135                 140
Gly His Gly Ala Leu Ser Asp Thr Ser Ser Ile Leu Thr Ser Thr Phe
145                 150                 155                 160

Leu Asp Ser Glu Pro Gly Val Gly Lys Ile Ser Lys Asp Tyr His His
                165                 170                 175

Val Pro Ser Leu Ala Ser Ile Ser Ser Leu Gln Ser Ser Gln Ser Leu
                180                 185                 190

Asp Gln Asn Phe Ser Ile Pro Gln Ser Pro Leu Ser Ser Met Ser
            195                 200                 205

Phe Asn Phe Leu Thr Gly Asn Ile Asn Glu Thr Asn Gln Asn His Ser
        210                 215                 220

Asn His Gln His Ser Lys Ser Gly Asn Asn Trp Gln Asp Ser Ser Val
225                 230                 235                 240

Ser Leu Pro Ala Lys Ala Asp Ser Arg Leu Asn Met Met Asp Lys Asn
                245                 250                 255

Asn Ser Val Gly Leu Asp Leu Leu Gly His Ser Lys Arg Ile Ser Pro
                260                 265                 270

Ile Ser Asn Ser Arg Val Gly Glu Val Ser Val Pro Leu Glu Glu Tyr
            275                 280                 285

Ile Pro Ser Asp Ile Asp Gly Val Gly Arg Val Thr Asp Lys Ser Ser
        290                 295                 300

Leu Val Tyr Asp Trp Pro Phe Asp Glu Ser Ile Glu Arg Asn Phe Ser
305                 310                 315                 320

Thr Thr Ala Thr Ala Ala Thr Gly Glu Ser Lys Phe Asp Ile Asn Asp
                325                 330                 335

Asn Cys Asn Arg Ile Asn Ser Lys Ser Tyr Ser Lys Thr Asn Ser Met
                340                 345                 350

Asn Gly Asn Gly Met Asn Ser Asn Asn Asn Ile Asn Ser Asn
            355                 360                 365

Gly Asn Asp Lys Asn Asn Asn Ser Ser Arg Gln Glu His Gln Gly
        370                 375                 380

Asn Gly Leu Phe Asp Met Phe Thr Asp Ser Ser Ser Ile Ser Thr Leu
385                 390                 395                 400

Ser Arg Ala Asn Leu Leu Leu Gln Glu Lys Ile Gly Ser Gln Glu Asn
                405                 410                 415

Ser Val Lys Gln Glu Asn Tyr Ser Lys Asn Pro Gln Leu Arg His Gln
            420                 425                 430

Leu Thr Ser Arg Ser Arg Ser Phe Ile His His Pro Ala Asn Glu Tyr
        435                 440                 445

Leu Lys Asn Thr Phe Gly Asn Ser His Ser Asn Asp Ile Gly Lys Gly
        450                 455                 460

Val Glu Val Leu Ser Leu Thr Pro Ser Phe Met Asp Ile Pro Glu Lys
465                 470                 475                 480

Glu Arg Glu Thr Glu Arg Ser Pro Ser Asn Tyr Ile Thr Asp Arg
                485                 490                 495

Pro Phe Thr Arg Lys Pro Arg Ser Ser Ile Asp Val Asn His Arg
            500                 505                 510

Tyr Pro Pro Met Ala Pro Thr Val Ala Thr Ser Pro Gly Ala Leu
        515                 520                 525

Asn Asn Ala Val Ala Ser Asn Leu Asp Asp Gln Leu Ser Leu Thr Ser
        530                 535                 540

Leu Asn Ser Gln Pro Ser Ser Ile Ala Asn Met Met Asp Pro Ser
545                 550                 555                 560
```

```
Asn Leu Ala Glu Gln Ser Ser Ile His Ser Val Pro Gln Ser Ile Asn
                565                 570                 575

Ser Pro Arg Met Pro Lys Thr Gly Ser Arg Gln Asp Lys Asn Ile His
            580                 585                 590

Thr Lys Lys Glu Glu Arg Asn Pro Leu Asn Asn Ile His Asp Leu Ser
        595                 600                 605

Gln Leu Glu Asn Val Pro Asp Glu Met Asn Gln Met Phe Ser Pro Pro
    610                 615                 620

Leu Lys Ser Met Asn Arg Pro Asp Ala Ile Arg Glu Asn Ser Ser Ser
625                 630                 635                 640

Ser Asn Phe Ile Ile Gln Gly Asn Ser Met Ile Ser Thr Pro Ser Gly
            645                 650                 655

Arg Asn Asp Leu Pro Asp Thr Ser Pro Met Ser Ser Ile Gln Thr Ala
        660                 665                 670

Ser Pro Pro Ser Gln Leu Leu Thr Asp Gln Gly Phe Ala Asp Leu Asp
    675                 680                 685

Asn Phe Met Ser Ser Leu
    690

<210> SEQ ID NO 47
<211> LENGTH: 1089
<212> TYPE: DNA
<213> ORGANISM: Artificial Sequence
<220> FEATURE:
<223> OTHER INFORMATION: Synthetic nucleic acids LEU2.Kl

<400> SEQUENCE: 47
atgtctaaga atatcgttgt cctaccgggt gatcacgtcg gtaaagaagt tactgacgaa      60
gctattaagg tcttgaatgc cattgctgaa gtccgtccag aaattaagtt caatttccaa     120
catcacttga tcggggtgc tgccatcgat gccactggca ctcctttacc agatgaagct     180
ctagaagcct ctaagaaagc cgatgctgtc ttactaggtg ctgttggtgg tccaaaatgg     240
ggtacgggcg cagttagacc agaacaaggt ctattgaaga tcagaaagga attgggtcta     300
tacgccaact tgagaccatg taactttgct tctgattctt tactagatct ttctcctttg     360
aagcctgaat atgcaaaggg taccgatttc gtcgtcgtta gagaattggt tggtggtatc     420
tactttggtg aaagaaaaga gatgaaggt gacggagttg cttgggactc tgagaaatac     480
agtgttcctg aagttcaaag aattacaaga atggctgctt cttggcatt gcaacaaaac     540
ccaccattac aatctggtc tcttgacaag gctaacgtgc ttgcctcttc cagattgtgg     600
agaaagactg ttgaagaaac catcaagact gagttcccac aattaactgt tcagcaccaa     660
ttgatcgact ctgctgctat gattttggtt aaatcaccaa ctaagctaaa cggtgttgtt     720
attaccaaca acatgtttgg tgatattatc tccgatgaag cctctgttat tccaggttct     780
ttgggtttat taccttctgc atctctagct tccctacctg acactaacaa ggcattcggt     840
ttgtacgaac catgtcatgg ttctgcccca gatttaccag caaacaaggt taacccaatt     900
gctaccatct tatctgcagc tatgatgttg aagttatcct tggatttggt tgaagaaggt     960
agggctcttg aagaagctgt tagaaatgtc ttggatgcag tgtcagaaac cggtgacctt    1020
ggtggttcta actctaccac tgaggttggc gatgctatcg ccaaggctgt caaggaaatc    1080
ttggcttaa                                                             1089

<210> SEQ ID NO 48
<211> LENGTH: 362
```

<212> TYPE: PRT
<213> ORGANISM: Artificial Sequence
<220> FEATURE:
<223> OTHER INFORMATION: Synthetic amino acid LEU2.Kl

<400> SEQUENCE: 48

```
Met Ser Lys Asn Ile Val Val Leu Pro Gly Asp His Val Gly Lys Glu
1               5                   10                  15
Val Thr Asp Glu Ala Ile Lys Val Leu Asn Ala Ile Ala Glu Val Arg
            20                  25                  30
Pro Glu Ile Lys Phe Asn Phe Gln His His Leu Ile Gly Gly Ala Ala
        35                  40                  45
Ile Asp Ala Thr Gly Thr Pro Leu Pro Asp Glu Ala Leu Glu Ala Ser
    50                  55                  60
Lys Lys Ala Asp Ala Val Leu Leu Gly Ala Val Gly Gly Pro Lys Trp
65                  70                  75                  80
Gly Thr Gly Ala Val Arg Pro Glu Gln Gly Leu Leu Lys Ile Arg Lys
                85                  90                  95
Glu Leu Gly Leu Tyr Ala Asn Leu Arg Pro Cys Asn Phe Ala Ser Asp
            100                 105                 110
Ser Leu Leu Asp Leu Ser Pro Leu Lys Pro Glu Tyr Ala Lys Gly Thr
        115                 120                 125
Asp Phe Val Val Val Arg Glu Leu Val Gly Gly Ile Tyr Phe Gly Glu
    130                 135                 140
Arg Lys Glu Asp Glu Gly Asp Gly Val Ala Trp Asp Ser Glu Lys Tyr
145                 150                 155                 160
Ser Val Pro Glu Val Gln Arg Ile Thr Arg Met Ala Ala Phe Leu Ala
                165                 170                 175
Leu Gln Gln Asn Pro Pro Leu Pro Ile Trp Ser Leu Asp Lys Ala Asn
            180                 185                 190
Val Leu Ala Ser Ser Arg Leu Trp Arg Lys Thr Val Glu Glu Thr Ile
        195                 200                 205
Lys Thr Glu Phe Pro Gln Leu Thr Val Gln His Gln Leu Ile Asp Ser
    210                 215                 220
Ala Ala Met Ile Leu Val Lys Ser Pro Thr Lys Leu Asn Gly Val Val
225                 230                 235                 240
Ile Thr Asn Asn Met Phe Gly Asp Ile Ile Ser Asp Glu Ala Ser Val
                245                 250                 255
Ile Pro Gly Ser Leu Gly Leu Leu Pro Ser Ala Ser Leu Ala Ser Leu
            260                 265                 270
Pro Asp Thr Asn Lys Ala Phe Gly Leu Tyr Glu Pro Cys His Gly Ser
        275                 280                 285
Ala Pro Asp Leu Pro Ala Asn Lys Val Asn Pro Ile Ala Thr Ile Leu
    290                 295                 300
Ser Ala Ala Met Met Leu Lys Leu Ser Leu Asp Leu Val Glu Glu Gly
305                 310                 315                 320
Arg Ala Leu Glu Glu Ala Val Arg Asn Val Leu Asp Ala Gly Val Arg
                325                 330                 335
Thr Gly Asp Leu Gly Gly Ser Asn Ser Thr Thr Glu Val Gly Asp Ala
            340                 345                 350
Ile Ala Lys Ala Val Lys Glu Ile Leu Ala
        355                 360
```

<210> SEQ ID NO 49
<211> LENGTH: 654

<212> TYPE: DNA
<213> ORGANISM: Artificial Sequence
<220> FEATURE:
<223> OTHER INFORMATION: Synthetic nucleic acid His 5

<400> SEQUENCE: 49

```
atgggtagga gggcttttgt agaaagaaat acgaacgaaa cgaaaatcag cgttgccatc      60
gctttggaca aagctcccttt acctgaagag tcgaattttta ttgatgaact tataacttcc    120
aagcatgcaa accaaaaggg agaacaagta atccaagtag acacgggaat tggattcttg     180
gatcacatgt atcatgcact ggctaaacat gcaggctgga gcttacgact ttactcaaga     240
ggtgatttaa tcatcgatga tcatcacact gcagaagata ctgctattgc acttggtatt     300
gcattcaagc aggctatggg taactttgcc ggcgttaaaa gatttggaca tgcttattgt     360
ccacttgacg aagctctttc tagaagcgta gttgacttgt cgggacggcc ctatgctgtt     420
atcgatttgg gattaaagcg tgaaaaggtt ggggaattgt cctgtgaaat gatccctcac     480
ttactatatt cctttcggt agcagctgga attactttgc atgttacctg cttatatggt      540
agtaatgacc atcatcgtgc tgaaagcgct tttaaatctc tggctgttgc catgcgcgcg     600
gctactagtc ttactggaag ttctgaagtc ccaagcacga agggagtgtt gtaa           654
```

<210> SEQ ID NO 50
<211> LENGTH: 217
<212> TYPE: PRT
<213> ORGANISM: Artificial Sequence
<220> FEATURE:
<223> OTHER INFORMATION: Synthetic amino acid His 5

<400> SEQUENCE: 50

```
Met Gly Arg Arg Ala Phe Val Glu Arg Asn Thr Asn Glu Thr Lys Ile
1               5                   10                  15

Ser Val Ala Ile Ala Leu Asp Lys Ala Pro Leu Pro Glu Glu Ser Asn
            20                  25                  30

Phe Ile Asp Glu Leu Ile Thr Ser Lys His Ala Asn Gln Lys Gly Glu
        35                  40                  45

Gln Val Ile Gln Val Asp Thr Gly Ile Gly Phe Leu Asp His Met Tyr
    50                  55                  60

His Ala Leu Ala Lys His Ala Gly Trp Ser Leu Arg Leu Tyr Ser Arg
65                  70                  75                  80

Gly Asp Leu Ile Ile Asp Asp His His Thr Ala Glu Asp Thr Ala Ile
                85                  90                  95

Ala Leu Gly Ile Ala Phe Lys Gln Ala Met Gly Asn Phe Ala Gly Val
            100                 105                 110

Lys Arg Phe Gly His Ala Tyr Cys Pro Leu Asp Glu Ala Leu Ser Arg
        115                 120                 125

Ser Val Val Asp Leu Ser Gly Arg Pro Tyr Ala Val Ile Asp Leu Gly
    130                 135                 140

Leu Lys Arg Glu Lys Val Gly Glu Leu Ser Cys Glu Met Ile Pro His
145                 150                 155                 160

Leu Leu Tyr Ser Phe Ser Val Ala Ala Gly Ile Thr Leu His Val Thr
                165                 170                 175

Cys Leu Tyr Gly Ser Asn Asp His His Arg Ala Glu Ser Ala Phe Lys
            180                 185                 190

Ser Leu Ala Val Ala Met Arg Ala Ala Thr Ser Leu Thr Gly Ser Ser
        195                 200                 205

Glu Val Pro Ser Thr Lys Gly Val Leu
```

<210> SEQ ID NO 51
<211> LENGTH: 633
<212> TYPE: DNA
<213> ORGANISM: Artificial Sequence
<220> FEATURE:
<223> OTHER INFORMATION: Synthetic nucleic acid Trp1 kl

<400> SEQUENCE: 51

```
atgctcgtta aagtgtgtgg tttgcaaacc gttgaagctg caaagactgc tgtggatgat      60
ggtgctgatt acttaggtat catttgtgtt cccggtagga aaagaaccat tgactcatct     120
gttgcgaaag gtatttcaac tgcagttcac caacaagaga acgtgaaagg tactaaacta     180
gtcggggtgt ttagaaatca gtccgttgat gatgtccttc aactgtacca cgaatataat     240
ctagatgtga tacaattaca tggagatgaa gatattaaag aatacagatc tttgatccca     300
tcttcaattc caatcattaa gaggttccag ttcccacagg attgtgaatt actactggac     360
ctgtatgaac acgtagacaa tgtgctgacg ttgttcgatt ctggtgaagg tggcactggt     420
gagaaattga attggagtgc aatttccagt tggtctgcaa gtcatcccga gataaaattc     480
attatcgctg gtggattgaa tcctgataac gtttctgttg ccattaatat gttaccaaat     540
gcgatcggtg tcgatgtaag tggaggagta gagactgatg gtatcaagga tttagaaaag     600
gtaaagctat tcatccagca ggcctctcaa tag                                  633
```

<210> SEQ ID NO 52
<211> LENGTH: 210
<212> TYPE: PRT
<213> ORGANISM: Artificial Sequence
<220> FEATURE:
<223> OTHER INFORMATION: Synthetic amino acid Trp1 Kl

<400> SEQUENCE: 52

```
Met Leu Val Lys Val Cys Gly Leu Gln Thr Val Glu Ala Ala Lys Thr
1               5                   10                  15

Ala Val Asp Asp Gly Ala Asp Tyr Leu Gly Ile Ile Cys Val Pro Gly
            20                  25                  30

Arg Lys Arg Thr Ile Asp Ser Ser Val Ala Lys Gly Ile Ser Thr Ala
        35                  40                  45

Val His Gln Gln Glu Asn Val Lys Gly Thr Lys Leu Val Gly Val Phe
    50                  55                  60

Arg Asn Gln Ser Val Asp Asp Val Leu Gln Leu Tyr His Glu Tyr Asn
65                  70                  75                  80

Leu Asp Val Ile Gln Leu His Gly Asp Glu Asp Ile Lys Glu Tyr Arg
                85                  90                  95

Ser Leu Ile Pro Ser Ser Ile Pro Ile Ile Lys Arg Phe Gln Phe Pro
            100                 105                 110

Gln Asp Cys Glu Leu Leu Leu Asp Leu Tyr Glu His Val Asp Asn Val
        115                 120                 125

Leu Thr Leu Phe Asp Ser Gly Glu Gly Gly Thr Gly Glu Lys Leu Asn
    130                 135                 140

Trp Ser Ala Ile Ser Ser Trp Ser Ala Ser His Pro Glu Ile Lys Phe
145                 150                 155                 160

Ile Ile Ala Gly Gly Leu Asn Pro Asp Asn Val Ser Val Ala Ile Asn
                165                 170                 175

Met Leu Pro Asn Ala Ile Gly Val Asp Val Ser Gly Gly Val Glu Thr
            180                 185                 190
```

```
Asp Gly Ile Lys Asp Leu Glu Lys Val Lys Leu Phe Ile Gln Gln Ala
        195                 200                 205
Ser Gln
    210
```

METHOD FOR PRODUCING ACETOIN

FIELD OF THE INVENTION

The present invention relates to microorganism having an improved acetoin pathway. The recombinant microorganism is modified to improve the production of acetoin compared to the unmodified microorganism. The invention also provides methods for using such microorganism to produce acetoin.

BACKGROUND OF THE INVENTION

Acetoin, also known as 3-hydroxybutanone or acetyl methyl carbinol, is formed in bacteria from pyruvate by action of the two enzymes, namely α-acetolactate synthase, that catalyzes the condensation of two pyruvate molecules with a single decarboxylation to afford α-acetolactate, and α-acetolactate decarboxylase that decarboxylates this last one to acetoin (Juni, 1952).

Acetoin is a flavor commonly used in the food industry where it replaces diacetyl because it is regarded as safer (Huang, 2011). Acetoin is used as a flavor ingredient in formulations for raspberry, strawberry, vanilla, walnut, rum, butter, butterscotch, caramel, coconut, coffee and fruit flavors. Acetoin may be added to alcoholic and nonalcoholic beverages such as cream soda. Its buttery flavor is well suited for ice cream, ices, candy, baked goods, margarine, gelatin desserts, cottage cheese, margarine and shortenings. Acetoin is also used by the cosmetic industry in perfumes, and fragrances as an aroma carrier. Finally, acetoin is one of the top chemical additives in cigarettes and as a flavor agent in electronic cigarettes. Acetoin is furthermore a precursor of Methyl Vinyl Ketone (MVK) which is a useful intermediate for chemistry.

The traditional chemical synthesis of acetoin is faced the drawback of the petroleum deficiency and environmental pollution, whereas the market for acetoin as a food flavor is currently still growing by an annual rate of 5 to 5.5%, and expected to reach $14 billion in 2018. The fragrance market is expected exceed $16 billion in 2018.

Many chemicals that could only be produced by traditional chemical processes in the past can now have the potential to be generated biologically, using renewable resources (Danner & Braun, 1999; Hatti-Kaul et al., 2007). Microbial production of acetoin is one such example. Interest in this bioprocess has increased remarkably because acetoin has a large number of industrial applications, as above-mentioned, and microbial production will alleviate the dependence on oil supply for the production of platform chemicals. *Saccharomyces cerevisiae* is an especially well suited platform for such bioprocesses (Nielsen 2013) Regarding the microbial production of acetoin, most studies used microorganisms, such as *Candida glabrata, Bacillus subtilis*, to produce acetoin (Shubo Li et al., Microbial Cell Factories 2014, 13:55; Silbersack J et al., Appl Microbiol Biotechnol. 2006 December; 73(4):895-903;

Acetoin production by a GRAS (i.e. generally recognized as safe) microorganism would thus be desirable. Yeast, and more particularly *Saccharomyces cerevisiae*, is an appropriate microorganism in this context. *S. cerevisiae* is known to produce acetoin naturally, but the yield and productivity of acetoin production are poor. Ethanol production is indeed the most obvious barrier for the efficient acetoin production in *S. cerevisiae* because pyruvate, a key intermediate, is preferentially used for producing ethanol rather than acetoin.

Therefore, for obvious reasons, to improve the production of acetoin through microbial processes, and more particularly of the conversion of pyruvate to acetoin, remains a constant aim. More particularly, there is still a need in a stable recombinant microorganism having an enhanced production yield of acetoin, in particular compatible with industrialization requirements.

SUMMARY OF THE INVENTION

The present invention relates to recombinant yeast having a reduced pyruvate decarboxylase activity, in the genome of which has been inserted:
- one or more nucleic acids encoding an acetolactate synthase or ALS,
- one or more nucleic acids encoding an acetolactate decarboxylase or ALD, and
- one or more copies of a nucleic acids encoding a NADH oxidase (NOXE).

According to a particular embodiment, the recombinant yeast according to the present invention may comprise one or more DNA constructs selected from a group comprising the following formulae:

$$5'\text{-[Gene 1]}_{x1}\text{-}3' \text{ and } 5'\text{-[Gene 2]}_{x2}\text{-}3' \text{ and } 5'\text{-[Gene 3]}_{x3}\text{-}3', \quad (I)$$

$$5'\text{-[Gene 1]}_{x1}\text{-[Gene 2]}_{x2}\text{-}3' \text{ and } 5'\text{-[Gene 3]}_{x3}\text{-}3', \quad (II)$$

$$5'\text{-[Gene 1]}_{x1}\text{-[Gene 2]}_{x2}\text{-[Gene 3]}_{x3}\text{-}3', \text{ and} \quad (III)$$

a combination thereof,
wherein:
"Gene 1" means a nucleic acid selected from a group comprising ALS, ALD or NOXE;
"Gene 2" means a nucleic acid selected from a group comprising ALS, ALD or NOXE but different from gene 1;
"Gene 3" means a nucleic acid selected from a group comprising ALS, ALD or NOXE but different from genes 1 and 2;
"ALS" is a nucleic acid encoding an acetolactate synthase;
"ALD" is a nucleic acid encoding an acetolactate decarboxylase;
"NOXE" is a nucleic acid encoding a NADH oxidase;
each of "x1", "x2" and "x3", one independently from the others, represents an integer ranging from 0 to 50, preferably from 0 to 20, and
provided that said recombinant yeast comprises at least one nucleic acid encoding for each of ALS, ALD and NOXE.

Preferably, each among "x1", "x2" and "x3", independently the ones of the others, represents an integer ranging from 0 to 15, which includes from 0 to 12, more particularly ranging from 0 to 5, in particular ranging from 0 to 3, and still better represents an integer equal to 1.

According to another particular embodiment, the recombinant yeast according to the invention may comprise at least one, preferably at least two, DNA construct(s) of above-mentioned formula (II), identical or different, wherein "Gene 3" means a nucleic acid encoding NADH oxidase.

According to yet another particular embodiment, the recombinant yeast according to the invention may comprise at least one, preferably at least two, DNA construct(s) of formula (IIa), identical or different, wherein each formula (IIa) has the following formula:

$$\text{5'-[(prom5)}_{y1}\text{-Gene 1-term5]}_{x5}\text{-[prom1-Gene}$$
$$\text{1-term1]}_{x1}\text{-[prom2-Gene 2-(term2)}_{z1}]_{x2}\text{-3' and}$$
$$\text{5'-[(prom3)}_{y2}\text{-Gene 3-(term3)}_{x2}]_{x3}\text{-3'} \qquad \text{(IIa)}$$

wherein:

Gene 1, Gene 2, Gene 3, "x1", "x2" and "x3" are such as above-defined;

"x5" represents an integer equal to 0 or 1;

"y1", "y2", "z1" and "z2", one independently from the others, represent an integer equal to 0 or 1;

when said recombinant yeast comprises at least two DNA constructs of formula (IIa), then "x1", "x2", "x3", "x5", "y1", "y2", "z1" and "z2" may be identical or different;

"prom 1" is a regulatory sequence which controls the expression of the sequence encoding the gene 1;

"prom 2" is a regulatory sequence which controls the expression of the sequence encoding the gene 2;

"prom 3" is a regulatory sequence which controls the expression of the sequence encoding the gene 3;

"prom5" is a regulatory sequence which controls the expression of Gene 1, said prom5 being identical or different from prom1;

"term1" is a transcription terminator sequence that ends expression of the sequence encoding the gene 1;

"term2" is a transcription terminator sequence that ends expression of the sequence encoding the gene 2;

"term3" is a transcription terminator sequence that ends expression of the sequence encoding the gene 3;

"term5" is a transcription terminator sequence that ends expression of Gene 1, said term5 being identical or different from term1.

According to another particular embodiment, the recombinant yeast according to the invention may comprise at least one, preferably at least two, DNA construct(s) of formula (IIb), identical or different, wherein each formula (IIb) has the following formula:

$$\text{5'-[(prom5)}_{y1}\text{-ALS-term5]}_{x5}\text{-[prom1-ALS-term1]}_{x1}\text{-}$$
$$\text{[prom2-ALD-(term2)}_{z1}]_{x2}\text{-3' and 5'-[(prom3)}_{y2}\text{-}$$
$$\text{NOXE-(term3)}_{z2}]_{x3}\text{-3'} \qquad \text{(IIb)}$$

wherein:

ALS, ALD, NOXE; "x1", "x2", "x3", "x5", "y1", "y2", "z1" and "z2" are such as above-defined;

when said recombinant yeast comprises at least two DNA constructs of formula (IIb), then "x1", "x2", "x3", "x5", "y1", "y2", "z1" and "z2" may be identical or different;

"prom 1" is a regulatory sequence which controls the expression of the sequence encoding the acetolactate synthase;

"prom 2" is a regulatory sequence which controls the expression of the sequence encoding the acetolactate decarboxylase;

"prom 3" is a regulatory sequence which controls the expression of the sequence encoding the NADH oxidase;

"prom5" is a regulatory sequence which controls the expression of the sequence encoding the acetolactate synthase, said prom5 being identical or different from prom1;

"term1" is a transcription terminator sequence that ends expression of the sequence encoding the acetolactate synthase;

"term2" is a transcription terminator sequence that ends expression of the sequence encoding the acetolactate decarboxylase;

"term3" is a transcription terminator sequence that ends expression of the sequence encoding the NADH oxidase; and "term5" is a transcription terminator sequence that ends expression of the sequence encoding the acetolactate synthase, said term5 being identical or different from term1.

According to another particular embodiment, the recombinant yeast according to the invention may comprise at least two DNA constructs of formula (II), (IIa) or (IIb), provided that all copies of NOXE's nucleic acid are located at a single of the at least two DNA constructs of formula (II), (IIa) or (IIb).

According to another particular embodiment, the recombinant yeast according to the invention may comprise at least two, preferably strictly two, DNA constructs of the following formulae (IIc) and (IId):

$$\text{5'-[(prom5)}_{y1}\text{-ALS-term5]}_{x5}\text{-[prom1-ALS-term1]}_{x1}\text{-}$$
$$\text{[prom2-ALD-(term2)}_{z1}]_{x2}\text{-3' and 5'-[(prom3)}_{y2}\text{-}$$
$$\text{NOXE-(term3)}_{z2}]_{x6}\text{-3; and} \qquad \text{(IIc)}$$

$$\text{5'-[(prom5)}_{y1}\text{-ALS-term5]}_{x5}\text{-[prom1-ALS-term1]}_{x1}\text{-}$$
$$\text{[prom2-ALD-(term2)}_{z1}]_{x2}\text{-3' and 5'-[(prom3)}_{y2}\text{-}$$
$$\text{NOXE-(term3)}_{z2}]_{x7}\text{-3;} \qquad \text{(IId)}$$

wherein:

ALS, ALD, NOXE; "prom1", "prom2", "prom3", "prom5", "term1", "term2", "term3" and "term5"; "x1", "x2" and "x3"; and "x5", "y1", "y2", "z1" and "z2" are such as above-defined;

"x1" to "x3", "x5", "y1", "y2", "z1" and "z2" for each formulae (IIc) and (IId) being identical or different; and "x6" and "x7" represent integers ranging from 0 to 50, preferably from 0 to 20, preferably from 0 to 12, more particularly from 2 to 5, preferably from 3 to 4, and better still equal to 3, provided that one among "x6" and "x7" represents 0.

This invention also pertains to the use of a recombinant yeast according to the present invention, for the production of acetoin and/or derivatives thereof, which encompass methyl vinyl ketone.

The invention also concerns a method for producing acetoin, said method comprising the steps of:

(a) culturing a recombinant yeast according to the present invention in an appropriate culture medium; and (c) recovering the acetoin.

Preferably, the said culture medium comprises a carbon source, preferably selected in a group comprising glucose and sucrose.

DESCRIPTION OF THE FIGURES

FIG. 1 shows the metabolic pathway in a recombinant yeast strain so as to replace the production of ethanol in favor of acetoin.

DETAILED DESCRIPTION OF THE INVENTION

Definitions

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of acetoin.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Homologous promoters known to allow a high level of expression in yeast are the ones selected in the following group; ADH1, GPDH, TEF1, truncated HXT7, PFK1, FBA1, PGK1 and TDH3 etc. Promoters particularly interesting in the present invention are hereinafter defined more in details.

In yeast, nucleic acid expression construct preferably comprises regulatory sequences, such as promoter and terminator sequences, which are operatively linked with the nucleic acid sequence coding for each of the considered genes, and more particularly for each of the above-mentioned ALS, ALD and NOXE enzymes according to the present invention.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of several copies of the said nucleic acid between a promoter, especially a strong promoter, and a terminator.

The "activity" of an enzyme is used interchangeably with the term "function" and designates, in the context of the invention, the capacity of an enzyme to catalyze the desired reaction.

The terms "reduced activity" or "attenuated activity" of an enzyme mean either a reduced specific catalytic activity of the protein obtained by mutation in the aminoacids sequence and/or decreased concentrations of the protein in the cell obtained by mutation of the nucleotide sequence or by deletion of the cognate corresponding gene.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, the disrupted pyruvate decarboxylase gene(s) in which the above-mentioned DNA construct(s) is/are intended to be inserted may advantageously comprises one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces, Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from pyruvate. For maximal production of acetoin, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is sucrose.

According to a particular embodiment, a carbon substrate according to the present invention does not consist of xylose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

So as to prevent the escape of the acetoin towards the 2,3-BDO, the genes that are involved in the reduction of acetoin into 2,3 BDO may be inactivated. In this regard, may be cited the endogenous butanediol dehydrogenase bdh1 and bdh2 (notably known by the EC number 1.1.1.4.), but also endogenous alcohol dehydrogenase adh1, adh3 and adh4 (notably known by the EC number 1.1.1.1). The inactivation of said genes belongs to the general knowledge of a man skilled in the art.

The presence of weak acids is known to be a limitation for growth and are often present in cellulose or molasses derived media.

Additional genetic modifications such as the disruption of the JEN1 gene (or systematic name: YKL217W or protein accession number P36035 (UniProtKB swiss-Prot)) and/or the over-expression of the HAA-1 gene (systematic name: YPR008W or accession number Q12753 (UniProtKB swiss-Prot)) lead to improve the strains resistance to weak acids in the implemented culture medium.

Jen 1 is a membrane protein responsible for lactate import in the cell (Casal M, et al. (1999), J. Bacteriol., 181(8): 2620-3).

HAA-1 is a transcriptional activator that controls the expression of membrane stress proteins responsible for resistance to weak acids. Its over expression enhances the resistance of yeast to acetic acids (Tanaka et al. (2012) Appl Environ Microbiol., 78(22): 8161-3).

The disruption of the JEN1 gene and the overexpression of the HAA-1 gene belong to the general knowledge of a man skilled in the art and may be notably carried out in using methods herein displayed.

In view of the herein after equation for the synthesis of acetoin in yeast, the conditions to consider in the present invention are necessarily aerobic conditions.

The terms "Aerobic conditions" refers to concentrations of oxygen in the culture medium that are sufficient for an aerobic or facultative anaerobic microorganism to use dioxygene as a terminal electron acceptor.

"Microaerobic condition" refers to a culture medium in which the concentration of oxygen is less than that in air, i.e. oxygen concentration up to 6% $O_2$.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

Recombinant Yeast According to the Invention

As above-mentioned, the present invention relates to a recombinant yeast having a reduced pyruvate decarboxylase activity, in the genome of which has been inserted:
- one or more nucleic acids encoding an acetolactate synthase or ALS,
- one or more nucleic acids encoding an acetolactate decarboxylase or ALD, and
- one or more copies of a nucleic acids encoding a NADH oxidase (or NOXE).

As shown in the examples herein, the inventors unexpectedly found that the presence of a nucleic acid encoding a NADH oxidase, advantageously the presence of a plurality of copies thereof, in a recombinant yeast in which the pyruvate decarboxylase activity has been reduced and in which it has been further integrated genes allowing expression of the ALS and ALD enzymes required for the synthesis of acetoin, not only contributes to stabilize said recombinant yeast but also allows a significant enhancing of the growth of this strain, as well as the yield of acetoin production.

The use of Crabtree positive yeast organisms such as *saccharomyces cerevisiae*, and especially of recombinant yeast organisms such as *saccharomyces cerevisiae*, for producing metabolites of interest is advantageous since, in contrast to bacteria, yeast cells have the ability to perform fermentation in the presence of oxygen in presence of sufficient amount of sugar such as glucose or sucrose. In contrast, bacteria perform fermentation in anaerobic conditions only. Further, yeast organisms are not subject to viral infection in contrast to bacteriophage for bacteria. Yet further, culture of yeast organisms are rarely subject to contamination by non-desired microorganisms such as bacteria because yeast cells cause rapid acidification of their environment up to pH4, e.g. the culture medium supporting their growth. Still further, yeast cells do not excrete number of undesired metabolites such as lactic acid, the presence of which in the culture medium is an actual drawback for subsequent purification of metabolite(s) of interest. Yet further, yeast organisms, including recombinant yeast organisms, have a higher genetic stability as compared to bacteria.

The equation for the synthesis of acetoin in yeast is:

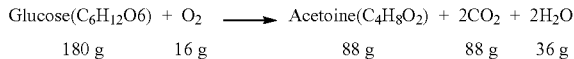

Said mass equation is possible due to the fact that *S. cerevisiae* can ferment even in the presence of oxygen.

In view of the above equation, the maximum theoretical yield of acetoin would be 97.78 g for an input of 200 g of glucose.

As it is shown in the examples herein, the effective yield of acetoin with recombinant yeast according to the present invention is relatively close to this maximum theoretical yield (up to 83%). According to the inventor's knowledge, such yield was never obtained in yeast until now.

Thus, the production with a high yield of acetoin is successfully reached in a recombinant yeast according to the invention, paving the way for industrial production of acetoin in yeast.

Surprisingly, as it is also shown in the examples herein, no toxicity of the produced acetoin on the yeast cells is observed, even at high concentrations of synthesized acetoin. What is more, the synthesized acetoin is entirely exported outside the cells, thus substantially simplifying the purification process.

The NADH oxidase (or NOXE) used in the recombinant yeast according to the present invention is a very specific "NADH-dependent" enzyme as it does not consume any carbonated acceptor. For this reason, the selected NADH oxidase does not interfere directly with the carbonated metabolism but replenishes the NAD$^+$ pool in producing water.

In this regard, the NADH oxidase used in the recombinant yeast according to the present invention differs notably from the "NADH-dependent" enzyme disclosed in the above-mentioned prior art documents, and especially in US 2011/0124060 and WO 2013/076144.

According to certain embodiments, the recombinant yeast may comprise one or more DNA constructs selected from a group comprising the following formulae:

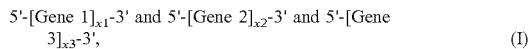

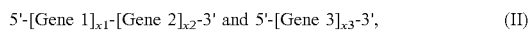

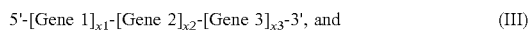

a combination thereof,
wherein:
"Gene 1" means a nucleic acid selected from a group comprising ALS, ALD or NOXE;
"Gene 2" means a nucleic acid selected from a group comprising ALS, ALD or NOXE but different from gene 1;
"Gene 3" means a nucleic acid selected from a group comprising ALS, ALD or NOXE but different from genes 1 and 2;
"ALS" is a nucleic acid encoding an acetolactate synthase;
"ALD" is a nucleic acid encoding an acetolactate decarboxylase;
"NOXE" is a nucleic acid encoding a NADH oxidase;

each of "x1", "x2" and "x3", one independently from the others, represents an integer ranging from 0 to 50, preferably from 0 to 20, and
provided that said recombinant yeast comprises at least one nucleic acid encoding for each of ALS, ALD and NOXE.

Preferably, each among "x1", "x2" and "x3", independently the ones of the others, represents an integer ranging from 0 to 10, more particularly ranging from 0 to 5, in particular ranging from 0 to 3, and still better represents an integer equal to 1.

As intended herein, each of x1, x2 and x3 may have a value selected in a group comprising 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

In certain embodiments wherein, in a DNA construct of formulae (I) to (III) above, one or more of the integers "x1", "x2" and/or "x3", one independently from the others, has a value of two or more, then each of the two or more copies of the corresponding gene among related Gene 1, Gene 2 and/or Gene 3 may be identical or different. Various distinct sequences of ALS, ALD and NOXE are depicted in Table 1 herein.

In illustrative embodiments of a DNA construct selected among those of formulae (I) to (III) above, wherein "x1" is an integer equal to 2 and Gene 1 is a nucleic acid encoding an acetolactate synthase (ALS), then the two ALS-coding sequences contained in the said DNA construct may be identical or different, For example, according to this particular embodiment, it means that the first copy of the nucleic acid encoding an acetolactate synthase may be the nucleic acid encoding ALS.Bs and the second copy of the nucleic acid encoding an acetolactate synthase may be the nucleic acid encoding ALS.Pp.

In the embodiments of a recombinant yeast according to the invention wherein the said recombinant yeast comprises at least two DNA constructs selected in the group comprising the DNA constructs of formulae (I) to (III), each DNA construct, and more particularly each of gene among related Gene 1, Gene 2 and/or Gene 3 contained therein, may be identical or different.

Herein after are presented some illustrative embodiments of a DNA construct selected in a group comprising the DNA constructs of formula (I), (II) and (III).

Recombinant Yeast Comprising One DNA Construct of Formula (I):

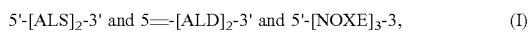

A recombinant yeast comprising a DNA construct of formula (I) above has a reduced pyruvate decarboxylase activity, and possesses the four following DNA sub-constructs (i) to (iii) that have been introduced in the genome thereof:

(i) a DNA sub-construct comprising two nucleic acids, identical or distinct one from the other, each nucleic acid encoding ALS, said DNA sub-construct being introduced at a first location in the genome of said recombinant yeast;

(ii) a DNA sub-construct comprising two nucleic acids, identical or distinct one from the other, each nucleic acid encoding ALD, said DNA sub-construct being introduced at a second location in the genome of said recombinant yeast, distinct from the location wherein the DNA sub-construct comprising the nucleic acids encoding ALS have been inserted; and (iii) a DNA sub-construct comprising three nucleic acids, identical or distinct one from the other(s), each nucleic acid encoding NOXE, said DNA sub-construct being introduced at a third location in the genome of said recombinant yeast, distinct from the first and second locations wherein the DNA sub-construct comprising nucleic acids encoding ALS and of the DNA sub-construct comprising nucleic acids encoding ALD, respectively, have been inserted.

In some embodiments, the required reduced pyruvate decarboxylase activity of the said specific recombinant yeast may be obtained by insertion in at least one of the yeast pdc genes of at least one DNA sub-construct (i) to (iii), or alternatively a combination thereof.

Recombinant Yeast Comprising One DNA Construct of Formula (II):

$$5'\text{-}[ALS]_2\text{-}[ALD]_2\text{-}3' \text{ and } 5'\text{-}[NOXE]_3\text{-}3', \qquad (II)$$

A recombinant yeast comprising a DNA construct of formula (II) above has a reduced pyruvate decarboxylase activity, and has a genome wherein has been inserted the two following DNA sub-constructs (A) and (B), namely:

(A) a first DNA sub-construct $5'\text{-}[ALS]_2\text{-}[ALD]_2\text{-}3'$, said first DNA sub-construct being introduced at a first location in the genome of said recombinant yeast, and said first DNA sub-construct comprising;

(i) two nucleic acids, identical or distinct one from the other, each nucleic acid encoding ALS; and (ii) two nucleic acids, identical or distinct one from the other, each nucleic acid encoding ALD; and (B) a second DNA sub-construct $5'\text{-}[NOXE]_3\text{-}3'$, said DNA sub-construct being introduced at a second location in the genome of said recombinant yeast, distinct from the first location wherein the first DNA sub-construct has been inserted, and said second DNA sub-construct comprising (iii) three nucleic acids, identical or distinct one from the other, each nucleic acid encoding NOXE.

In certain embodiments, the required reduced pyruvate decarboxylase activity of said specific recombinant yeast may be obtained by insertion in at least one of the yeast pdc genes of first DNA sub-construct and/or of second DNA sub-construct.

Recombinant Yeast Comprising One DNA Construct of Formula (III):

$$5'\text{-}[ALS]_2\text{-}[ALD]_2\text{-}[NOXE]_3\text{-}3', \qquad (III)$$

A recombinant yeast comprising a DNA construct of formula (III) above has a reduced pyruvate decarboxylase activity and possesses a genome wherein has been inserted one DNA construct located at a desired location in the genome of said recombinant yeast, said DNA construct comprising;

(i) two nucleic acids, identical or distinct one from the other, each nucleic acid encoding ALS;

(ii)
two nucleic acids, identical or distinct one from the other, each nucleic acid encoding ALD; and (iii) three nucleic acids, identical or distinct one from the other, each nucleic acid encoding NOXE.

In certain embodiments, the required reduced pyruvate decarboxylase activity of said specific recombinant yeast may be obtained by insertion of said DNA construct in at least one of the yeast pdc genes.

For each of these three illustrative embodiments above of a recombinant yeast according to the invention, and as above-mentioned, when "x1" to "x3", one independently from the others, represent(s) an integer having a value of two or more, then:

one copy of ALS within a single DNA construct may be identical to another copy of ALS comprised in the said DNA construct or may be identical to all the other copies of ALS contained in the said DNA construct, or alternatively the said one copy of ALS may be distinct from each other copy of ALS contained in the said DNA construct.

one copy of ALD within a single DNA construct may be identical to another copy of ALD comprised in the said DNA construct or may be identical to all the other copies of ALD contained in the said DNA construct, or alternatively the said one copy of ALD may be distinct from each other copy of ALD contained in the said DNA construct.

one copy of NOXE within a single DNA construct may be identical to another copy of NOXE comprised in the said DNA construct or may be identical to all the other copies of NOXE contained in the said DNA construct, or alternatively the said one copy of NOXE may be distinct from each other copy of NOXE contained in the said DNA construct.

Recombinant Yeast Comprising One DNA Construct of Formula (III) and One DNA Construct of Formula (I):

$$5'\text{-}[ALS]_1\text{-}[ALD]_1\text{-}[NOXE]_1\text{-}3', \text{ and} \qquad (III)$$

$$5'\text{-}[ALS]_0\text{-}3' \text{ and } 5'\text{-}[ALD]_0\text{-}3' \text{ and } 4'\text{-}[NOXE]_{12}\text{-}3', \qquad (I)$$

The resulting recombinant yeast has a reduced pyruvate decarboxylase activity, and has a genome wherein has been inserted the two following DNA sub-constructs (A) and (B), namely:

(A) a first DNA sub-construct $5'\text{-}[ALS]_1\text{-}[ALD]_1\text{-}[NOXE]_1\text{-}3'$, said first DNA sub-construct being introduced at a first location in the genome of said recombinant yeast, and said first DNA sub-construct comprising;

(i) one nucleic acid encoding ALS;

(ii) one nucleic acid encoding ALD; and (iii) one nucleic acid encoding NOXE; and (B) a second DNA sub-construct $5'\text{-}[ALS]_0\text{-}3'$ and $5'\text{-}[ALD]_0\text{-}3'$ and $5'\text{-}[NOXE]_{12}\text{-}3'$, said second DNA sub-construct being introduced at a second location in the genome of said recombinant yeast, and said second DNA sub-construct comprising:

(i) twelve nucleic acids encoding NOXE.

Recombinant Yeast Comprising Two DNA Constructs of Formula (III) and One DNA Construct of Formula (I):

$$5'\text{-}[ALS]_1\text{-}[ALD]_1\text{-}[NOXE]_1\text{-}3', \qquad (III\text{-}1)$$

$$5'\text{-}[ALS]_1\text{-}[ALD]_1\text{-}[NOXE]_1\text{-}3', \qquad (III\text{-}2)$$

$$5'\text{-}[ALS]_0\text{-}3' \text{ and } 5'\text{-}[ALD]_0\text{-}3' \text{ and } 4'\text{-}[NOXE]_{12}\text{-}3', \qquad (I)$$

The resulting recombinant yeast has a reduced pyruvate decarboxylase activity, and has a genome wherein has been inserted the two following DNA sub-constructs (A), (B) and (C), namely:

(A) a first DNA sub-construct $5'\text{-}[ALS]_1\text{-}[ALD]_1\text{-}[NOXE]_1\text{-}3'$, said first DNA sub-construct being introduced at a first location in the genome of said recombinant yeast, and said first DNA sub-construct comprising;

(i) one nucleic acid encoding ALS;

(ii) one nucleic acid encoding ALD; and (iii) one nucleic acid encoding NOXE;

(B) a second DNA sub-construct $5'\text{-}[ALS]_1\text{-}[ALD]_1\text{-}[NOXE]_1\text{-}3'$, said second DNA sub-construct being introduced at a second location in the genome of said recombinant yeast, and said second DNA sub-construct comprising;

(i) one nucleic acid encoding ALS;
(ii) one nucleic acid encoding ALD; and
(iii) one nucleic acid encoding NOXE;
and (B) a third DNA sub-construct 5'-[ALS]$_0$-3' and 5'-[ALD]$_0$-3' and 4'-[NOXE]$_{12}$-3', said third DNA sub-construct being introduced at a third location in the genome of said recombinant yeast, and said third DNA sub-construct comprising;
(i) twelve nucleic acids encoding NOXE;

Recombinant Yeast Comprising Two DNA Constructs of Formula (II) and One DNA Construct of Formula (I):

$$5'-[ALS]_1-[ALD]_1-3' \text{ and } 5'-[NOXE]_0-3', \quad (II-1)$$

$$5'-[ALS]_1-[ALD]_1-3' \text{ and } 5'-[NOXE]_0-3', \quad (II-2)$$

$$5'-[ALS]_0-3' \text{ and } 5'-[ALD]_0-3' \text{ and } 5'-[NOXE]_{12}-3', \quad (I)$$

The resulting recombinant yeast has a reduced pyruvate decarboxylase activity, and has a genome wherein has been inserted the three following DNA sub-constructs (A), (B) and (C), namely:

(A) a first DNA sub-construct 5'-[ALS]$_1$-[ALD]$_1$-3' and 5'-[NOXE]$_0$-3', said first DNA sub-construct being introduced at a first location in the genome of said recombinant yeast, and said first DNA sub-construct comprising;
(i) one nucleic acids encoding ALS; and
(ii) one nucleic acids encoding ALD;

(B) a second DNA sub-construct 5'-[ALS]$_1$-[ALD]$_1$-3' and 5'-[NOXE]$_0$-3', said second DNA sub-construct being introduced at a second location in the genome of said recombinant yeast, and said second DNA sub-construct comprising;
(i) one nucleic acids encoding ALS; and
(ii) one nucleic acids encoding ALD;
and (B) a third DNA sub-construct 4'-[NOXE]$_{12}$-3', said DNA sub-construct being introduced at a third location in the genome of said recombinant yeast, distinct from the first location wherein the first DNA sub-construct has been inserted, and said second DNA sub-construct comprising (iii) twelve nucleic acids, identical or distinct one from the other, each nucleic acid encoding NOXE.

In certain embodiments, the required reduced pyruvate decarboxylase activity of said specific recombinant yeast may be obtained by insertion in at least one of the yeast pdc genes of first DNA sub-construct and/or of second DNA sub-construct.

According to certain specific embodiments, a recombinant yeast according to the invention may comprise at least one, preferably at least two, DNA construct(s) of the above-mentioned formula (II), wherein "Gene 3" means a nucleic acid encoding a NADH oxidase (or NOXE).

According to these specific embodiments, each nucleic acid among Gene 1 and Gene 2 necessarily means a nucleic acid selected from a group comprising ALS and ALD. In these embodiments, at least one copy of the inserted ALS and ALD is present. In the embodiments wherein only one construct of formula (II) is inserted in the yeast genome, then each nucleic acid among Gene 1 and Gene 2 necessarily means a nucleic acid selected from a group comprising ALS and ALD and one copy of each of ALS and ALD is present. In the embodiments wherein a set of two or more constructs of formula (II) are inserted in the yeast genome, then each nucleic acid among Gene 1 and Gene 2 necessarily means a nucleic acid selected from a group comprising ALS and ALD and at least one copy of each of ALS and ALD is present in the said set of two or more DNA constructs of formula (II).

In addition, when the said recombinant yeast according to the invention comprises at least two DNA constructs of the above-formula (II), then said DNA constructs of the above-mentioned formula (II) may be identical or different.

According to a preferred embodiment, a recombinant yeast according to the invention may comprise at least one, preferably at least two, DNA construct(s) of formula (IIa), identical or different, wherein each formula (IIa) has the following formula:

$$5'-[(prom5)_{y1}\text{-Gene 1-term5}]_{x5}\text{-[prom1-Gene 1-term1}]_{x1}\text{-[prom2-Gene 2-(term2)}_{z1}]_2\text{-3' and}$$
$$5'-[(prom3)_{y2}\text{-Gene 3-(term3)}_{z2}]_{x3}\text{-3'} \quad (IIa)$$

wherein:
Gene 1, Gene 2 and Gene 3, "x1", "x2" and "x3" are such as above-defined;
"x5" represents an integer equal to 0 or 1;
"y1", "y2", "z1" and "z2", one independently from the others, represent an integer equal to 0 or 1;
when said recombinant yeast comprises at least two DNA constructs of formula (IIa), then "x1", "x2", "x3", "x5", "y1", "y2", "z1" and "z2" may be identical or different;
"prom 1" is a regulatory sequence which controls the expression of the sequence encoding the gene 1;
"prom 2" is a regulatory sequence which controls the expression of the sequence encoding the gene 2;
"prom 3" is a regulatory sequence which controls the expression of the sequence encoding the gene 3;
"prom5" is a regulatory sequence which controls the expression of Gene 1, said prom5 being identical or different from prom1;
"term1" is a transcription terminator sequence that ends expression of the sequence encoding the gene 1;
"term2" is a transcription terminator sequence that ends expression of the sequence encoding the gene 2;
"term3" is a transcription terminator sequence that ends expression of the sequence encoding the gene 3; and
"term5" is a transcription terminator sequence that ends expression of Gene 1, said term5 being identical or different from term1.

For a better clarity regarding the characteristics "x5" and "y1", is herein after presented examples to illustrate more in details related particular embodiments:
when "x5" is an integer equal to 1 and "y1" represents an integer equal to 0, then it means that the considered Gene 1 is under the control of the promoter of the gene of the recombinant yeast in which the considered DNA construct has been inserted; or
when "x5" is an integer equal to 1 and "y1" represents an integer equal to 1, then it means that the considered Gene 1 is under the control of the promoter "prom5". In this regard, the sequence of promoter of the endogenous gene, preferably of pdc gene, in which the DNA construct is inserted is eliminated, or at least interrupted, as well as the sequence of its related coding region.

In addition, regarding notably the characteristics "y2" and "z2", is herein after presented examples to illustrate more in details related particular embodiments (of course, in these herein after examples, "x3" represents an integer equal to 1 or more):
when "y2" is an integer equal to 0, then it means that the considered Gene 3 is under the control of the promoter of the gene of the recombinant yeast in which the considered DNA construct has been inserted; or
when "y2" is an integer equal to 1, then it means that the considered Gene 3 is under the control of the promoter "prom3". In this regard, the sequence of promoter of the endogenous gene in which the DNA construct is inserted is eliminated, or at least interrupted, as well as the sequence of its related coding region.

when "z2" is an integer equal to 0, then it means that the considered Gene 3 is linked to the transcription terminator of the gene of the recombinant yeast in which the considered DNA construct has been inserted; or when "z2" is an integer equal to 1, then it means that the considered Gene 3 is linked to the transcription terminator "term3". In this regard, the sequence of the transcription terminator of the endogenous gene in which the DNA construct is inserted is eliminated, or at least interrupted, as well as the sequence of its related coding region.

Regarding "z1" when present in formulas described in the present specification, the above-mentioned regarding "z2" apply mutatis mutandis.

According to another preferred embodiment, a recombinant yeast according to the invention may comprise at least one, preferably at least two, DNA construct(s) of the following formula (IIb):

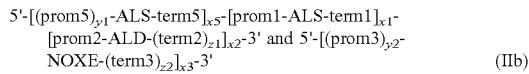
$$5'-[(prom5)_{y1}-ALS-term5]_{x5}-[prom1-ALS-term1]_{x1}-[prom2-ALD-(term2)_{z1}]_{x2}-3' \text{ and } 5'-[(prom3)_{y2}-NOXE-(term3)_{z2}]_{x3}-3' \quad \text{(IIb)}$$

wherein:
ALS, ALD, NOXE, "x1", "x2", "x3", "x5", "y1", "y2", "z1" and "z2" are such as above-defined;
when said recombinant yeast comprises at least two DNA constructs of formula (IIb), then "x1", "x2", "x3", "x5", "y1", "y2", "z1" and "z2" may be identical or different;
"prom 1" is a regulatory sequence which controls the expression of the sequence encoding the acetolactate synthase;
"prom 2" is a regulatory sequence which controls the expression of the sequence encoding the acetolactate decarboxylase;
"prom 3" is a regulatory sequence which controls the expression of the sequence encoding the NADH oxidase;
"prom5" is a regulatory sequence which controls the expression of the sequence encoding the acetolactate synthase, said prom5 being identical or different from prom1;
"term1" is a transcription terminator sequence that ends expression of the sequence encoding the acetolactate synthase;
"term2" is a transcription terminator sequence that ends expression of the sequence encoding the acetolactate decarboxylase;
"term3" is a transcription terminator sequence that ends expression of the sequence encoding the NADH oxidase; and
"term5" is a transcription terminator sequence that ends expression of the sequence encoding the acetolactate synthase, said term5 being identical or different from term1.

According to another preferred embodiment, a recombinant yeast according to the invention may comprise at least two DNA constructs of formula (II), (IIa) or (IIb), provided that all copies of NOXE's nucleic acid are located at a single of the at least two DNA constructs of formula (II), (IIa) or (IIb).

According to another preferred embodiment, a recombinant yeast according to the invention may comprise at least two, preferably strictly two, DNA constructs of following formulae (IIc) and (IId):

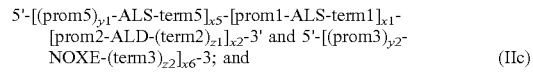
$$5'-[(prom5)_{y1}-ALS-term5]_{x5}-[prom1-ALS-term1]_{x1}-[prom2-ALD-(term2)_{z1}]_{x2}-3' \text{ and } 5'-[(prom3)_{y2}-NOXE-(term3)_{z2}]_{x6}-3'; \text{ and} \quad \text{(IIc)}$$

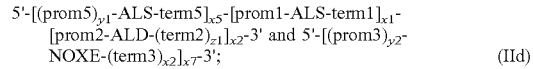
$$5'-[(prom5)_{y1}-ALS-term5]_{x5}-[prom1-ALS-term1]_{x1}-[prom2-ALD-(term2)_{z1}]_{x2}-3' \text{ and } 5'-[(prom3)_{y2}-NOXE-(term3)_{z2}]_{x7}-3'; \quad \text{(IId)}$$

wherein:
ALS, ALD, NOXE, "prom1", "prom2", "prom3", "prom5", "term1", "term2", "term3", "term5", "x1", "x2", "x3", "x5", "y1", "y2", "z1" and "z2" are such as above-defined; and
"x1" to "x3", "x5", "y1", "y2", "z1" and "z2" for each formulae (IIc) and (IId) being identical or different; and
"x6" and "x7" represent integers ranging from 0 to 50, preferably from 0 to 20, preferably from 0 to 12, more particularly from 2 to 5, preferably from 3 to 4, and better still equal to 3, provided that one among "x6" and "x7" represents 0.

Advantageously, the first gene 1 in 5'- in a DNA construct of formulae (I) to (III) is preferably a gene represented by a nucleic acid encoding ALS, and more particularly said first gene 1 is under the control of the promoter of the gene of the recombinant yeast in which the considered DNA construct have been inserted.

More particularly, it means that, for a DNA construct of formula (IIa), (IIb), (IIc) or (IId), "x5" advantageously represents an integer equal to 1 and "y1" represents an integer equal to 0.

In view of the complexity of the above-mentioned DNA constructs and DNA sub-constructs according to the present invention, it is emphasized that:

regarding one DNA construct of the invention, when "x1", "x2" and/or "x3" represent(s) an integer greater than or equal to 2, then:
each copy for a related nucleic acid among Gene 1, Gene 2 and/or Gene 3 may be identical or different; and/or
the promoter and/or terminator for each copy for a related nucleic acid among Gene 1, Gene 2 and/or Gene 3 may be identical or different;

when a recombinant yeast comprises at least two DNA constructs, said at least two DNA constructs may be identical or different regarding:
(i) their general formula in that a DNA construct may be characterized by a formula selected among the group comprising formulae (I) to (III);
(ii) the value of "x1" to "x3" and "x5" to "x7", "y1", "y2", "z1" and/or "z2";
(iii) the nature of the promoter regarding a same gene;
(iv) the nature of the terminator regarding a same gene; and/or
(v) the nature of same gene itself in that ALS, ALD and NOXE may derive from organisms belonging to different genera, as notably hereinafter displayed in Table 1.

Methods implemented to realize a DNA construct such as above-defined belong to the general knowledge of the man of the art.

In this regard, the one skilled in the art may advantageously refer to the method described in Shao et al. (Nucleic Acids Research, 2009, Vol. 37, No. 2: e16) and Shao et al. (Methods in Enzymology, 2012 Elsevier Inc., Vol. 517: 203, eventually with only minor variation, and is more particularly developed in the herein after examples.

Reduced Pyruvate Decarboxylase Activity

Endogenous pyruvate decarboxylase activity in yeast converts pyruvate to acetaldehyde, which is then converted to ethanol or to acetyl-CoA via acetate.

As previously mentioned, the present invention relates to a recombinant yeast having reduced pyruvate decarboxylase activity, in the genome of which has been inserted a specific DNA construct.

According to a particular embodiment, the recombinant yeast is characterized by the fact that one or more endogenous pyruvate decarboxylase-encoding gene(s) may be switched off.

The pyruvate decarboxylase activity of a recombinant yeast according to the invention may be reduced by all methods known by a man skilled in the art.

In this regard, the pyruvate decarboxylase activity of a recombinant yeast according to the invention may for example be reduced by (i) disrupting at least one gene encoding a pyruvate decarboxylase by inserting within said at least one gene encoding a pyruvate decarboxylase at least one exogenous DNA construct by methods known to the man of the art, (ii) mutations in regulatory regions reducing pyruvate decarboxylase transcription, (iii) mutations in a start codon, notably by replacing AUG by GUG, and (iv) mutations in coding sequences altering the activity (v) mutations, insertions or deletion in the coding sequence altering the protein stability (vi) mutations altering the pyruvate decarboxylase mRNA half life.

Regarding the first option (i), the DNA construct implemented to disrupt a considered pdc gene may be an exogenous DNA construct different from DNA constructs according to the invention as previously described, a DNA construct according to the invention, or a combination thereof.

Also, and as above-mentioned, DNA constructs according to the invention of formula (I) and (II) are each composed of two or more DNA sub-constructs.

Therefore, according to a particular variant of realization, the pyruvate decarboxylase activity of a recombinant yeast according to the invention may be reduced by disrupting at least one gene encoding a pyruvate decarboxylase by inserting within said gene only at least one DNA sub-constructs of at least one DNA constructs according to the invention of formula (I) and (II).

Preferably, the endogenous pyruvate decarboxylase activity may be reduced by disruption of at least one pdc gene.

Indeed, yeasts may have one or more genes encoding pyruvate decarboylase. For example, there is one gene encoding pyruvate decarboxylase in *Kluyveromyces lactis*, while there are three isozymes of pyruvate decarboxylase encoded by the PDC1, PCD5, and PDC6 genes in *Saccharomyces cerevisiae*, as well as a pyruvate decarboxylase regulatory gene PDC2.

Preferably, and as herein after defined, a recombinant yeast according to the invention may be a recombinant *Saccharomyces* genus, and preferably a recombinant *Saccharomyces cerevisiae* species.

In this regard, and according to a first variant, the pyruvate decarboxylase activity may be reduced by disruption of at least one pdc gene, preferably of at least two pdc genes, and more particularly of only two pdc genes.

In addition, the disrupted pdc gene(s) may be selected from the group consisting of pdc1, pdc5, pdc6 and a mixture thereof, and preferably of pdc1 and pdc6.

Preferably, when the recombinant yeast belongs to the *Saccharomyces* genus, then the pyruvate decarboxylase activity may be reduced by disruption of at least two pdc genes, preferably selected from the group consisting of pdc1, pdc5, pdc6 and a combination thereof, and more particularly from the group consisting of pdc1 and pdc6.

Indeed, the interruption of the three pdc genes in *Saccharomyces* genus, preferably, *Saccharomyces cerevisiae* species, dramatically reduces strain growth, rendering it incompatible with any industrial application.

According to a particular variant, in *Saccharomyces* genus, preferably *Saccharomyces cerevisiae* species, only pdc1 and pdc6 genes are disrupted and the expression of pdc5 is attenuated.

The method implemented to attenuate the expression of a specific gene belongs to the general knowledge of the man of the art.

In this regard, the one skilled in the art may advantageously refer to any method that is well known in the art.

Advantageously, for attenuating the expression of pdc 5, its transcription may be placed under the control of a weak promoter, such as notably RPLA1, URA3, MET25, HIS3, TRP1, GAP1, NUP57 or TFC1, and preferably RPLA1 (=Sequence SEQ ID No 37).

A method implemented to measure the activity level of a pyruvate decarboxylase belongs to the general knowledge of the man of the art.

In this regard, the one skilled in the art may advantageously refer to the method described in Wang et al. (Biochemistry, 2001, 40: 1755-1763).

Acetolactate Synthase

The acetolactate synthase (ALS) enzyme (also known as acetohydroxy acid synthase (AHAS), α-acetohydroxy acid synthetase, α-acetohydroxy acid synthase, α-acetolactate synthase, α-acetolactate synthetase, acetohydroxy acid synthetase, acetohydroxy acid synthase, acetolactate pyruvate-lyase (carboxylating), acetolactic synthetase) is a protein which catalyzes the first step in the synthesis of the branched-chain amino acids (valine, leucine, and isoleucine).

ALS is an enzyme specifically involved in the chemical reaction involving the conversion of two pyruvate molecules to an acetolactate molecule and carbon dioxide. The reaction uses thyamine pyrophosphate in order to link the two pyruvate molecules.

A method implemented to measure the activity level of an acetolactate synthase belongs to the general knowledge of the man of the art.

In this regard, the one skilled in the art may advantageously refer to the method described in Poulsen et al. (Eur. J. Biochem. 185, 1989: 433-439).

Preferred acetolactate synthase in the present invention is known by the EC number 2.2.1.6.

According to a preferred embodiment, the nucleic acid(s) encoding an acetolactate synthase or ALS may be nucleic acid(s) preferably selected from a group comprising *Bacillus subtilis, Nicotiana tabacum, Paenibacillus polymyxa*, and a mixture thereof, and preferably *Nicotiana tabacum* and *Paenibacillus polymyxa*.

According to a yet preferred embodiment, the nucleic acid(s) encoding an acetolactate synthase or ALS may be nucleic acid(s) selected from the group consisting of sequences having at least 65%, preferably at least 80%, nucleic acid identity with the nucleic acid sequences SEQ ID NO: 1, 3 and 5.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding an acetolactate synthase may be nucleic acid(s) encoding an amino acid sequence selected from the group consisting of sequences having at least 65%, preferably at least 80%, identity with sequences SEQ ID NO: 2, 5 and 6.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of ALS in the present invention is regulated by at least one promoter and at least one terminator, such as herein after defined more in details, which are present in 5' and 3' position respectively of the nucleic acid sequence encoding the ALS.

Acetolactate Decarboxylase

The acetolactate decarboxylase (ALD) enzyme (also known as α-acetolactate decarboxylase, (S)-2-hydroxy-2-methyl-3-oxobutanoate carboxy-lyase, (S)-2-hydroxy-2-methyl-3-oxobutanoate carboxy-lyase [(R)-2-acetoin-forming] or (S)-2-hydroxy-2-methyl-3-oxobutanoate carboxy-lyase [(3R)-3-hydroxybutan-2-one-forming]) belongs to the family of lyases, specifically the carboxy-lyases, which cleave carbon-carbon bonds and participates in butanoate metabolism and c5-branched dibasic acid metabolism.

ALD is an enzyme specifically involved in the chemical reaction involving the conversion of α-acetolactate molecule to an acetoine molecule and carbon dioxide.

A method implemented to measure the activity level of an acetolactate decarboxylase belongs to the general knowledge of the man of the art.

In this regard, the one skilled in the art may advantageously refer to the method described in Dulieu et al. (Enzyme and Microbial Technology 25, 1999: 537-542).

Preferred acetolactate decarboxylase in the present invention is known by the EC number 4.1.1.5.

According to a preferred embodiment, the nucleic acid(s) encoding an acetolactate decarboxylase or ALD may be nucleic acid(s) selected from the group comprising *Brevibacillus brevis, Enterobacter aerogenes, Lactococcus lactis*, and a mixture thereof, and preferably *Brevibacillus brevis* and *Enterobacter aerogenes*.

According to a yet preferred embodiment, the nucleic acid(s) encoding an acetolactate decarboxylase or ALD may be nucleic acid(s) selected from the group consisting of sequences having at least 36%, preferably at least 80%, nucleic acid identity with the nucleic acid sequences SEQ ID NO: 7, 9 and 11.

As described herein, a nucleic acid sequence having at least 36% nucleotide identity with a reference nucleic acid sequence encompasses nucleic acid sequences having at least 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding an acetolactate decarboxylase may be nucleic acid(s) encoding an amino acid sequence selected from the group consisting of sequences having at least 36%, preferably at least 80% identity with sequences SEQ ID NO: 8, 10 and 12.

As described herein, an amino acid sequence having at least 36% amino acid identity with a reference amino acid sequence encompasses amino acid sequences having at least 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of ALD in the present invention is regulated by at least one promoter and at least one terminator, such as herein after defined more in details, which are respectively present in 5' and 3' position of the nucleic acid sequence encoding the ALD.

NADH Oxidase

The inactivation or reduction of activity of at least one pdc gene inactivates or reduces the ethanol fermentation pathway in yeast. In consequence, this induces an unbalanced redox state which is not relieved by the expression of ALS and ALD. Indeed, the pathway from glucose to 2 pyruvate generates 2 NADH equivalent, while the transformation of 2 pyruvate to acetoin recycles no NADH into NAD+ (see FIG. 1).

The inventors found that a bacterial water forming NADH oxidase (also called in the present description NOXE oxidase or NOXE) enzyme, in a specific expression level, can not only allow to equilibrate the redox state which allows enhancing the stability of this strain but also allows enhancing the growth of this strain and further improving the yield of acetoin.

A bacterial water forming NADH oxidase is an enzyme that catalyses the following reaction:

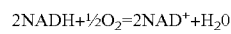

Preferred water forming NADH oxidase in the present invention are known by the EC number 1.6.3.1 and 1.6.99.3 (also known as NAD(P)H oxidase (H(2)O(2)-forming), dual oxidase, NAD(P)H oxidase, ThOX, THOX2, Thyroid NADPH oxidase, Thyroid oxidase Thyroid oxidase 2 for EC 1.6.3.1 and NADH dehydrogenase, Beta-NADH dehydrogenase dinucleotide, Cytochrome c reductase, Diaphorase, Dihydrocodehydrogenase I dehydrogenase, Dihydronicotinamide adenine dinucleotide dehydrogenase, Diphosphopyrinase, DPNH diaphorase, NADH diaphorase, NADH hydrogenase, NADH oxidoreductase, NADH-menadione oxidoreductase, NADH: cytochrome c oxidoreductase, Reduced diphosphopyridine nucleotide diaphorase, Type 1 dehydrogenase, Type I dehydrogenase for EC 1.6.99.3).

A water forming NADH oxidase which may be considered in the present invention is notably described in WO 2006/134277.

A method implemented to measure the activity level of a NADH oxidase according to the invention belongs to the general knowledge of the man of the art.

In this regard, the one skilled in the art may advantageously refer to the method described in Lopez DE FELIPE et al. (International Daily Journal, 2001, vol. 11: 37-44 (ISSN 0958-6946)).

According to a preferred embodiment, the nucleic acid(s) encoding a NADH oxidase or NOXE may be nucleic acid(s) selected from the group comprising *Streptococcus pneumoniae, Lactococcus lactis, Enterococcus faecalis, Lactobacillus brevis* and a mixture thereof, and preferably *Streptococcus pneumoniae*.

According to another preferred embodiment, the nucleic acid(s) encoding a NADH oxidase or NOXE may be nucleic acid(s) selected from the group consisting of sequences having at least 78%, preferably at least 80%, nucleic acid identity with the nucleic acid sequences SEQ ID NO: 21, 23, 25 and 27.

As described herein, a nucleic acid sequence having at least 78% nucleotide identity with a reference nucleic acid sequence encompasses nucleic acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence.

According to another particular embodiment, the nucleic acid(s) encoding a NADH oxidase may be nucleic acid(s) encoding an amino acid sequence selected from the group consisting of sequences having at least 78%, preferably at least 80%, identity with sequences SEQ ID NO: 22, 24, 26 and 28.

As described herein, an amino acid sequence having at least 78% amino acid identity with a reference amino acid sequence encompasses amino acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of NADH oxidase in the present invention is regulated by at least one promoter and at least one terminator, such as herein after defined more in details, which are respectively present in 5'- and -3' position of the nucleic acid sequence encoding the NADH oxidase.

In addition, the above-mentioned advantageous technical effects are linked to the expression level of said NADH oxidase. Indeed, and as it emerges from the herein after examples, not only the mere presence of a NADH oxidase is important but the level of NADH oxidase expression has also an extreme importance on acetoin production.

As above-mentioned, a recombinant yeast according to the invention has a reduced pyruvate decarboxylase activity, and in the genome of which has been inserted, notably, one or more copies of a nucleic acid encoding a NADH oxidase or NOXE.

In this regard, a recombinant yeast according to the invention may comprise notably from 1 to 20 copies of a nucleic acid encoding a NADH oxidase.

Preferably, a recombinant yeast according to the invention may comprise from 1 to 12, in particular from 2 to 5, preferably from 3 to 4, and better still equal to 3, copies of a nucleic acid encoding a NADH oxidase.

According to a particular embodiment, the DNA construct(s) of formulae (I) to (III) comprising at least the NOXE gene(s) may be inserted in the endogenous URA3 gene of said recombinant yeast.

In view of the above, each of nucleic acids encoding acetolactate synthase, acetolactate decarboxylase and NADH oxidase is under the control of a promoter and of a terminator so as to avoid unwanted regulation, notably such as herein after defined.

Promoter

For obvious reasons, each of nucleic acids encoding acetolactate synthase, acetolactate decarboxylase and NADH oxidase is under the control of a promoter, identical or different.

Said promoters, identical or different, allowing the constitutive over-expression of a given gene, may be found in literature (velculescu et al. (1997) Cell 88, 243-251).

Promoters more particularly interesting in the present invention may be selected from the group comprising:

pADH1 from gene coding for the alcool deshydrogenase (ADH1 gene=Sequence SEQ ID No 32), pTDH3 from gene coding for the Glyceraldehyde-3-phosphate dehydrogenase (TDH3 gene=Sequence SEQ ID No 39), pTEF2.K1 from the gene coding for the Translational elongation factor EF-1 alpha (TEF2 gene=Sequence SEQ ID No 30), pGPM1 from the gene coding for Glycerate Phospho-Mutase (GPM1 gene=Sequence SEQ ID No 33), pPDC1 from the gene coding for pyruvate decarboxylase (PDC1 gene=Sequence SEQ ID No 35), pENO2 from the gene coding for Enolase II (ENO2 gene=Sequence SEQ ID No 29), pTEF3 from the gene coding for the Gamma subunit of translational elongation factor eEF1B (TEF3 gene=Sequence SEQ ID No 31), pFBA1 from the gene encoding for the Fructose 1,6-bisphosphate aldolase II (FBA1 gene=Sequence SEQ ID No 34), pPGK1 from the gene encoding for the 3-phosphoglycerate kinase (PGK1 gene=Sequence SEQ ID No 36), pPYK1 from the gene encoding for the pyruvate kinase (PYK1 gene=Sequence SEQ ID No 49), pTPI1 from the gene encoding for the Triose Phosphate Isomerase (TPI1 gene=Sequence SEQ ID No 50), or pTEF1 from the gene coding for the Translational elongation factor EF-1 alpha (TEFL gene=Sequence SEQ ID No 38).

In addition, homologous promoters from other closely related yeasts can also be used as promoters form other yeast form the *Saccharomyces* genus, or yeast from other genus such as *Candida, Debaryomyces, Pichia* or *Kluveromyces*.

Synthetic promoters as described in Blazeck & Alper (2013) Biotechnol. J. 8 46-58 can also be used.

More particularly, said promoters, identical or different, may be preferably characterized by a sequence of nucleic acids selected from the group consisting of sequences having at least 80% nucleic acid identity with the nucleic acid sequences SEQ ID NO: 29 to 39, 49 and 50.

According to a particular embodiment, each of nucleic acids encoding acetolactate synthase, acetolactate decarboxylase and NADH oxidase is under the control of a transcription terminator, identical or different, said transcription terminators being characterized by a sequence of nucleic acid selected from the group consisting of sequences having at least 80% nucleic acid identity with the nucleic acid sequence of SEQ ID NO: 40 to 48.

Terminator

For obvious reasons, each of nucleic acids encoding acetolactate synthase, acetolactate decarboxylase and NADH oxidase is linked to a transcription terminator (which may be also termed "terminator" herein), identical or different.

Said transcription terminators, identical or different, may be found in literature Yamanishi et al., (2013) ACS synthetic biology 2, 337-347.

Terminators more particularly interesting in the present invention may be selected from the group comprising:
tTPI1 from the gene encoding for the Triose Phosphate Isomerase (TPI1 gene=Sequence SEQ ID No 44),
tMET25 from the gene encoding for the O-acetyl homoserine-O-acetyl serine sulfhydrylase (Met25 gene=Sequence SEQ ID No 45),
tADH1 from gene coding for the alcool deshydrogenase (ADH1 gene=Sequence SEQ ID No 43),
tENO2 from the gene coding for Enolase II (ENO2 gene=Sequence SEQ ID No 46),
tTDH2 from the gene coding for Glyceraldehyde-3-phosphate dehydrogenase, isozyme 2 (TDH2 gene=Sequence SEQ ID No 40),
tPGK1 from the gene encoding for the 3-phosphoglycerate kinase (PGK1 gene=Sequence SEQ ID No 48),
tCYC1 (=Sequence SEQ ID No 41),
tMET3 (=Sequence SEQ ID No 47), and
tTDH3 (=Sequence SEQ ID No 42), and
tDIT1 (=Sequence SEQ ID No 43).

More particularly, said terminator, identical or different, may be preferably characterized by a sequence of nucleic acid selected from the group consisting of sequences having at least 80% identity with sequences SEQ ID NO: 32 to 40 and 43.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus *Saccharomyces, CandidaAshbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* or *Malassezia*.

More preferentially, the yeast may be Crabtree positive yeast of genus of *Saccharomyces, Dekkera, Schizosaccharomyces, Kluyveromyces, Torulaspora Zigosaccharomyces*, or. *Brettanomycces*

More preferentially, the yeast may be from the species *Saccharomyces cerevisiae, Saccharomyces boulardii, Saccharomyces douglasii, Saccharomyces bayanus* or. or *Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa, Torulaspora glabrata*

More preferentially, the recombinant yeast may belong to the *Saccharomyces* genus, and preferably to the *Saccharomyces cerevisiae* species.

As above-mentioned, a recombinant yeast according to the invention has a pyruvate decarboxylase activity which is reduced by insertion of at least one DNA construct(s) selected from the group comprising formulae (I) to (III), and preferably of at least one of said DNA construct(s) comprising only at least one nucleic acid(s) encoding ALS and/or ALD.

According to a preferred embodiment, the recombinant yeast may be a recombinant *Saccharomyces cerevisiae* and the pyruvate decarboxylase activity is reduced by disruption of only two pdc genes. More preferably, the disrupted pdc gene(s) may be selected from the group consisting of pdc1, pdc5, pdc6 and a mixture thereof, and preferably of pdc1 and pdc6.

Methods implemented to insert a specific DNA construct within a gene, and more particularly a pyruvate decarboxylase gene, belong to the general knowledge of a man skilled in the art. A related method is described in more details in the herein after examples.

Most Preferred Embodiments

Advantageously, the nucleic acids encoding enzymes implemented in the present invention are advantageously chosen among ALS.Bs, ALS.Pp, ALD.L1, ALD.Ea, NOX-E.spn, NOXE.L1 and a mixture thereof.

According to a preferred embodiment, a recombinant yeast according to the present invention may be characterized in that it belongs to the *Saccharomyces* genus, in particular *Saccharomyces cerevisiae* species, wherein the endogenous pyruvate decarboxylase activity is reduced by disruption of at least two of pdc genes, in particular by disruption of pdc 1 and pdc 6 genes, wherein:
one of pdc genes, preferably the pdc 1 gene, is disrupted by insertion of a DNA construct of the formula (IIe) below:

$$5'\text{-}[(prom5)_{y1}\text{-}ALS.Bs\text{-}term5]_{x5}\text{-}[prom1\text{-}ALS.Bs\text{-}term1]_{x1}\text{-}[prom2\text{-}ALD.L1\text{-}(term2)_{z1}]_{x2}\text{-}3' \quad \text{(IIe), and}$$

the at least other pdc gene, distinct from the above-mentioned disrupted pdc gene, and preferably the pdc 6 gene, is disrupted by insertion of a DNA construct of the formula (IIf) below:

$$5'\text{-}[(prom5)_{y1}\text{-}ALS.Pp\text{-}term5]_{x5}\text{-}[prom1\text{-}ALS.Pp\text{-}term1]_{x1}\text{-}[prom2\text{-}ALD.Ea\text{-}(term2)_{z1}]_{x2}\text{-}3' \quad \text{(IIf)},$$

and wherein the DNA construct of following formula (IIf'):

$$5'\text{-}[(prom3)_{y2}\text{-}NOXE.L1\text{-}(term3)_{z2}]_{x3}\text{-}3' \quad \text{(IIf')},$$

is inserted in the URA3 gene,
wherein:
prom1, prom2, prom3, prom5, term1, term2, term3, term5, "y1", "y2", "z1" and "z2" are such as above-defined and ALS.Bs, ALS.Pp, ALD.L1, ALD.Ea and NOXE.L1 are such as defined in hereinafter Table 1,
each of "x1", "x2" and "x3", independently the ones of the others, represents an integer ranging from 0 to 50, preferably from 0 to 20, preferably from 0 to 10, more particularly from 0 to 3, and in particular equal to 1;
"x3" represents an integer ranging from 0 to 50, preferably from 0 to 20, preferably from 0 to 12, more particularly from 2 to 5, preferably from 3 to 4, and better still equal to 3,
provided that said recombinant yeast comprises at least one nucleic acid encoding for each ALS, ALD and NOXE, and more particularly provided that each DNA construct of formula (IIe) and (IIf) comprises each at least one nucleic acid encoding for each ALS and ALD.

In view of the above, and although it is implicitly disclosed, it is specifies that, between each formulae (IIe) and (IIf):

"x1" to "x3", "x5", "y1", "y2", "z1" and "z2"; and/or
the promoter and/or terminator for each copy of nucleic acid for a considered gene, may be identical or different.

According to a particular preferred embodiment, a recombinant yeast according to the present invention may be characterized in that it belongs to the *Saccharomyces* genus, in particular *Saccharomyces cerevisiae* species, wherein the endogenous pyruvate decarboxylase activity is reduced by disruption of at least two of pdc genes, in particular by disruption of pdc 1 and pdc 6 genes, wherein:

one of pdc genes, preferably the pdc 1 gene, is disrupted by insertion of a DNA construct of the formula (IIg) below:

$$5'-[ALS.Bs-tTDH2]_1-[pENO2-ALD.L1-tCYC1]_1-3' \qquad (IIg),$$

the at least other pdc gene, distinct from the above-mentioned disrupted pdc gene, and preferably the pdc 6 gene, is disrupted by insertion of a DNA construct of the formula (IIh') below:

$$5'-[pADH1-ALS.Pp-tDPI1]_1-[pTDH3-ALD.Ea-tMET25]_1-3'a \qquad (IIh')$$

and wherein the DNA construct of following formula (IIh"):

$$5'-[pENO2-NOXE.L1-tPGK1]_{12}-3' \qquad (IIh'')$$

is inserted in the URA3 gene,
wherein:
the "ALS.Bs" gene of DNA construct of formula (IIg) is under the control of the promoter of the pdc gene in which said DNA construct of formula (IIg) is inserted, pENO2, pADH1, pTDH3, tTDH2, tCYC1, tDPI1, tMET25 and tPGK1 are such as defined in the present description and more particularly in the hereinafter sequences listing,
ALS.Bs, ALS.Pp, ALD.L1, ALD.Ea and NOXE. L1 are such as defined in hereinafter table 1 and mode particularly in the hereinafter sequences listing.

According to a particular embodiment, the recombinant yeast according to the invention may be further modified to optimize acetoin production.

Use of Alternate Sources of Sugar:

The direct use of alternate source of sugar such as starch further requires the over expression in yeast of exogenous α-amylase and glucoamylase (buscke et al. biosource technology 2013).

Sugar Import—Improvement of C5 Sugar Import

The import of pentoses by recombinant microorganism is a major issue for industrial process since C5 sugars are major constituents of hydrolysed lignocellulosic biomass. Native strains of *S. cerevisiae*, like many other types of yeast, are unable to utilize either xylose or arabinose as fermentative substrates (Hahn-Hagerdal et al., 2007; Jin et al., 2004). Interestingly, it is able to uptake xylose even though the sugar is not a natural substrate (Hamacher et al., 2002).

*S. cerevisiae* GAL2, HXT1, HXT2, HXT4, HXT5, and HXT7 catalyze the uptake of xylose because they have a broad substrate specificity (Hamacher et al., 2002; Saloheimo et al., 2007; Sedlak & Ho 2004). However, their affinity for xylose is much lower than that for glucose and the xylose uptake by the transporters is strongly inhibited by glucose (Saloheimo et al., 2007).

Several changes are needed to obtain a strain able to grow and consume xylose and/or arabinose. These different modifications are a part of the invention.

Overexpression of Heterologous Xylose Transporters

In order to improve the xylose and arabinose uptake, the recombinant acetoin producer strain has to be modified to express heterologous genes coding for xylose or arabinose transporters. For example, genes GXF1, SUT1 and AT5g59250 from *Candida intermedia*, *Pichia stipitis* and *Arabidopsis thaliana*, respectively, are overexpressed to improve xylose utilization by the yeast (Runquist et al., 2010).

Overexpression of Pathways Involved in the Metabolism of Xylose and Arabinose

Yeast strains are able to take up xylose even though the sugar is not a natural substrate. Even though genes for xylose assimilation are present in *S. cerevisiae* they are not expressed at a sufficient level to enable significant sugar assimilation. Thus genetic modifications are necessary to improve the assimilation of pentose sugars. All enzymes that allow the transformation of xylose or arabinose to xylitol need to be enhanced as well as the enzymes which convert xylitol in xylulose, and xylulose into xylulose-5-phosphate. Either, the homologous genes from the xylose and arabinose pathways have to be overexpressed or heterologous genes from bacteria have to be overexpressed.

In one embodiment of the invention, the xylose uptake and its assimilation by the strain are improved by overexpressing for example:

1) Genes XYL1 or GRE3 coding the aldolase reductase of *P. stipitis* and *S. cerevisiae*, respectively, associated to overexpression of XYL2 encoding the xylitol dehydrogenase from *P. stipitis*, combined with the overexpression of genes XKS 1 or XYL3 encoding the xylulokinase from *S. cerevisiae* and *P. stipitis*, respectively, 2) The gene xylA encoding a xylose isomerase from bacteria or *Piromyces* associated to the overexpression of genes XKS1 or XYL3 encoding the xylulokinase from *S. cerevisiae* and *P. stipitis*, respectively.

In another embodiment of the invention, arabinose uptake and its assimilation by the strain are improved by overexpressing for example:

1) Homologous genes XYL1 or GRE3 coding the aldolase reductase of *P. stipitis* and *S. cerevisiae*, respectively, associated to ladl encoding the L-arabinitol 4-hydrogenase and Ixrl encoding a L-xylulose reductase from *Trichoderma reesei*, in combination with the overexpression of XYL2 encoding the xylitol dehydrogenase from *P. stipitis*, and in addition the overexpression of genes XKS1 or XYL 3 encoding the xylulokinase from *S. cerevisiae* and *P. stipitis*, respectively, 2) Heterologous genes araA and araB encoding bacterial arabinose isomerase and ribulose kinase.

Optimization of the Pentose Phosphate Pathway

This can be done by overexpressing at least one gene belonging to the non oxidative pentose phosphate pathway; TAL1, TKL1, RKL1 and RPE1 from the yeast strain.

Optimization of the availability of NAPDH cofactors required by the enzymes involved in the metabolism of C5-sugars This is attained by expressing the transhydrogenases of *E. coli* in the yeast strain. The genes udhA and or pntAB from *E. coli* will be overexpressed in the producer strain.

Prevention of the Glucose Consumption Towards Glycerol Synthesis:

This can be done by disrupting the GPD1 gene encoding the glycerol-3-phosphate dehydrogenase EC 1.1.1.8. (GPDH).

The present invention according to this embodiment is interesting notably in view of the yield in acetoin despite the fact that the disruption of the GPD1 gene leads to removing an enzyme activity which consumes NADH in favor of NAD. To counterbalance the redox disequilibrium thus generated, GPD1 disrupted strain may require additional expression of NOXE.

According to a particular embodiment, a recombinant strain according to the present invention is such that it does not comprise any genetic modification(s) which has the effect of reducing the glucose repression, as disclosed in WO 2011/041426 or Kim et al. (Bioresource Technology, vol. 146, 2013: 274).

According to a particular embodiment, a recombinant strain according to the present invention is such that it does not comprise any genetic modification(s) for allowing expressing any xylose assimilation pathways, as disclosed in Kim et al. (Journal of Biotechnology, 2014).

Culture Conditions

The present invention also relates to the use of a recombinant yeast such as above-defined, for the production of acetoin and/or derivatives thereof, in particular methyl vinyl Ketone (MVK).

The present invention further relates to a method of production of acetoin comprising the following steps:
  providing a recombinant microorganism as previously described, cultivating the recombinant microorganism in a culture medium containing a source of carbon, and recovering the acetoin.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the acetoin production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing acetoin according to the invention may further comprise, between steps (a) and (c), an intermediate step (b) consisting of cultivating the yeast cells in the said optimal culture medium.

Purification of Acetoin

According to a specific aspect of the invention, the fermentative production of acetoin comprises a step of isolation of the acetoin from the culture medium. Recovering the acetoin from the culture medium is a routine task for a man skilled in the art. It may be achieved by a number of techniques well known in the art including but not limiting to distillation, gas-stripping, pervaporation or liquid extraction. The expert in the field knows how to adapt parameters of each technique dependant on the characteristics of the material to be separated.

The yeast as model of microorganism in the present invention has been retained in that the synthesized acetoin is entirely exported outside the cells, thus simplifying the purification process.

The synthesized acetoin may be collected by distillation. Distillation may involve an optional component different from the culture medium in order to facilitate the isolation of acetoin by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane, dodecane.

Starting from acetoin that is produced by the recombinant yeast cells described in the present specification, acetoin derivatives, including methyl vinyl ketone, may be obtained through various methods that are well known by the one skilled in the art.

Throughout the description, including the claims, the expression "comprising a" should be understood as being synonymous with "comprising at least one", unless otherwise specified.

In addition, the expression "formulae (I) to (III), according to the considered context and unless contrary indications, means a DNA construct of formulae (I), (II) and (III) but also (IIa), (IIb), (IIc), (IId), (IIe), (IIf'), (IIf"), (IIg), (IIh') and/or (IIh").

The terms "between . . . and . . . " and "ranging from . . . to . . . " should be understood as being inclusive of the limits, unless otherwise specified.

The examples and figures which follow are presented by way of illustration and without implied limitation of the invention.

EXAMPLES a) Protocol for Making a Recombinant *Saccharomyces Cerevisiae* Strain According to the Invention All the hereinafter implemented recombinant *Saccharomyces cerevisiae* strains were constructed from the standard strain W303 (Thomas and Rothstein (1989), Cell. 56, 619-630) using standard yeast molecular genetics procedure (Methods in yeast Genetics—A cold spring harbor laboratory course Manual (2000) by D. Burke, D. Dawson, T. Stearns CSHL Press).

In these strains, pyruvate decarboxylase activity is reduced by disruption of at least one of the pdc genes (pdc1, pdc5, pdc6) or by replacement of their cognate transcription promoter by a weak promoter.

In the most efficient strains, only pdc1 and pdc6 were deleted.

A variety of exogenous enzymes were expressed in the considered recombinant *Saccharomyces cerevisiae* strains. They were chosen according to their Michaelis Menten enzymatic parameters when available (see herein after table 1). High kcat for high efficiency, and variety of Km to cover different concentration in substrate. *Paenibacillus polymyxa* enzymes were chosen because this organism is a natural 2,3 butane diol producer, a product directly derived from acetoin. Therefore it possesses enzymes that efficiently catalyse acetoin synthesis.

The genes nomenclature relatives to the implemented exogenous enzymes acetolactate synthase, acetolactate decarboxylase and water forming NADH oxydase is displayed in the hereinafter Table 1.

These genes are designated by the acronym of the enzyme followed by the acronym of the organism of origin as follows:

TABLE 1

| Enzyme | Gene | Organism | Km (mM) | kcat ($s^{-1}$) | Accession number |
| --- | --- | --- | --- | --- | --- |
| Acetolactate synthase E.C.2.2.1.6 (ALS) | ALS.Bs | *Bacillus subtilis* | 13 | 121 | YP008831756.1 |
| | ALS.Nt | *Nicotiana tabacum* | 11-16 | 3 | P09114.1 |
| | ALS.Pp | *Paenibacillus polymyxa* | — | — | YP003869749.1 |
| Acetolactate decarboxylase E.C.4.4.4.5 (ALD) | ALD.Bb | *Brevibacillus brevis* | 0.06 | — | YP002775372.1 |
| | ALD.Ea | *Enterobacter cloacae* | 10-13 | — | YP006476615.1 |
| | ALD.L1 | *Lactococcus lactis* | 10 | — | NP267263.1 |

TABLE 1-continued

| Enzyme | Gene | Organism | Km (mM) | kcat (s$^{-1}$) | Accession number |
|---|---|---|---|---|---|
| Water forming NADH Oxydase (NOX) | NOXE.L1 | *Lactococcus lactis* | | | YP003352913.1 |
| | NOXE.spn | *Streptococcus pneumonia* | | | YP002742271.1 |
| | NOXE.Ef | *Enterococcus faecalis* | | | NP815302.1 |
| | NOXE.Lb | *Lactobacillus brevis* | | | WP021742768.1 |

In addition, for a better comprehension of following genotypes:

ade2, his3, leu2, trp1 and ura3 are auxotrophy marker genes.

Lowercase letters mean that the considered gene is inactive, uppercase letters reflect an active gene.

"::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.

"gene.K1" means that the gene originates from *Kluyveromyces lactis*.

Transcription Promoters allowing the constitutive overexpression of a given gene are found in literature (velculescu et al. (1997) Cell 88, 243-251). Promoters herein used are designated by "p" followed by their cognate gene name. Their respective sequence number is also hereinafter mentioned.

Transcription terminators are also placed after each gene. To avoid unwanted regulation promoters and terminators framing one inserted gene were not taken from the same original gene. The terminators herein used are designated by "t" followed by their cognate gene name. Their respective sequence number is also hereinafter mentioned.

Cluster of above-mentioned genes were integrated in recombinant yeast at once using the ability of yeast to efficiently recombine free DNA ends which have sequence homology.

Recombinant yeast was obtained according to published methods available to the man of the art. Notably, it may be followed the method described in Shao et al. (Nucleic Acids Research, 2009, Vol. 37, No. 2: e16) and Shao et al. (Methods in Enzymology, 2012 Elsevier Inc., Vol. 517: 203), eventually with only minor variation.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit is then PCR amplified from the plasmids constructs, yielding X unit of linear DNA having overlapping sequences. One of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

b) Regarding the ALS and ALD Enzymes

ALS and ALD enzymes were not evaluated individually, but in pairs (ALS+ALD) through the yield of acetoin. Three exogenous ALD and ALS were chosen according to their kinetic parameters: ALS.Nt, ALS.Pp, ALS.Bs and ALD.Bb, ALD.L1, ALD.Ea (see above).

Eight of the nine possible combinations of ALS and ALD were conjointly inserted on the chromosome of a ura3-yeast strain behind promoters and followed by one terminator.

The insertion of these two genes disrupts the pdc1 gene. The URA3 marker gene is concomitantly inserted to select the transformant. ALS/ALD combination were inserted in strain YA747, namely a W303 derivative having the following genotype:

YA747: MAT-a, ade2, bdh1::TRP1.K1, his3, leu2, pdc1::HIS5.Sp, pdc6::LEU2.K1, trp1, ura3.

The following strains were constructed:

YA768: MAT-a, ade2, bdh1::TRP1.K1, his3, leu2, pdc1::[-ALS.Bs-tTPI1, pTDH3-ALD.Ea-tMET25, URA3.K1], pdc6::LEU2.K1, trp1, ura3

NB: in this case, the gene "ALS.Bs" is under the control of the natural promoter of pdc1, namely the promoter pPDC1.

YA769: MAT-a, ade2, bdh1::TRP1.K1, his3, leu2, pdc1::[-ALS.Nt-tTPI1, pTDH3-ALD.Ea-tMET25, URA3.K1], pdc6::LEU2.K1, trp1, ura3

YA770: MAT-a, ade2, bdh1::TRP1.K1, his3, leu2, pdc1::[-ALS.Pp-tTPI1, pTDH3-ALD.Ea-tMET25, URA3.K1], pdc6::LEU2.K1, trp1, ura3

YA771: MAT-a, ade2, bdh1::TRP1.K1, his3, leu2, pdc1::[-ALS.Nt-tTPI1, pTDH3-ALD.Bb-tMET25, URA3.K1], pdc6::LEU2.K1, trp1, ura3

YA772: MAT-a, ade2, bdh1::TRP1.K1, his3, leu2, pdc1::[-ALS.Nt-tTPI1, pTDH3-ALD.L1-tMET25, URA3.K1], pdc6::LEU2.K1, trp1, ura3

YA773: MAT-a, ade2, bdh1::TRP1.K1, his3, leu2, pdc1::[-ALS.Pp-tTPI1, pTDH3-ALD.L1-tMET25, URA3.K1], pdc6::LEU2.K1, trp1, ura3

YA810: MAT-a, ade2, bdh1::TRP1.K1, his3, leu2, pdc1::[-ALS.Bs-tTPI1, pTDH3-ALD.Bb-tMET25, URA3.K1], pdc6::LEU2.K1, trp1, ura3

YA811: MAT-a, ade2, bdh1::TRP1.K1, his3, leu2, pdc1:: [-ALS.Pp-tTPI1, pTDH3-ALD.Bb-tMET25, URA3.K1], pdc6::LEU2.K1, trp1, ura3

All these strains were grown for 24 hours in 8% glucose YPA (Yeast Extract 1%, Bacto peptone 2%, adenine 0.1 mM, glucose 8%). They were harvested and acetoin and ethanol content was determined according to standard methods with specificity adapted from in Gonzales et al. (2010), Applied and environmental Microbiology 76 670-679.

For some strains, several clones were assayed, the last number after the "-" is the clone number. Note that as the endogenous bdh enzyme is disrupted, no 2,3-BDO is produced.

The ethanol and acetoin production are monitored following standard methods and Gonzales et al. (2010), Applied and environmental Microbiology 76 670-679.

Results

Table 2 hereinafter displays the acetoin production of the above-mentioned tested strains.

TABLE 2

| Strains | Ethanol (g/l) | Acetoin (g/l) | ALS | ALD |
|---|---|---|---|---|
| YA747-8 | 32.2 | 0.2 | | |
| YA772-6 | 31.4 | 0.6 | Nt | Ll |
| YA772-10 | 29.5 | 1.2 | Nt | Ll |
| YA773-3 | 31.8 | 0.2 | Pp | Ll |
| YA810-1 | 32.3 | 0.2 | Bs | Bb |
| YA768-4 | 31.1 | 1.0 | Bs | Ea |
| YA768-7 | 31.0 | 2.1 | Bs | Ea |
| YA770-6 | 25.5 | 4.85 | Pp | Ea |
| YA770-12 | 21.8 | 6.7 | Pp | Ea |
| YA811-4 | 19.8 | 6 | Pp | Bb |
| YA811-5 | 21.15 | 5.75 | Pp | Bb |
| YA771-5 | 20.6 | 5.5 | Nt | Bb |
| YA769-1 | 22.25 | 6.05 | Nt | Ea |
| YA769-8 | 25.65 | 4.4 | Nt | Ea |

From these results, it may be concluded that, taken separately, the best enzymes to enhance acetoin production are ALS Pp, ALS Nt, ALD Ea and ALD Bb which indeed appears as being the most efficient enzyme.

c) The Advantageous Technical Effect of the NOXE Enzyme on the Acetoin Yield

A recombinant yeast according YA1609 has been prepared.

YA1609: MAT-a, his3, leu2, pdc1::[-ALS.Bs-tTDH2, pENO2-ALD.L1-tCYC1, HIS5.Sp], pdc6:: [pADH1-ALS.Pp-tDPI1, pTDH3-ALD.Ea-tMET25, LEU2.K1], trp1, ura3:: [pENO2-NOXE.L1-tPGK1, URA3]x12

YA1609-1, YA1609-2 and YA1609-4 are different clones from this strain YA1609.

It is noticed that these recombinant yeast always have their natural endogenous BHH activity.

These strains were then assayed for acetoin production in 16% glucose YPA (Yeast Extract 1%, Bacto peptone 2%, adenine 0.1 mM, glucose 8%) under the same condition than above described.

The ethanol and acetoin production are monitored following standard methods and Gonzales et al. (2010), Applied and environmental Microbiology 76 670-679.

Results

Results are reported in table 3 hereinafter.

TABLE 3

| Strain | Glucose (%) | Time (Hour) | Optical density (650 nm) | Ethanol (g/l) | Acetoin (g/l) |
|---|---|---|---|---|---|
| YA1609-1 | 16% | 32 | 107.7 | 0.0 | 59.8 |
| | | 48 | 112.0 | 0.0 | 64.8 |
| YA1609-2 | 16% | 32 | 104.2 | 0.0 | 58.4 |
| | | 48 | 103.6 | 0.0 | 61.2 |
| YA1609-4 | 16% | 32 | 113.2 | 0.0 | 58.8 |
| | | 48 | 111.2 | 0.0 | 65.6 |

These results show that the presence of NOXE leads to a very significative accumulation of acetoin.

YA1609-4 is now implemented in a same culture medium than above-mentioned. The present assay however differs by the following parameters:

Milieu: 0.5 l YPA, 16% glucose.

16 hours after the starting of the cell culture, cells were incubated in a culture medium comprising a final concentration of 16% w/w glucose for a time period of 8 hours.

Stirring: 800 rpm (2 pales), 1.9 ms$^{-1}$

Temperature: 30° C.

Air: 0.15 L/min (0.3 vvm)

The cells were then assayed for acetoin production. The ethanol and acetoin production are monitored following standard methods and Gonzales et al. (2010), Applied and environmental Microbiology 76 670-679.

Results

Results are reported in table 4 hereinafter.

TABLE 4

| Strain | Time (Hour) | Optical density (650 nm) | Ethanol (g/l) | Acetoin (g/l) |
|---|---|---|---|---|
| YA1609-4 | 24 | 76.5 | 6.1 | 51.8 |
| | 32 | 76.3 | 8.1 | 64.2 |
| | 48 | 73.6 | 8.0 | 75.2 |
| | 56 | 70.2 | 8.4 | 80.2 |
| | 72 | 71.0 | 7.9 | 81.2 |

These results show that the considered culture parameters may also influence the acetoin production.

d) Further Examples of Recombinant Yeasts Producing Acetoin

Further recombinant yeasts have been prepared, which are described hereunder.

YA1573-4: MAT-a, his3, leu2, pdc1::[-ALS.Bs-tTDH2, pENO2-ALD.L1-tCYC1, HIS5.Sp], pdc6:: [pADH1-ALS.Pp-tDPI1,pTDH3-ALD.Ea-tMET25,pTEF2-TRP1.Sc-tADH1,pGMP1-BDH.Sc-tENO2], trp1, ura3:: [pENO2-NOXE.L1-tPGK1, URA3]x12

YA1609-4: MAT-a, his3, leu2, pdc1:: [-ALS.Bs-tTDH2, pENO2-ALD.L1-tCYC1, HIS5.Sp], pdc6:: [pADH1-ALS.Pp-tTPI1, pTDH3-ALD.Ea-tMET25, LEU2.K1], trp1, ura3:: [pENO2-NOXE.L1-tPGK1, URA3]x12

YA1661-2: MAT-a, his3, leu2, pdc1:: [-ALS.Bs-tTDH2, pENO2-ALD.L1-tCYC1, HIS5.Sp], pdc6:: [pADH1-ALS.Pp-tTPI1, pTDH3-ALD.Ea-tMET25, pENO2-NOXE.Spn-tPGK1], trp1, ura3:: [pENO2-NOXE.L1-tPGK1, URA3]x12.

It is noticed that these recombinant yeast always have their natural endogenous BHH activity.

These strains were then assayed for acetoin production in 16% glucose YPA (Yeast Extract 1%, Bacto peptone 2%, adenine 0.1 mM, glucose 8%) under the same condition than above described.

The ethanol and acetoin production are monitored following standard methods and Gonzales et al. (2010), Applied and environmental Microbiology 76 670-679.

Results

The results are reported in table 5 hereinafter.

TABLE 5

| Stains | Conditions | Time (Hour) | Optical density (650 nm) | Ethanol (g/l) | Acetoin (g/l) |
|---|---|---|---|---|---|
| YA1573-4 | YPA | 40 H | 87.2 | 0 | 49.9 |
| YA1609-4 | 16% | | 92.3 | 0 | 58.3 |
| YA1661-2 | Glucose | | 97.0 | 0 | 63.9 |

These results of Table 5 show that the presence of a plurality of nucleic acids encoding NOXE in the recombinant yeast leads to an increased accumulation of acetoin, as compared to the recombinant yeasts transformed with a single nucleic acid encoding NOXE.

e) Prevention of the Escape of Acetoin Towards 2,3-BDO

At least one gene(s) among the following endogenous bdh1, bdh2, adh1, adh3 and/or adh4 genes may be inactivated. In some strains the auxotrophy markers have been reintroduced to render them prototroph. They all have the same promoters and terminators than YA1660:

YA1660-2, YA1660-3, YA1660-4, and YA1711-16C: MAT-a, his3, leu2, pdc1::[-ALS.Bs-tTDH2, pENO2-ALD.L1-tCYC1, HIS5.Sp], pdc6:: [pADH1-ALS.Pp-tTPI1, pTDH3-ALD.Ea-tMET25, pENO2-NOXE.Spn-tPGK1, LEU2.K1], trp1, ura3:: [pENO2-NOXE.L1-tPGK1, URA3]x12.

YA1711-45c: Mat-α, his3, leu2, pdc1::[-ALS.Bs-tTDH2, pENO2-ALD.L1-tCYC1, HIS5.Sp], pdc6:: [pADH1-ALS.Pp-tTPI1, pTDH3-ALD.Ea-tMET25, pENO2-NOXE.Spn-tPGK1, LEU2.K1], trp1, ura3:: [pENO2-NOXE.L1-tPGK1, URA3]x12

YA1711-13A, YA1711-16B: Mat-a, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA1711-19A and YA1711-46A: Mat-a, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA1822-1 and YA1822-2: Mat-a, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1:: TRP1, ura3:: [NOXE.L1-URA3]x12

YA 1870-10A: Mat-a, adh3::TRP1.K1, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA 1870-11B: Mat-a, adh3::TRP1.K1, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA1870-10B: Mat-a, adh1::TRP1.K1, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA1870-11A: Mat-a, adh1::TRP1.K1, bdh1::LEU2.K1, bdh2::HIS5.Sp, his3, leu2, pdc1:: [ALS.Bs-ALD.L1-HIS5.Sp], pdc6:: [ALS.Pp-ALD.Ea-NOXE.Spn-LEU2.K1], trp1, ura3:: [NOXE.L1-URA3]x12

YA1870-2A and YA1870-3D: Mat-a, adh1::TRP1.K1, adh3::TRP1.K1, bdh1::LEU2.K1, bdh2::HIS5.Sp, his3, leu2, pdc1:: [ALS.Bs-ALD.L1-HIS5.Sp-loxP], pdc6:: [ALS.Pp-ALD.Ea-NOXE.Spn-LEU2.K1-loxP], trp1, ura3:: [NOXE.L1-URA3]x12

All the above described strains as well as YA1609-4 and YA1661-2 and diploids combination of these strains should be considered as strains having an improved acetoin yield.

f) Further Examples Showing Prevention of the Escape of Acetoin Towards 2,3-BDO

Strain YA1711-19A has been grown in a 3l fermentor in Yeast extract 2%, sucrose 10%, from 0 to 24 hours, then 600 g of glucose was slowly added (30 g/l for 20 hours)

| Strain | Time (Hours) | Optical Density (650 nm) | Ethanol (g/L) | Acetoin (g/L) | RR 2,3 butanediol (g/L) | MESO (g/L) | RR 2,3 butanediol + MESO (g/L) |
|---|---|---|---|---|---|---|---|
| YA1711-19A | 24 | 99 | 7.5 | 76.1 | 0.1 | 1.1 | 1.1 |
| | 32 | 99 | 7.2 | 115.7 | 0.6 | 2.2 | 2.8 |
| | 48 | 96 | 9.2 | 128.9 | 0.9 | 3.8 | 4.7 |
| | 55 | 93 | 8.8 | 125 | 0.9 | 4.7 | 5.5 |

The following strains, which all consist of strains in which exogenous ALS, ALD and NOXE have been introduced, were incubated in 500 ml Erlenmeyer flasks and shaken for 24 h and 48 h at 30° C. in Yeast extract 2% and sucrose 30%:

| Strains | Conditions | Optical Density at 24 H (650 nm) | Optical Density at 48 H (650 nm) | Ethanol (g/L) | Acetoin (g/L) | 2,3-BDO (g/L) |
|---|---|---|---|---|---|---|
| YA1711-19A | YE 2%, Sucrose 30% | 89 | 107 | ILQ | 115.4 | 2.2 |
| YA1763-1 | | 96 | 116 | 29.9 | 102.6 | 3.7 |
| YA1763-3 | | 33 | 38 | ILQ | 34 | 1.7 |
| YA1763-4 | | 93 | 113 | 28 | 108.2 | 3.6 |
| YA1822-1 | | 93 | 111 | 27.7 | 95.3 | 2.8 |
| YA1822-2 | | 95 | 115 | 30.3 | 95.5 | 2.9 |
| YA1822-3 | | 101 | 115 | 29.7 | 99.7 | 3 |
| YA1822-4 | | 74 | 86 | ILQ | 117.9 | 2 |

| Strains | Conditions | Optical Density at 24 H (650 nm) | Optical Density at 48 H (650 nm) | Ethanol (g/L) | Acetoin (g/L) | 2,3-BDO (g/L) |
|---|---|---|---|---|---|---|
| YA1835-3 | | 88 | 120 | ILQ | 121.2 | 3.8 |
| YA1835-6 | | 94 | 120 | 22 | 111.88 | 3.31 |

SEQUENCE LISTING

SEQ ID No 1 (=ADN ALS.Bs)
ATGTCTACCAAAGCAACAAAAGAGCAAAAGAGCCTTGTGAAGAATAGAGG
TGCAGAACTTGTCGTTGATTGCTTGGTAGAACAGGGAGTCACTCACGTTT
TCGGGATACCCGGCGCTAAAATCGACGCCGTGTTTGACGCTTTACAGGAT
AAGGGACCAGAGATCATTGTTGCTAGACATGAACAGAATGCAGCGTTCAT
GGCTCAAGCTGTAGGTAGACTTACTGGGAAACCCGGTGTGGTTTTGGTTA
CTAGTGGACCAGGTGCATCAAATCTAGCAACAGGTTTGTTAACAGCGAAT
ACAGAGGGAGATCCTGTTGTTGCATTAGCAGGAAACGTTATCAGAGCGGA
TAGACTGAAAAGAACCCATCAATCATTGGATAATGCTGCATTATTTCAGC
CAATTACGAAATATTCCGTCGAAGTACAGGATGTGAAGAACATACCTGAA
GCTGTAACTAATGCGTTTCGTATAGCTTCTGCTGGTCAAGCTGGTGCAGC
TTTTGTTTCGTTTCCGCAAGACGTTGTCAACGAGGTTACGAACACTAAGA
ATGTGAGAGCAGTAGCAGCCCCAAAATTAGGACCAGCTGCTGATGATGCT
ATATCAGCTGCTATTGCTAAGATTCAGACAGCCAAACTACCTGTTGTCTT
AGTAGGTATGAAAGGTGGCAGGCCAGAAGCAATCAAGGCAGTTAGAAAAC
TGTTGAAGAAGGTTCAATTGCCGTTTGTGGAAACCTATCAAGCCGCAGGG
ACTTTGTCTAGGGATCTAGAAGATCAATACTTCGGTAGAATAGGGTTGTT
CAGAAATCAACCTGGCGACTTGTTACTGGAACAAGCCGATGTCGTGCTTA
CAATTGGTTACGATCCGATTGAATATGACCCCAAATTTTGGAATATTAAT
GGTGATAGGACTATTATCCACTTAGACGAGATTATTGCCGATATTGACCA
TGCTTATCAACCTGATCTGGAACTGATAGGTGATATTCCAAGTACTATCA
ACCATATAGAGCATGATGCCGTCAAAGTGGAATTTGCCGAAAGAGAACAG
AAGATCCTATCCGATCTAAAGCAGTACATGCATGAAGGCGAACAAGTTCC
AGCAGATTGGAAATCCGATAGAGCACATCCATTGGAAATTGTCAAAGAAT
TGAGAAATGCAGTTGATGACCATGTTACAGTTACTTGTGACATAGGTAGT
CACGCTATTTGGATGTCTAGGTACTTCAGATCTTATGAGCCATTAACGTT
GATGATATCCAATGGCATGCAAACCCTTGGAGTCGCTTTACCATGGGCCA
TTGGTGCGTCGTTAGTAAAGCCAGGAGAGAAAGTCGTTTCTGTGTCAGGT
GATGGTGGTTTCTTGTTCTCTGCCATGGAATTGGAAACCGCCGTTCGTTT
GAAAGCCCCTATAGTACACATCGTGTGGAATGATTCGACTTATGACATGG
TCGCGTTTCAACAATTGAAGAAGTACAACCGTACTTCAGCTGTTGATTTC
GGCAACATTGACATTGTGAAGTACGCCGGAAAGCTTTGGCGCCACAGGCCT
AAGAGTCGAATCACCTGATCAATTAGCAGATGTACTTAGGCAAGGGATGA
ACGCTGAAGGACCTGTAATTATCGACGTACCTGTTGACTATAGCGACAAC
ATCAATTTAGCCAGTGATAAATTACCCAAAGAGTTTGGTGAGCTAATGAA
AACGAAAGCTTTGTAA

SEQ ID No 2 (=Amino acid ALS.Bs)
MSTKATKEQKSLVKNRGAELVVDCLVEQGVTHVFGIPGAKIDAVFDALQD
KGPEIIVARHEQNAAFMAQAVGRLTGKPGVVLVTSGPGASNLATGLLTAN
TEGDPVVALAGNVIRADRLKRTHQSLDNAALFQPITKYSVEVQDVKNIPE
AVTNAFRIASAGQAGAAFVSFPQDVVNEVTNTKNVRAVAAPKLGPAADDA
ISAAIAKIQTAKLPVVLVGMKGGRPEAIKAVRKLLKKVQLPFVETYQAAG
TLSRDLEDQYFGRIGLFRNQPGDLLLEQADVVLTIGYDPIEYDPKFWNIN
GDRTIIHLDEIIADIDHAYQPDLELIGDIPSTINHIEHDAVKVEFAEREQ
KILSDLKQYMHEGEQVPADWKSDRAHPLEIVKELRNAVDDHVTVTCDIGS
HAIWMSRYFRSYEPLTLMISNGMQTLGVALPWAIGASLVKPGEKVVSVSG
DGGFLFSAMELETAVRLKAPIVHIVWNDSTYDMVAFQQLKKYNRTSAVDF
GNIDIVKYAESFGATGLRVESPDQLADVLRQGMNAEGPVIIDVPVDYSDN
INLASDKLPKEFGELMKTKAL SEQ ID No 3 (=ADN ALS.Nt)
ATGGCTGCTGCTGCAGCTGCTCCATCTCCATCTTTTTCTAAAACCTTGTC
CTCCTCCTCTTCCAAATCTTCTACTTTGTTGCCAAGATCTACTTTCCCAT
TTCCACATCATCCACATAAGACTACTCCACCACCATTGCATTTGACTCCA
ACTCATATTCACTCCCAAAGAAGAAGATTCACCATCTCCAACGTTATTTC
TACCACCCAAAAGGTTTCTGAAACTCAAAAGGCTGAAACCTTCGTTTCTA
GATTTGCTCCAGATGAACCTAGAAAGGGTTCTGATGTTTTGGTTGAAGCT
TTGGAAAGAGAAGGTGTTACCGATGTTTTTGCTTATCCAGGTGGTGCTTC
TATGGAAATTCATCAAGCTTTGACCAGATCCTCCATCATTAGAAATGTTT
TGCCAAGACATGAACAAGGTGGTGTTTTCGCTGCTGAAGGTTATGCTAGA
GCTACTGGTTTTCCAGGTGTATGTATTGCTACTTCTGGTCCAGGTGCTAC
TAATTTGGTTTCTGGTTTGGCTGATGCTTTGTTGGATTCTGTTCCAATCG
TTGCTATTACTGGTCAAGTTCCAAGAAGAATGATTGGTACAGATGCTTTC
CAAGAAACCCCAATTGTCGAAGTTACTAGATCTATTACCAAGCACAACTA
CTTGGTTATGGACGTTGAAGATATCCCAAGAGTTGTTAGAGAAGCATTTT TCTTGGCTAGATCTGGTAGACCAGGTCCAGTTTTGATTGATGTTCCAAAG
GATATCCAACAACAATTGGTTATCCCAGATTGGGACCAACCTATGAGATT
GCCAGGTTATATGTCTAGATTGCCAAAGTTGCCAAACGAAATGTTGTTAG
AACAAATCGTCAGATTGATCTCCGAATCTAAAAAGCCAGTCTTGTATGTT
GGTGGTGGTTGTTCTCAATCTAGTGAAGAATTGAGAAGATTCGTCGAATT
GACCGGTATTCCAGTTGCTTCTACATTGATGGGTTTGGGTGCTTTTCCAA
CTGGTGATGAATTGTCTTTGTCTATGTTGGGTATGCACGGTACTGTTTAT
GCTAATTACGCTGTTGATTCCTCCGATTTGTTGTTAGCTTTTGGTGTTAG
ATTCGATGATAGAGTCACTGGTAAGTTGGAAGCTTTTGCTTCTAGAGCTA
AGATCGTTCATATCGACATTGATTCCGCTGAAATCGGTAAAAACAAGCAA
CCACATGTTTCTATTTGCGCCGATATTAAGTTGGCATTGCAAGGTTTGAA
CAGTATCTTGGAATCCAAAGAAGGTAAATTGAAGTTGGACTTCTCTGCTT
GGAGACAAGAATTGACAGTTCAAAAGGTTAAGTACCCATTGAACTTCAAG
ACTTTCGGTGATGCTATTCCACCACAATACGCTATTCAAGTTTTGGATGA
ATTGACCAACGGTTCCGCTATTATTTCAACTGGTGTTGGTCAACATCAAA
TGTGGGCTGCTCAATATTACAAGTACAGAAAACCTAGACAATGGTTGACT
TCTGGTGGTTTAGGTGCTATGGGTTTTGGTTTGCCAGCTGCTATTGGTGC
TGCTGTTGGTAGACCTGATGAAGTTGTTGTAGATATTGATGGTGACGGTT
CCTTCATTATGAACGTCCAAGAATTGGCTACCATCAAGGTTGAAAATTTG
CCAGTCAAGATCATGTTATTGAACAATCAACACTTGGGTATGGTCGTCCA
ATGGGAAGATAGATTTTACAAAGCTAATAGAGCCCACACCTACTTGGGTA
ATCCATCTAATGAAGCTGAAATCTTCCCAAACATGTTGAAGTTTGCTGAA
GCTTGTGGTGTTCCAGCTGCAAGAGTTACTCATAGAGATGATTTGAGAGC
TGCCATCCAAAAGATGTTGGATACTCCAGGTCCATACTTGTTGGATGTTA
TTGTCCCACATCAAGAACATGTCTTGCCAATGATTCCATCTGGTGGTGCC
TTTAAAGATGTTATTACTGAAGGTGACGGTAGATCCTCTTACTGA SEQ ID No 4 (=Amino acid ALS.Nt)
MAAAAAAPSPSFSKTLSSSSSKSSTLLPRSTFPFPHHPHKTTPPPLHLTP
THIHSQRRRFTISNVISTTQKVSETQKAETFVSRFAPDEPRKGSDVLVEA
LEREGVTDVFAYPGGASMEIHQALTRSSIIRNVLPRHEQGGVFAAEGYAR
ATGFPGVCIATSGPGATNLVSGLADALLDSVPIVAITGQVPRRMIGTDAF
QETPIVEVTRSITKHNYLVMDVEDIPRVVREAFFLARSGRPGPVLIDVPK
DIQQQLVIPDWDQPMRLPGYMSRLPKLPNEMLLEQIVRLISESKKPVLYV
GGGCSQSSEELRRFVELTGIPVASTLMGLGAFPTGDELSLSMLGMHGTVY
ANYAVDSSDLLLAFGVRFDDRVTGKLEAFASRAKIVHIDIDSAEIGKNKQ
PHVSICADIKLALQGLNSILESKEGKLKLDFSAWRQELTVQKVKYPLNFK
TFGDAIPPQYAIQVLDELTNGSAIISTGVGQHQMWAAQYYKRKPRQWLT
SGGLGAMGFGLPAAIGAAVGRPDEVVVDIDGDGSFIMNVQELATIKVENL
PVKIMLLNNQHLGMVVQWEDRFYKANRAHTYLGNPSNEAEIFPNMLKFAE
ACGVPAARVTHRDDLRAAIQKMLDTPGPYLLDVIVPHQEHVLPMIPSGGA
FKDVITEGDGRSSY SEQ ID No 5 (=ADN ALS.Pp)
ATGTCCGCACAAATACCTGAAGTTAGAAGTACAAATGAATTGAGAGAAAA
ATGGATGAAGCCTGAAGTAATCACTGGTTCCGAAATATTGTTAAGATCAT
TGTTATTGGAAGGTGTCGATTGTGTATTTGGTTATCCAGGTGGTGCTGTC
TTGTACATCTATGATGCAATGTACGGTTTTAAAGACTTCAAGCATGTTTT
AACCAGACACGAACAAGGTGCTATACATGCTGCAGATGGTTATGCCAGAG
CTTCCGGTAAAGTAGGTGTTTGCATCGCAACAAGTGGTCCAGGTGCCACC
AATTTGGTTAGTGGTCTGGCAGACGCCCTTTTATGGATTCTGTTCCTTTGGT
TGTCATTACTGGTCAACGTCATTTCTTCATTAATCGGTACAGATGCATTCC
AAGAAGCCGACATAACTGGTATCACAATGCCAATAACTAAGCACTCATAT
TTGGTTAGAGATGTCGAAGACTTGCCTAGAATAATCCATGAAGCATTTCA
CATAGCAAATACAGGTAGAAAGGGTCCAGTTTTGATAGATATCCCTAAAG
ACATATCCGCCGCTCAAACCTTATTCGTACCACAAACCGGTCCTGTTACT
ATGAGAGGTTACACCCAAAGGTTTTGCCTAACAAGATACAATTGGATAAA
ATTGACACAAGCCATCTCCGAAGCTGAAAGACCATTCATTTTGGCAGGTG
GTGGTGTAGTTTATAGTGGTGGTCTGATGAAGCCTTATACGAATTTGTTAGA
AAGACTGAAATCCCTATCACTACAACCTTATTGGGTTTAGGTGGTTTCCC
ATCAGGTCATGAATTGTGGACTGGTATGCCTGGTATGGTTACATACA
CCTCCAATCAAGCAATACAACAATCTGATTTGTTGATCTGTATTGGTGCT
AGATTTGATGACAGAGTTACTGGTAAATTGGATGGTTTCGCACCACAAGC
CAAAATTGTACATATAGATATCGACCCTGCAGAAATAGGTAAAAATGTTG
CAGCCGATATTCCAATAGTAGGTGACGTTAAGGCTGTCTTAGAATTATTG

SEQUENCE LISTING

AACCAAGATGTTAAGAGAGCCGATAGAGCTGACGCATGGAGAGCACAAAT
CCAACATTGGAAGAACGAAAAGCCATATTCCTACAAGGATAGTGAAACAG
TTTTGAAACCTCAATGGGTCGTAGAATTATTGGATGAAACTACAAAGGGT
GGTGCTATTGTCACCACTGACGTAGGTCAACACCAAATGTGGGCTGCACA
ATACTACAAGTTTAATCAACCAAGATCATGGGTTACATCAGGTGGTTTAG
GTACTATGGGTTTTGGTTTCCCATCTGCTATTGGTGCACAAATGGCCAAT
CCTGATAGATTGGTTATCTCTATTAACGGTGACGGTGGTATGCAAATGTG
TTCACAAGAATTAGCTATTTGCGCTATTAATAACATCCCAGTAAAGATCG
TTATCATTAATAACCAAGTTTTGGGTATGGTCAGACAATGGCAAGAATTG
ATCTATAACAACAGATACTCTCATATTGATTTGGCTGGTTCACCTGACTT
TGTCAAATTGGCCGAAGCCTATGGTGTAAAGGGTTTAAGAGCAACCAATA
AGGAAGAAGCCAGAAGAGCTTGGCAAGAAGCATTGGATACTCCAGGTCCT
GTTGTCGTAGAATTTGTTGTCTCTAAAGAAGAAACGTTTATCCAATGGT
TACACAAGGTTCCACAATAGACCAAATGTTGATGGGTGACGAATGA

SEQ ID No 6 (=Amino acid ALS.Pp)
MSAQIPEVRSTNELREKWMKPEVITGSEILLRSLLLEGVDCVFGYPGGAV
LYIYDAMYGFKDFKHVLTRHEQGAIHAADGYARASGKVGVCIATSGPGAT
NLVTGIATAFMDSVPLVVITGNVISSLIGTDAFQEADITGITMPITKHSY
LVRDVEDLPRIIHEAFHIANTGRKGPVLIDIPKDISAAQTLFVPQTGPVT
MRGYNPKVLPNKIQLDKLTQAISEAERPFILAGGGVVYSGGHEALYEFVR
KTEIPITTTLLGLGGFPSGHELWTGMPGMHGTYTSNQAIQQSDLLICIGA
RFDDRVTGKLDGFAPQAKIVHIDIDPAEIGKNVAADIPIVGDVKAVLELL
NQDVKRADRADAWRAQIQHWKNEKPYSYKDSETVLKPQWVVELLDETTKG
GAIVTTDVGQHQMWAAQYYKFNQPRSWVTSGGLGTMGFGFPSAIGAQMAN
PDRLVISINGDGGMQMCSQELAICAINNIPVKVIINNQVLGMVRQWQEL
IYNNRYSHIDLAGSPDFVKLAEAYGVKGLRATNKEEARRAWQEALDTPGP
VVVEFVVSKEENVYPMVTQGSTIDQMLMGDE SEQ ID No 7 (=ADN ALD.Bb)
ATGGGTAAGAAGAACATTATTACCTCTATCACCTCCTTGGCTTTGGTTGC
TGGTTTGTCTTTGACTGCTTTTGCTGCTACTACTGCTGTTCCAGCTC
CACCAGCTAAACAAGAATCTAAACCAGCTGTTGCTGCTAATCCAGCTCCT
AAGAATGTTTTGTTCCAATACTCTACCATCAACGCCTTGATGTTGGGTCA
ATTTGAAGGTGATTTGACCTTGAAGGACTTGAAGTTGAGAGGTGATATGG
GTTTGGGTACTATCAATGATTTGGACGGTGAAATGATCCAAATGGGTACT
AAGTTCTACCAAATCGATTCTACCGGTAAGTTGTCTGAATTGCCAGAATC
TGTTAAGACTCCATTCGCTGTTACTACTCACTTCGAACCTAAGGAAAAGA
CTACCTTGACCAACGTCCAAGACTACAATCAATTGACCAAGATGTTGGAA
GAAAAGTTCGAAAACAAGAACGTTTTCTACGCCGTTAAGTTGACTGGTAC
TTTCAAAATGGTTAAGGCTAGAACCGTTCCTAAGCAACATAGACATATT
CACAATTGACTGAAGTCACCAAGAAGCAATCCGAATTTGAATTCAAGAAC
GTCAAGGGTACTTTGATCGGTTTTTACACTCCAAATTATGCTGCTGCTTTT
GAACGTTCCAGGTTTTCACTTGCATTTCATTACCGAAGATAAGACCTCTG
GTGGTCATGTTTTGAACTTGCAATTTGATAACGCCAATCTTGGAAATTCC
CCAATCCATGAATTTGATGTTCAATTGCCACACACCGATGATTTCGCTCA
TTCTGATTTGACTCAAGTTACTACCTCCCAAGTTCATCAAGCTGAATCTG
AAAGAAAGTA SEQ ID No 8 (=Amino acid ALD.Bb)
MGKKNIITSITSLALVAGLSLTAFAATTATVPAPPAKQESKPAVAANPAP
KNVLFQYSTINALMLGQFEGDLTLKDLKLRGDMGLGTINDLDGEMIQMGT
KFYQIDSTGKLSELPESVKTPFAVTTHFEPKEKTTLTNVQDYNQLTKMLE
EKFENKNVFYAVKLTGTFKMVKARTVPKQTRPYPQLTEVTKKQSEFEFKN
VKGTLIGFYTPNYAAALNVPGFHLHFITEDKTSGGHVLNLQFDNANLEIS
PIHEFDVQLPHTDDFAHSDLTQVTTSQVHQAESERK SEQ ID No 9 (=ADN ALD.Ea)
ATGATGATGCACTCCTCCGCCTGCGACTGTGAAGCAAGTTTATGCGAAAC
ATTGAGAGGTTTTTCCGCCAAGCACCCAGATTCCGTTATATATCAAACAT
CCTTGATGAGTGCTTTGTTTATCTGGTGTCTACGAAGGTGACACTACAATT
GCAGACTTGTTAGCTCATGGTGACTTTGGTTTGGGTACTTTTAATGAATT
AGACGGTGAAATGATCGCATTTCTTCACAAGTTTACCAATTGAGAGCTG
ATGGTTCAGCAAGAGCTGCAAAACCAGAACAAAAGACACCTTTTGCAGTC
ATGACCTGGTTCCAACCACAATACAGAAAACTTTTGATGCCCCAGTTTC
AAGACAACAAATTCACGATGTAATAGACCAACAAATCCCTTCAGAATTT
TGTTTTGTGCCTTGAGACATAGACGGTAACTTCAGACATGCTCACACCAGA
ACTGTTCCAAGACAAACTCCACCTTATAGAGCCATGACAGATGTATTGGA
TGACCAACCTGTTTTAGATTCAATCAAAGAGAAGGTGTTTTAGTCGGTT
TTAGAACCCCACAACACATGCAAGGTATCAACGTAGCAGGTTATCATGAA
CACTTCATTACTGATGACAGACAAGGTGGTCATTGTTAGATTACCA
ATTGGAATCCGGTGTTTTGACATTCGGTGAAATCCACAAGTTGATGATTG
ATTTGCCAGCCGACAGTGCTTTCTTACAAGCCAACTTACACCCATCAAC
TTAGACGCCGCAATCAGATCAGTAGAAAACTAA SEQ ID No 10 (=Amino acid ALD.Ea)
MMMHSSACDCEASLCETLRGFSAKHPDSVIYQTSLMSALLSGVYEGDTTI
ADLLAHGDFGLGTFNELDGEMIAFSSQVYQLRADGSARAAKPEQKTPFAV
MTWFQPQYRKTFDAPVSRQQIHDVIDQQIPSDNLFCALRIDGNFRHAHTR
TVPRQTPPYRAMTDVLDDQPVFRFNQREGVLVGFRTPQHMQGINVAGYHE
HFITDDRQGGGHLLDYQLESGVLTFGEIHKLMIDLPADSAFLQANLHPSN
LDAAIRSVEN SEQ ID No 11 (=ADN ALD.L1)
ATGTCATCGAGAATCTTTCAACACAATACCTTCACAACTTTGAGTAGCGG
ATTTTACAAAGGCACAATCACGTTGAAAGAAGCCTTAGAACACGGATCAG
TTGGCATAGGTACATTAGATACTGCAAATGGTGAAGTTACCATCATCAAC
GGTATACCTATCATGGAGATTCGGAAAACATGTGAGATTGGTGGAAGA
GGATGAAACGATGCCTTATGTCGCTATGGTTGAACATCAACCCATTGCAA
AGTTCACTGATTCCTCTGTGTCAAATAGCGAAGATTTCCTATCCGCTTTA
ACCAAAAGGTTTCCAACCGTTAATACTGCCTACACAATTGTCATGACTGG
TCAGTTTAAGGAAGTAACTGTCTCTTCTAAACCAGCGAACAATACTAGA
CATATGACGAATAATGGCTGATCAACCGTACTTTACAAAGGAGAACATT
AGTGGTACAATGGTTGGTGTATGGGCTCCTAAACATCTTACTGATCTATT
TGGGTTAGGCTTTCACCTTCACTTCGTTTCTGACGATAAGACGTTTACTG
CACATGTACAGAATTTCATTACAGAGAATCTGGAAATTGAGATAGGGAAA
ATTACCAAGATTGACCAAGAATTTCCTGATGATGACGAGAACTTCGACCA
ACATTTGTTCCAATAA SEQ ID No 12 (=Amino acid ALD.L1)
MSSRIFQHNTFTTLSSGFYKGTITLKEALEHGSVGIGTLDTANGEVTIIN
GIAYHGDSENHVRLVEEDETMPYVAMVEHQPIAKFTDSSVSNSEDFLSAL
TKRFPTVNTAYTIVMTGQPKEVTVSSKPANNTRPYDEIMADQPYFTKENI
SGTMVGVWAPKHLTDLFGLGFHLHFVSDDKTFTAHVQNFITENLEIEIGK
ITKIDQEFPDDDENFDQHLFQ SEQ ID No 13 (=ADN NOXE.L1)
ATGGGTATTGTCGTAATAGGTACTAACCATGCCGGAATAGCTACAGCAAA
TACCTTAATCGACCAATATCCAGGACATGAAGTCATGATTGATAGGAA
ACTCGAATATGAGTTATCTTGGCTGTGGTACAGCGATTTGGGTTGGGAGA
CAAATCGAGAACCTGATGAACTTTTCTATGCAAAAGCAGAAGATTTCGA
AAAGAAGGGTGTTAAAATCCTGACCGAGACTGAAGTGTCAGAAATCGACT
TTACCAACAAAATGATATATGCCAAAAGCAAGACTGGGGAGAAAATCACG
GAATCTTATGATAAGCTAGTATTGGCAACAGGAAGCAGACCAATCATACC
CAATTTGCCTGGTAAAGATCTTAAAGGAATTCATTTCTTAAAGTTATTCC
AGGAAGGTCAAGCCATTGACGAAGAATTCGCAAAGAATGACGTGAAAAGA
ATCGCGGTAATTGGTGCTGGTTATATTGGAACAGAGATAGCTGAAGCAGC
TAAACGTAGAGGGAAAGAAGTGTTGTTTGATGCTGAAAGTACCTCAT
TAGCGTCATACTACGACGAAGAATTTGCCAAAGGCATGGATGAAAATTTG
GCACAACACGGATTGAGTTGCACTTTGGTGAACTTGCCCAAGAGTTCAA
GGCAAATGAAGAAGGTCATGTCTCCCAGATTGTTACAAACAAATCCACTT
ATGATGTGGATCTGGTCATCAATTGCATAGGATTTACTGCCAATTCAGCC
TTAGCTGGTGAGCACTAGAAAACGTTTAAGAACGGTGCCATAAAGGTTAA
TAAGCATCAACAATCAGTGATCCAGACGTGTATGCAGTTGGTGATGTTG
CAACTATCTACTCTAACGCTTTGCAAGACTTTACTTACATCGCTTTAGCT
AGCAATGCTGTTAGATCAGGCATTGTTGCTGGACACAATATTGGGATTCA
ATCCATAGAATCTGTCGGTCGTTCAGGGTAGTAACGGCATTTCTATATTCG
GATACAATATGACAAGTACTGGTTTATCAGTAAAAGCTGCTAAGAAGATT
GGTCTAGAAGTCTCCTTTTCTGATTTTGAAGATAAGCAAAAGGCTTGGTT
TCTGCATGAGAACAATGATTCGGTCAAATAAGGATCGTATACGAAACAA
AATCCAGGAGAATAATTGGCGCACATTGGCATCGAAATCAGAGATTATA
GCGGGCAACATTAACATGTTCTCTTTAGCCATTCAGGAAAAGAAAACGAT
TGATGAGTTAGCCCTATTGGATTTGTTCTTTCTGCCTCACTTTAACTCTC
CGTACAATTATATGACCGTAGCTGCGTTGAATGCTAAATAA SEQ ID No 14 (=Amino acid NOXE.L1)
MGIVVIGTNHAGIATANTLIDQYPGHEIVMIDRNSNMSYLGCGTAIWVGR
QIEKPDELFYAKAEDFEKKGVKILTETEVSEIDFTNKMIYAKSKTGEKIT
ESYDKLVLATGSRPIIPNLPGKDLKGIHFLKLFQEGQAIDEEFAKNDVKR
IAVIGAGYIGTEIAEAAKRRGKEVLLFDAESTSLASYYDEEFAKGMDENL
AQHGIELHFGELAQEFKANEEGHVSQIVTNKSTYDVDLVINCIGFTANSA
LAGEHLETFKNGAIKVNKHQQSSDPDVYAVGDVATIYSNALQDFTYIALA
SNAVRSGIVAGHNIGGKSIESVGVQSNGISIFGYNMTSTGLSVKAAKKI
GLEVSFSDFEDKQKAWFLHENNDSVKIRIVYETKSRRIIGAQLASKSEII
AGNINMFSLAIQEKKTIDELALLDLFFLPHFNSPYNYMTVAALNAK SEQ ID No 15 (=ADN NOXE.spn)
ATGTCTAAGATAGTGTAGTTGGTGCTAACCATGCAGGAACTGCTTGCAT
CAATACGATGTTGGATAATTTCGGCAATGAAATGAGATAGTGGTGTTTG
ATCAGAATTCCAACATCAGCTTTCTAGGTTGTGGATGGCGTTATGGATT
GGGGAGCAAATAGATGGTGCTGAAGGGTGTTTTACTGAGACAAAGAGAA
ATTGGAAGCCAAAGGTGCCAAAGTCTACATGAATTCGCCAGTCCTGAGTA
TAGACTATGACAACAAAGTGGTAACTGCAGAAGTAGAAGGCAAAGAGCAC
AAAGAATCCTATGAGAAACTGATCTTTGCTACTGGTTCAACACCGATTTT

SEQUENCE LISTING

```
ACCACCTATTGAAGGAGTCGAGATCGTTAAAGGTAATAGAGAATTTAAGG
CCACACTTGAAAACGTACAATTTGTTAAGTTGTATCAGAATGCTGAAGAA
GTCATCAACAAGCTTTCAGATAAAAGCCAGCATTTAGCAGATTGCTGT
TGTTGGAGGTGGATACATTGGTGTTGAATTGGCTGAAGCCTTTGAAAGAC
TAGGAAAAGAAGTTGTGTTAGTTGACATTGTGGACACTGTCTTAAACGGG
TATTATGACAAAGATTTCACCCAAATGATGGCCAAGAATCTTGAGGATCA
CAACATTAGACTTGCTTTAGGCCAAACAGTGAAGGCTATTGAAGGCGATG
GTAAGGTAGAAAGGTTGATTACAGACAAGGAGTCTTTCGATGTTGACATG
GTCATTTTAGCAGTAGGATTTAGACCAAACACTGCTTTGGCAGATGGGAA
AATTGAATTGTTTAGAAATGGTGCTTTTCTGGTGGATAAGAAACAAGAAA
CTTCAATACCCGATGTTTATGCAGTTGGTGATTGTGCAACAGTCTATGAT
AATGCCAGAAAGGATACTTCCTACATAGCATTGGCATCTAATGCAGTTAG
AACGGGCATTGTTGGTGCTTATAATGCCTGTGGTCATGAATTGGAGGGCA
TTGGTGTCCAAGGTTCTAATGGTATATCGATTTATGGCCTTCATATGGTT
AGTACCGGATTGACTCTGGAGAAGGCCAAAGCTGCTGGATACAATGCGAC
AGAAACAGGTTTCAACGATTTACAGAAGCCAGAGTTTTATGAAACACGACA
ACCATGAAGTAGCGATCAAAATCGTATTTGACAAGGATTCTCGTGAAATT
CTAGGGGCACAAATGGTTTCACACGATATAGCGATAAGTATGGGCATCCA
TATGTTCTCTCAGCGATTCAAGAACATGTTACCATAGATAAATTAGCAT
TAACCGATCTATTCTTCTTGCCTCATTTCAACAAACCTTACAATTACATC
ACGATGGCAGCTTTGACCGCCGAAAAGTAA

SEQ ID No 16 (=Amino acid NOXE.spn)
MSKIVVVGANHAGTACINTMLDNFGNENEIVVFDQNSNISFLGCGMALWI
GEQIDGAEGLFYSDKEKLEAKGAKVYMNSPVLSIDYDNKVVTAEVEGKEH
KESYEKLIFATGSTPILPPIEGVEIVKGNREFKATLENVQFVKLYQNAEE
VINKLSDKSQHLDRIAVVGGGYIGVELAEAFERLGKEVVLVDIVDTVLNG
YYDKDFTQMMAKNLEDHNIRLALGQTVKAIEGDGKVERLITDKESFDVDM
VILAVGFRPNTALADGKIELFRNGAFLVDKKQETSIPDVYAVGDCATVYD
NARKDTSYIALASNAVRTGIVGAYNACGHELEGIGVQGSNGISIYGLHMV
STGLTLEKAKAAGYNATETGFNDLQKPEFMKHDNHEVAIKIVFDKDSREI
LGAQMVSHDIAISMGIHMFSLAIQEHVTIDKLALTDLFFLPHFNKPYNYI
TMAALTAEK SEQ ID No 17 (=ADN NOXE.Ef)
ATGTCTGTGGTTGTCGTAGGCTGTACACATGCTGGTACTAGTGCAGTGAA
ATCTATCCTAGCTAATCATCCCGAAGCTGAAGTCACTGTTTATGAACGTA
ATGACAACATATCCTTCTTGTCTTGTGGAATTGCACTTTATGTTGGAGGT
GTAGTTAAGAATGCTGCCGACTTATTTTACAGCAATCCTGAGGAATTAGC
CAGTTTAGGAGCCACTGTGAAAATGGAACACAACGTAGAAGAGATCAATG
TCGATGATAAGACAGTTACGGCCAAAGAATCTACAAACAGGTGCAACAGA
ACCGTATCCTACGATAAGTTGGTCATGACTACTGGAAGTTGGCCTATAAT
TCCACCAATACCCGGAATTGATGCTGAGAACATTCTACTTTGCAAGAATT
ATTCTCAAGCGAATGTCATTATCGAAAAGGCCAAAGATGCGAAAAGAGTC
GTTGTCGTTGGTGGTGGCTATATTGGTATAGAGTTAGTTGAAGCTTTTGA
TGAAAGCGGTAAACAGGTGACCCTAGTTGATGGTCTAGACAGGATTTTGA
ACAAGTATTTGGACAAACCGTTTACTGATGTTTTAGAAAAGGAGTTAGTT
GATAGAGGTGTGAACTTAGCCTTAGGTGAAAATGTCCAACAGTTTGTAGC
TGATGAACAGGGAAAAGTTGCAAAAGTTATCACTCCATCTCAAGAATTCG
AAGCAGACATGGTCATAATGTGTGTTGGCTTTAGACCAAATACCGAACTT
TTGAAAGACAAAGTTGATATGTTGCCTAACGGTGCAATTGAGGTTAACGA
GTATATGCAAACGTCCAATCCAGATATCTTTGCTGCTGGTGATTCAGCCG
TAGTGCATTACAACCCATCGCAAACAGAGAATTATATTCCCTTAGCGACT
AATGCAGTAAGACAGGGTATGTTGGTGGGAGAAACTTGACAGAACAGAA
ACTTGCCTATAGAGGCACCCAAGGTACGTCTGGCTTGTACTTGTTCGGTT
GGAAAATTGGCTCAACAGGAGTAACCAAAGAATCGGCAAAATTGAATGGG
TTAGATGTTGAAGCTACAGTCTTTGAGGATAACTATAGACCTGAATTTCAT
GCCAACAACCGAAAAGGTGCTGATGGAGCTGGTGTACGAAAAGGGGACTC
AAAGGATAGTAGGTGGGCAATTGATGTCCAAATACGATATCACTCAATCA
GCGAATACACTTTCATTGGCTGTACAGAACAAATGACCGTTGAAGATCT
GGCTATTTCAGACTTCTTCTTTCAACCGCACTTTGACCGTCCTTGGAATT
ACTTAAATTTGCTAGCCCAAGCAGCTCTGGAGAACATGTAA SEQ ID No 18 (=Amino acid NOXE.Ef)
MSVVVVGCTHAGTSAVKSILANHPEAEVTVYERNDNISFLSCGIALYVGG
VVKNAADLFYSNPEELASLGATVKMEHNVEEINVDKTVTAKNLQTGATE
TVSYDKLVMTTGSWPIIPPIPGIDAENILLCKNYSQANVIIEKAKDAKRV
VVVGGGYIGIELVEAFVESGKQVTLVDGLDRILNKYLDKPFTDVLEKELV
DRGVNLALGENVQQFVADEQGKVAKVITPSQEFEADMVIMCVGFRPNTEL
LKDKVDMLPNGAIEVNEYMQTSNPDIFAAGDSAVVHYNPSQTKNYIPLAT
NAVRQGMLVGRNLTEQKLAYRGTQGTSGLYLFGWKIGSTGVTKESAKLNG
LDVEATVFEDNYRPEFMPTTEKVLMELVYEKGTQRIVGGQLMSKYDITQS
ANTLSLAVQNKMTVEDLAISDFFFQPHFDRPWNYLNLLAQAALENM SEQ ID No 19 (=ADN NOXE.Lb)
ATGTCTAAGGTTACCGTGGTAGGTTGTACACATGCCGGTACTTTTGCAAT
CAAACAGATTTTGGCAGAACATCCTGATGCAGAAGTAACAGTCTATGAGA GAAATGACGTGATTAGCTTCTTGTCGTGTGGCATAGCGTTGTACTTGGGT
GGGAAAGTTGCTGACCCTCAAGGGCTTTTCTACTCATCACCAGAAGAGTT
ACAAAAGCTTGGGGCGAATGTCCAAATGAACCACAACGTTTTAGCGATAG
ATCCAGATCAAAAGACTGTTACTGTTGAAGATCTAACGAGTCATGCTCAG
ACAACAGAATCCTATGACAAGTTAGTCATGACTTCAGGTTCTTGGCCGAT
AGTTCCCAAAATACCAGGTATTGACTCCGATAGAGTCAAGCTGTGCAAGA
ATTGGCGCTCATGCACAAGCTTTGATTGAAGATGCTAAAGAAGCGAAAAGA
ATTACTGTCATTGGCGCTGGTTATATCGGTGCCGAATTGGCCGAAGCGTA
TTCTACTACAGGTCACGACGTAACGTTGATAGACGCAATGGATAGAGTAA
TGCCCAAATACTTTGATGCAGATTTTACCGATGTCATTGAGCAAGATTAT
CGTGATCATGGAGTGCAATTAGCCTTGAGTGAAACTGTTGAATCGTTTAC
AGACAGTGCTACAGGATTGACCATAAAGACTGACAAGAATAGTTACGAAA
CAGATCTTGCCATCTTATGCATTGGCTTTAGACCAAATACGGATCTGCTG
AAAGGAAAAGTTGATATGGCACCAAATGGTGCTATTATTACCGATGACTA
TATGCGTTCCTCTAATCCGGACATATTTGCTGCAGGAGACTCTGCTGCA
TTCACTATAACCCTACACACCAGAATGCATATATCCCACTAGCCACAAAT
GCTGTGAGACAAGGTATATTAGTAGGCAAGAATTTGGTCAAACCGACCGT
TAAATACATGGGTACGCAAAGCTCTTCAGGTCTTGCCCTGTACGATAGGA
CTATTGTTTCGACCGGCTTAACGCTAGCAGCAGCTAAACAACAGGGTGTT
AATGCTGAACAGGTGATCGTTGAGGACAATTATAGACCTGAGTTTATGCC
TTCAACTGAACCCGTGCTAATGAGCTTAGTCTTTGATCCAGATACTCATA
GGATCTTAGGAGGAGCTTTGATGTCAAATACGATGTATCCCAGTCTGCA
AACACCTTGTCTGTGTGTATCCAAAACGAGAATACTATTGATGACTTAGC
CATGGTTGATATGCTTTTCCAACCTAACTTCGATAGACCATTCAACTATC
TAAACATTTTGGCTCAAGCTGCTCAAGCCAAAGTAGCTCAATCAGTAAAC
GCCTAG SEQ ID No 20 (=Amino acid NOXE.Lb)
MSKVTVVGCTHAGTFAIKQILAEHPDAEVTVYERNDVISFLSCGIALYLG
GKVADPQGLFYSSPEELQKLGANVQMNHNVLAIDPDQKTVTVEDLTSHAQ
TTESYDKLVMTSGSWPIVPKIPGIDSDRVKLCKNWAHAQALIEDAKEAKR
ITVIGAGYIGAELAEAYSTTGHDVTLIDAMDRVMPKYFDADFTDVIEQDY
RDHGVQLALSETVESFTDSATGLTIKTDKNSYETDLAILCIGFRPNTDLL
KGKVDMAPNGAIITDDYMRSSNPDIFAAGDSAAVHYNPTHQNAYIPLATN
AVRQGILVGKNLVKPTVKYMGTQSSSGLALYDRTIVSTGLTLAAAKQQGV
NAEQVIVEDNYRPEFMPSTEPVLMSLVFDPDTHRILGGALMSKYDVSQSA
NTLSVCIQNENTIDDLAMVDMLFQPNFDRPFNYLNILAQAAQAKVAQSVN
A SEQ ID No 21 (=pENO2)
CGCTCAGCATCTGCTTCTTCCCAAAGATGAACGCGGCGTTATGTCACTAA
CGACGTGCACCAACTTGCGGAAAGTGGAATCCCGTTCCAAAACTGGCATC
CACTAATTGATACATCTACACACCGCACGCCTTTTTTCTGAAGCCCACTT
TCGTGGACTTTGCCATATGCAAATTCATGAAGTGTGATACCAAGTCAGC
ATACACCTCACTAGGGTAGTTTCTTTGGTTGTATTGATCATTTGGTTCAT
CGTGGTTCATTAATTTTTTTTTCTCCATTGCTTTCTGGCTTTGATCTTACT
ATCATTTGGATTTTTGTCGAAGGTTGTAGAATTGTATGTGACAAGTGGCA
CCAAGCATATATAAAAAAAAAAAGCATTATCTTCCTACCAGAGTTGATTG
TTAAAAACGATTTTATAGCAAACAGCAATTGTAATTAATTCTTATTTTGTA
TCTTTTCTTCCCTTGTCTCAATCTTTATTTTTATTTTATTTTTCTTTTC
TTAGTTTCTTTCATAACACCAAGCAACTAATACTATAACATACAATAATA SEQ ID No 22 (=pTEF2.K1)
CTCTCTCGCAATAACAATGAACACTGGGTCAATCATAGCCTACACAGGTG
AACAGAGTAGCGTTTATACAGGGTTTATACGGTGATTCCTACGGCAAAAA
TTTTTCATTTCTAAAAAAAAAAGAAAAATTTTTCTTTCCAACGCTAGAA
GGAAAAGAAAATCTAATTAAATTGATTTGGTGATTTTCTGAGAGTTCCC
TTTTTCATATATCGAATTTGAATATAAAAGGAGATCGAAAAAATTTTTC
TATTCAATCTGTTTTCTGGTTTTATTTGATAGTTTTTTTGTGTATTATTA
TTATGGATTAGTACTGGTTTATATGGGTTTTCTGTATAACTTCTTTTTA
TTTTAGTTTGTTTAATCTTATTTTGAGTTACATTATAGTTCCCTAACTGC
AAGAGAAGTAACATTAAAA SEQ ID No 23 (=pTEF3)
GGCTGATAATAGCGTATAAACAATGCATACTTTGTACGTTCAAAATACAA
TGCAGTAGATATATTATGCATATTACATAATACATATCACATAGGAA
GCAAACAGGCGCGTTGGACTTTTAATTTTCGAGGACCGCGAATCCTTACAT
CACACCCAATCCCCCACAAGTGATCCCCACACACCATAGCTTCAAAATG
TTTCTACTCCTTTTTTACTCTTCCAGATTTTCTCGGACTCCGCGCATCGC
CGTACCACTTCAAAACACCCAAGCACAGCATACTAAATTTCCCCTCTTTC
TTCCTCTAGGGTGTCGTTAATTACCCGTACTAAAGGTTTGGAAAAGAAAA
AAGAGACCGCCTCGTTTCTTTTTCTTCGTCGAAAAAGGCAATAAAAATTT
TTATCACGTTTCTTTTTCTTGAAAATTTTTTTTTTGATTTTTTTCTCTT
TCGATGACCTCCCATTGATATTTAAGTTAATAAACGGTCTTCAATTTCTC
AAGTTTCAGTTTCATTTTTCTTGTTCTATTACAACTTTTTTTACTTCTTG
CTCATTAGAAAGAAAAGCATAGCAATCTAATCTAAGTTTTAATTACAAA
```

SEQUENCE LISTING

SEQ ID No 24 (=pADH1)
GGGTGTACAATATGGACTTCCTCTTTTCTGGCAACCAAACCCATACATCG
GGATTCCTATAATACCTTCGTTGGTCTCCCTAACATGTAGGTGGCGGAGG
GGAGATATACAATAGAACAGATACCAGACAAGACATAATGGGCTAAACAA
GACTACACCAATTACACTGCCTCATTGATGGTGGTACATAACGAACTAAT
ACTGTAGCCCTAGACTTGATAGCCATCATCATATCGAAGTTTCACTACCC
TTTTTCCATTTGCCATCTATTGAAGTAATAATAGGCGCATGCAACTTCTT
TTCTTTTTTTTCTTTTCTCTCTCCCCCGTTGTTGTCTCACCATATCCGC
AATGACAAAAAATGATGGAAGACACTAAAGGAAAAATTAACGACAAAG
ACAGCACCAACAGATGTCGTTGTTCCAGAGCTGATGAGGGGTATCTCGAA
GCACACGAAACTTTTTCCTTCCTTCATTCACGCACACTACTCTCTAATGA
GCAACGGTATACGGCCTTCCTTCCAGTTACTTGAATTTGAAATAAAAAAA
AGTTTGCTGTCTTGCTATCAAGTATAAATAGACCTGCAATTATTAATCTT
TTGTTTCCTCGTCATTGTTCTCGTTCCCTTTCTTCCTTGTTTCTTTTTCT
GCACAATATTTCAAGCTATACCAAGCATACAATCAACTATCTCATATACA

SEQ ID No 25 (=pGPM1)
GCCAAACTTTTCGGTTAACACATGCAGTGATGCACGCGCGATGGTGCTAA
GTTACATATATATATATATATATATATATATATATATAGCCATAGTGA
TGTCTAAGTAACCTTTATGGTATATTTCTTAATGTGGAAAGATACTAGCG
CGCGCACCCACACACAAGCTTCGTCTTTTCTTGAAGAAAAGAGGAAGCTC
GCTAAATGGGATTCCACTTTCCGTTCCCTGCCAGCTGATGGAAAAAGGTT
AGTGGAACGATGAAGAATAAAAAGAGAGATCCACTGAGGTGAAATTTCAG
CTGACAGCGAGTTTCATGATCGTGATGAACAATGGTAACGAGTTGTGGT
GTTGCCAGGGAGGGTGGTTCTCAACTTTTAATGTATGGCCAAATCGCTAC
TTGGGTTTGTTATATAACAAAGAAGAAATAATGAACTGATTCTCTTCCTC
CTTCTTGTCCTTTCTTAATTCTGTTGTAATTACCTTCCTTTGTAATTTTT
TTTGTAATTATTCTTCTTAATAATCCAAACAAACACACATATTACAATA

SEQ ID No 26 (=pFBA1)
ACGCAAGCCCTAAGAAATGAATAACAATACTGACAGTACTAAATAATTGC
CTACTTGGCTTCACATACGTTGCATACGTCGATATAGATAATAATGATAA
TGACAGCAGGATTATCGTAATACGTAATAGTTGAAAATCTCAAAAATGTG
TGGGTCATTACGTAAATAATGATAGGAATGGGATTCTTCTATTTTTCCTT
TTTCCATTCTAGCAGCCGTCGGGAAAACGTGGCATCCTCTCTTTCGGGCT
CAATTGGAGTCACGCTGCCGTGAGCATCCTCTCTTTCCATATCTAACAAC
TGAGCACGTAACCAATGGAAAAGCATGAGCTTAGCGTTGCTCCAAAAAAG
TATTGGATGGTTAATACCATTTGTCTGTTCTCTTCTGACTTTGACTCCTC
AAAAAAAAAAAATCTACAATCAACAGATCGCTTCAATTACGCCCTCACAA
AAACTTTTTTCCTTCTTCTTCGCCCACGTTAAATTTATCCCTCATGTTG
TCTAACGGATTTCTGCACTTGATTTATTATAAAAAGACAAAGACATAATA
CTTCTCTATCAATTTCAGTTATTGTTCTTCCTTGCGTTATTCTTCTGTTC
TTCTTTTTCTTTTGTCATATATAACCATAACCAAGTAATACATATTCAAA

SEQ ID No 27 (=pPDC1)
TTATTTACCTATCTCTAAACTTCAACACCTTATATCATAACTAATATTTC
TTGAGATAAGCACACTGCACCCATACCTTCCTTAAAAACGTAGCTTCCAG
TTTTTGGTGGTTCCGGCTTCCTTCCCGATTCCGCCCGCTAAACGCATATT
TTTGTTGCCTGGTGGCATTTGCAAAATGCATAACCTATGCATTTAAAAGA
TTATGTATGCTCTTCTGACTTTTCGTGTGATGAGGCTCGTGGAAAAAATG
AATAATTTATGAATTTGAGAACAATTTTGTGTTGTTACGGTATTTTACTA
TGGAATAATCAATCAATTGAGGATTTTATGCAAATATCGTTTGAATATTT
TTCCGACCCTTTGAGTACTTTTCTTCATAATTGCATAATATTGTCCGCTG
CCCCTTTTTCTGTTAGACGGTGTCTTGTGATCTACTTGCTATCGTTCAACAC
CACCTTTATTTTCTAACTATTTTTTTTTTAGCTCATTTGAATCAGCTTATG
GTGATGGCACATTTTTGCATAAACCTAGCTGTCCTCGTTGAACATAGGAA
AAAAAAATATATAAACAAGGCTCTTTCACTCTCCTTGCAATCAGATTTGG
GTTTGTTCCCTTTATTTTCATATTTCTTGTCATATTCCTTTCTCAATTAT
TATTTTCTACTCATAACCTCACGCAAAATAACACAGTCAAATCAATCAAA

SEQ ID No 28 (=pPGK1)
GTGAGTAAGGAAAGAGTGAGGAACTATCGCATACCTGCATTTAAAGATGC
CGATTTGGGCGCGAATCCTTTATTTTGGCTTCACCCTCATACTATTATCA
GGGCCAGAAAAAGGAAGGTTTCCCTCCTTCTTGAAATTCTTATTCTTGAGTAACTC
ATAAAGCACGTGGCCTCTTATCGAGAAAGAAATTACCGTCGCTCGTGATT
TGTTTGCAAAAAGAACAAAACTGAAAAAACCCAGACACGCTCGACTTCCT
GTCTTCCTATTGATTGCAGCTTCCAATTTCGTCACACAACAAGGTCCTAG
CGACGGCTCACAGGTTTTGTAACAAGCAATCGAAGGTTCTGGAATGGCGG
GAAAAGGGTTTAGTACCACATGCTATGATGCCCACTGTGATCTCCAGAGCA
AAGTTCGTTCGATCGTACTGTTACTCTCTCTTTCAAACAGAATTGTCC
GAATCGTGTGACAACAACAGCCTGTTCTCACACACTCTTTTCTTCTAACC
AAGGGGGTGGTTAGTTTAGTAGAACCTCGTGAAACTTACATTTACATAT
ATATAAACTTGCATAAATTGGTCAATGCAAGAAATACATATTTGGTCTTT
TCTAATTCGTAGTTTTTCAAGTTCTTAGATGCTTTCTTTTTCTCTTTTTT
ACAGATCATCAAGGAAGTAATTATCTACTTTTTACAACAAATATAAACA

SEQ ID No 29 (=pRPLA1)
TCAAGTTGGATACTGATCTGATCTCTCCGCCCTACTACCAGGGACCCTCA
TGATTACCGCTCGAATGCGACGTTTCCTGCCTCATAAAACTGGCTTGAAA
ATATTTATTCGCTGAACAGTAGCCTAGCTTATAAAAATTTCATTTAATTA
ATGTAATATGAAAACTCACATGCCTTCTGTTTCTAAAATTGTCACAGCAA
GAAATAACATTACCATACGTGATCTTATTAAACTCTAGTATCTTGTCTAA
TACTTCATTTAAAAGAAGCCTTAACCCTGTAGCCTCATCTATGTCTGCTA
CATATCGTGAGGTACGAATATCGTAAGATGATACCACGCAACTTTGTAAT
GATTTTTTTTTTTTCATTTTTTAAAGAATGCCTTTACATGGTATTTGAAA
AAAATATCTTTATAAAGTTTGCGATCTCTTCTGTTCTGAATAATTTTTAG
TAAAAGAAATCAAAAGAATAAAGAAATAGTCCGCTTTGTCCAATACAACA
GCTTAAACCGATTATCTCTAAAATAACAAGAAGAA

SEQ ID No 30 (= pTEF1)
GTTTAGCTTGCCTCGTCCCCGCCGGGTCACcCGgccaGCGACATGGAGGC
CCAGAATACCCTCCTTGACAGTCTTGACGTGCGCAGCTCAGGGGCATGAT
GTGACTGTCGCCCGTACATTTAGCCCATACATCCCCATGTATAATCATTT
GCATCCATACATTTTGATGGCCGCACGGCGCGAAGCAAAAATTACGGCTC
CTCGCTGCAGACCTGCGAGCAGGGAAACGCTCCCCTCACAGACGCGTTGA
ATTGTCCCCACGCCGCGCCCCTGTAGAGAAATATAAAAGGTTAGGATTTG
CCACTGAGGTTCTTCTTTCATATACTTCCTTTTAAAATCTTGCTACGATA
CAGTTCTCACATCACATCCGAACATAAACAACC SEQ ID No 31 (=pTDH3)
CTGCTGTAACCCGTACATGCCCAAAATAGGGGGCGGGTTACACAGAATAT
ATAACATCGTAGGTGTCTGGGTGAACAGTTTATTCCTGGCATCCACTAAA
TATAATGGACCCCGCTTTTTAAGCTGGCATCCAGAAAAAAAAAGGAATCCC
AGCACCAAAATATTGTTTTCTTCACCAACCATCAGTTCATAGGTCCATTC
TCTTAGCGCAACTACAGAGAACAGGGGCACAAACAGGCAAAAAACGGGCA
CAACCTCAATGGAGTGATGCAACCTGCCTGGAGTAAATGATGACACAAGG
CAATTGACCCACGCATGTATCTATCTCATTTTCTTACACCTTCTATTACC
TTCTGCTCTCTCTGATTTGGAAAAAGCTGAAAAAAAAGGTTGAAACCAGT
TCCCTGAAATTATTCCCCTACTTGACTAATAAGTATATAAAGACGGTAGG
TATTGATTGTAATTCTGTAAATCTATTTCTTAAACTTCTTAAATTCTACT
TTTATAGTTAGTCTTTTTTTTAGTTTTAAAACACCAAGAACTTAGTTTCG
AATAAACACACATAAACAAACAAA SEQ ID No 32 (=tTHD2)
ATTTAACTCCTTAAGTTACTTTAATGATTTAGTTTTTTATTATTAATAATT
CATGCTCATGACATCTCATATACACGTTTATAAAACTTAAATAGATTGAA
AATGTATTAAAGATTCCTCAGGGATTCGATTTTTTTGGAAGTTTTTGTTT
TTTTTTCCTTGAGATGCTGTAGTATTTGGGAACAATTATACAATCGAAAG
ATATATGCTTACATTCGACCGTTTTAGCCGTGATCATTATCCTATAGTAA
CATAACCTGAAGCATAACTGACACTACTATCATCAATACTTGTCACATGA SEQ ID No 33 (=tCYC1)
ACAGGCCCCTTTTCCTTTGTCGATATCATGTAATTAGTTATGTCACGCTT
ACATTCACGCCCTCCTCCCACATCCGCTCTAACCGAAAAGGAAGGAGTTA
GACAACCTGAAGTCTAGGTCCCTATTTATTTTTTTTAATAGTTATGTTAG
TATTAAGAACGTTATTTATATTTCAAATTTTTCTTTTTTTTCTGTACAAA
CGCGTGTACGCATGTAACATTATACTGAAAACCTTGCTTGAGAAGGTTTT
GGGACGCTCGAAGGCTTTAATTTGCAAGCTTCGCAGTTTACACTCTCATC SEQ ID No 34 (=tTDH3)
GTGAATTTACTTTAAATCTTGCATTTAAATAAATTTTCTTTTTATAGCTT
TATGACTTAGTTTCAATTTATATACTATTTTAATGACATTTTCGATTCAT
TGATTGAAAGCTTTGTGTTTTTTCTTGATGCGCTATTGCATTGTTCTTGT
CTTTTTCGCCACATGTAATATCTGTAGTAGATACCTGATACATTGTGGAT
GCTGAGTGAAATTTTAGTTAATAATGGAGGCGCTCTTAATAATTTTGGGG
ATATTGGCTTTTTTTTTAAAGTTTACAAATGAATTTTTTCCGCCAGGAT SEQ ID No 35 (=tADH1)
ACTAGTTCTAGAGCGGCCGCCACCGCGGTGGGCGAATTTCTTATGATTTA
TGATTTTTATTATTAAATAAGTTATAAAAAAAATAAGTGTATACAAATTT
TAAAGTGACTCTTAGGTTTAAACGAAAATTCTTATTCTTGAGTAACTC
TTTCCTGTAGGTCAGGTTGCTTTCTCAGGTATAGCATGAGGTCGCTCTTA
TTGACCACACCTCTACCGGCATGCCGAGCAAATGCCTGCAAATCGCTCCC
CATTTCACCCAATTGTAGATATGCTAACTCCAGCAATGAGTTGAtGAATC
TCGGTGTGTATTTTATGTCCTCAGAgGACAACACCTGTTGTAATCGTTCT
TCCA SEQ ID No 36 (=tTPI1)
GATTAATATAATTATATAAAAATATTATCTTCTTTTCTTTATATCTAGTG
TTATGTAAAATAAATTGATGACTACGGAAAGCTTTTTATATTGTTTCTT
TTTCATTCTGAGCCACTTAAATTTCGTGAATGTTCTTGTAAGGGACGGTA
GATTTACAAGTGATACAACAAAAAGCAAGGCGCTTTTTCTAATAAAAGA

SEQUENCE LISTING

AGAAAAGCATTTAACAATTGAACACCTCTATATCAACGAAGAATATTACT
TTGTCTCTAAATCCTTGTAAAATGTGTACGATCTCTATATGGGTTACTC

SEQ ID No 37 (=tMET25)
GTGTGCGTAATGAGTTGTAAAATTATGTATAAACCTACTTTCTCTCACAA
GTACTATACTTTTATAAAACGAACTTTATTGAAATGAATATCCTTTTTTT
CCCTTGTTACATGTCGTGACTCGTACTTTGAACCTAAATTGTTCTAACAT
CAAAGAACAGTGTTAATTCGCAGTCGAGAAGAAAAATATGGTGAACAAGA
CTCATCTACTTCATGAGACTACTTTACGCCTCCTATAAAGCTGTCACACT
GGATAAATTTATTGTAGGACCAAGTTACAAAAGAGGATGATGGAGGTTT

SEQ ID No 38 (=tENO2)
GGATCCTAAAGTGCTTTTAACTAAGAATTATTAGTCTTTTCTGCTTATTT
TTTCATCATAGTTTAGAACACTTTATATTAACGAATAGTTTATGAATCTA
TTTAGGTTTAAAAATTGATACAGTTTTATAAGTTACTTTTTCAAAGACTC
GTGCTGTCTATTGCATAATGCACTGGAAGGGGAAAAAAAAGGTGCACACG
CGTGGCTTTTTCTTGAAATTTGCAGTTTGAAAAATAACTACATGGATGATA
AGAAACATGGAGTACAGTCACTTTGAGAACCTTCAATCAGCTGGTAACG
TCTTC

SEQ ID No 39 (=tMET3)
TCGTCATAAAATGCTCCCATCTCAAAAGTAGGGCAAAATTCATGATCGAC
CGCGCAAAATAAATAGATTTGCAAATAAGTTTTGTATGTACATTTATTAA
TATATATAATATATCAAAAGAAAAAAATCAAAAAAAAAAGAAAAACAAA
TTGCACTCTTATTCAGTCATCAATTACAAAACCTAGAGATAGCGATGGTG
CATATTCAATAAAAAACTCCTTATACTGTCGAGAAAGCTTATTATTGGTA
CTTCTCGAAGATACTAAAAAAGGTTAATTTTTGGAGACGGAGGCAATAGC

SEQ ID No 40 (=tPGK1)
ATTGAATTGAATTGAAATCGATAGATCAATTTTTTTCTTTTCTCTTTCCC
CATCCTTTACGCTAAAATAATAGTTTATTTTATTTTTTGAATATTTTTA
TTTATATACGTATATATAGACTATTATTTATCTTTTAATGATTATTAAGA
TTTTTATTAAAAAAAAATTCGCTCCTCTTTTTAATGCCTTTATGCAGTTT
TTTTTCCCATTCGATATTTCTATGTTCGGGTTCAGCGTATTTTAAGTTTA
ATAACTCGAAAATTCTGCGTTCGTTAAAGCTTTCGAGAAGGATATTATTT
A

SEQ ID No 41 (=pPYK1)
AAAAGGAAAGATTATTGAAAGAGAAAGAAAGAAAAAAAAAAAATGTACAC
CCAGACATCGGGCTTCCACAATTTCGGCTCTATTGTTTTCCATCTCTCGC
AACGGCGGGATTCCTCTATGGCGTGTGATGTCTGTATCTGTTACTTAATC
CAGAAACTGGCACTTGACCCAACTCTGCCACGTGGGTCGTTTTGCCATCG
ACAGATTGGGAGATTTTCATAGTAGAATTCAGCATGATAGCTACGTAAAT
GTGTTCCGCACCGTCACAAAGTGTTTTCTACTGTTCTTTCTTCTTTCGTT
CATTCAGTTGAGTTGAGTGAGTGCTTTGTTCAATGGATCTTAGCTAAAAT
GCATATTTTTTCTCTTGGTAAATGAATGCTTGTGATGCTTCCAAGTGAT
TTCCTTTCCTTCCCATATGATGCTAGGTACCTTTAGTGTCTTCCTAAAAA
AAAAAAAGGCTCGCCATCAAAACGATATTCGTTGGCGTTTTTTTCTGAA
TTATAAATACTCTTTGGTAACTTTTCATTTCCAAGAACTCTTTTTTTCCA
GTTATATCATGGTCTCCCTTTCAAAGTTATTCTCTACTCTTTTTCATATTC
ATTCTTTTTCATCCTTTGGTTTTTTATTCTTAACTTGTTTATTATTCTCT
CTTGTTTCTATTTACAAGACACCAATCAAAACAAATAAAACATCATCACA

SEQ ID No 42 (=pTPI1)
ATTTAAAACTGTGAGGACCTTAATACATTCAGACACTTCTGCGGTATCACC
CTACTTATTCCCTTCGAGATTATATCTAGGAACCCATCAGGTTGGTGGAA
GATTACCCGTTCTAAGACTTTTCAGCTTCCTCTATTGATGTTACACCTGG
ACACCCCTTTTCTGGCATCCAGTTTTAATCTTCAGTGGCATGTGAGATT
CTCCGAATTAATTAAAGCAATCACACAATTCTCTCGGATACCACCTCGG
TTGAAACTGACAGGTGGTTTGTTACGCATGCTAATGCAAAGGAGCCTATA
TACCTTTGGCTCGGCTGCTGTAACAGGGAATATAAAGGGCAGCATAATTT
AGGAGTTTAGTGAACTTGCAACATTTACTATTTTCCCTTCTTACGTAAAT
ATTTTTCTTTTTAATTCTAAATCAATCTTTTTCAATTTTTTGTTTGTATT
CTTTTCTTGCTTAAATCTATAACTACAAAAAACACATACATAAACTAAAA

SEQ ID No 43 (=tDIT1)
<u>TAAAGTAAGAGCGCTACATTGGTCTACCTTTTTGTTCTTTTACTTAAACA</u>
<u>TTAGTTAGTTCGTTTTCTTTTTCTCATTTTTTATGTTTCCCCCCCAAAG</u>
<u>TTCTGATTTTATAAATTTTATTTCACAAATTCACTTAACAGAGGGGG</u>
<u>AATAGATTCTTTAGCTTAGAAAATTAGTGATCAATATATATTTGCCTTTC</u>
<u>TTTTCATCTTTTCAGTGATATTAATGGTTTCGAGACACTGCAATGGCCCT</u>
<u>AGTTGTCTAAGAGGATAGATGTTACTGTCAAAGATGATTTTGAATTTC</u>

SEQ ID No 44 (=loxP)
<u>ATAACTTCGTATAATGTATGCTATACGAAGTTA</u>

SEQ ID No 45 (=nucleic acid HAA-1)
ATGGTCTTGATAAATGGCATAAAGTATGCCTGTGAGAGGTGCATAAGAGG
CCATAGAGTAACAACATGCAATCATACAGATCAACCGCTTATGATGATCA
AACCCAAAGGTAGACCTTCCACTACATGCGACTATTGTAAACAACTTCGA
AAAAAACAAGAATGCAAATCCTGAAGGTGTTTGCACGTGTGGCCGGCTAGA
GAAGAAAAACTGGCACAGAAAGCCAAAGAAGAAGCAAGAGCTAAAGCCA
AAGAAAAACAAAGAAAACAGTGTACCTGCGGGACTGATGAGGTTTGCAAA
TATCATGCTCAAAAGAGACATCTAAGAAAGTCCCCTTCAAGTTCTCAAAA
GAAAGGAAGATCCATTTCTCGTTCTCAACCAATGTTTGAAAGGGTATTGT
CTTCTACTTCACTTGACAGCAATATGTTATCCGGCCACGGAGCACTATCA
GATACCTCTAGCATACTGACGAGCACATTTTTAGACAGTGAGCCGGGTGT
TGGTAAAATTTCAAAAGATTACCATCATGTCCCTTCATTGGCCTCCATTT
CATCCTTACAATCCTCGCAATCGTTAGATCAAAATTTCAGTATACCACAA
AGCCCGCCGTTATCTTCAATGTCATTTAATTTTCTCACGGGAAATATCAA
TGAAACCAACCAAAATCACAGTAATCATCAGCATTCAAAATCAGGCAATA
ACTGGCAAGATAGTTCGGTAAGCTTGCCAGCGAAAGCTGATTCACGTCTT
AACATGATGGATAAAAACAACTCTGTGGGTCTTGACCTATTAGGCCATTC
AAAACGAATATCGCCGATATCAAACTCTCGTGTGGGCGAAGTTAGCGTTC
CGCTAGAGAATATATTCCTTCTGACATTGATGGGGTTGGAAGAGTTACT
GATAAAAGCTCTTTGGTCTACGATTGGCCATTTGATGAAAGTATTGAGAG
AAATTTCAGTACAACCGCAACCGCTGCAACTGGTGAAAGTAAGTTCGACA
TTAACGACAACTGTAATAGAATTAATAGCAAAAGTTATAGTAAGACTAAT
AGTATGAATGGAACGGTATTGAACAATAGCAATAATAATAATGTCAACAG
TAATGCAACGACAAGAACAATAACAACTCTTCTAGACAAGAACATCAAG
GAAATGGACTATTTGACATGTTTACAGATTCATCGTCGATTTCAACGCTT
TCCCGTGCAAACTTATTATTGCAAGAAAAAATTGGTTCGCAAGAAAACTC
TGTCAAACAAGAAAACTATTCGAAAAATCCTCAACTTCGTCATCAATTAA
CTTCCAGAAGTAGATCATTTATTCATCATCCGGCAAACGAGTATTTGAAG
AATACTTTTGGAAATTCACATAGTAATGACATCGGAAAGGGAGTTGAAGT
GCTATCTTTGACACCGAGTTTTATGGATATTCCCGAAAAAGAAAGAGAAA
CGGAAAGATCGCCATCATCCAATTACATTACTGACAGACCTTTCACTCGA
AAACCTAGATCTTCTAGCATTGACGTAAACCATAGGTATCCACCTATGGC
ACCAACAACCGTAGCGACATCTCCCGGTGCATTGAACAATGCCGTAGCAA
GCAATCTCGACGATCAACTGAGTTTAACATCACTAAACTCTCAGCCATCA
TCGATAGCAAATATGATGATGGACCCTTCAAACCTAGCTGAGCAAAGTTC
TATTCATTCAGTTCCTCAGTCAATAAACTCTCCGAGAATGCCTAAAACTG
GAAGTCGCCAAGACAAGAACATTCACACTAAGGAAGGAAGAAAGAAATCCG
CTAAATAACATACACGATCTGTCACAATTGGAAAATGTACCAGACGAGAT
GAACCAAATGTTCTCCCCACCATTAAAAAGTATGAATAGACCGGATGCCA
TAAGGGAAAATTCATCTAGTAGTAATTTCATAATCCAAGGAAATAGCATG
ATCTCTACGCCTTCCGGAAGGAATGACCTTCCAGATACCTCTCCAATGAG
TAGTATTCAAACAGCGTCACCACCAAGTCAATTACTGACCGATCAAGGAT
TTGCGGATTTGGATAATTTCATGTCTTCGTTATGA SEQ ID No 46 (=amino acid HAA-1)
MVLINGIKYACERCIRGHRVTTCNHTDQPLMMIKPKGRPSTTCDYCKQLR
KNKNANPEGVCTCGRLEKKKLAQKAKEEARAKAKEKQRKQCTCGTDEVCK
YHAQKRHLRKSPSSSQKKGRSISRSQPMFERVLSSTSLDSNMLSGHGALS
DTSSILTSTFLDSEPGVGKISKDYHHVPSLASISSLQSSQSLDQNFSIPQ
SPPLSSMSFNFLTGNINETNQNHSNHQHSKSGNNWQDSSVSLPAKADSRL
NMMDKNNSVGLDLLGHSKRISPISNSRVGEVSVPLEEYIPSDIDVGRVT
DKSSLVYDWPFDESIERNFSTTATAATGESKFDINDNCNRINSKSYSKTN
SMNGNGMNNSNNNNINSNGNDKNNNNSSRQEHQGNGLFDMFTDSSSISTL
SRANLLLQEKIGSQENSVKQENYSKNPQLRHQLTSRSRSFIHHPANEYLK
NTFGNSHSNDIGKGVEVLSLTPSFMDIPEKERETERSPSSNYITDRPFTR
KPRSSSIDVNHRYPPMAPTTVATSPGALNNAVASNLDDQLSLTSLNSQPS
SIANMMMDPSNLAEQSSIHSVPQSINSPRMPKTGSRQDKNIHTKKEERNP
LNNIHDLSQLENVPDEMNQMFSPPLKSMNRPDAIRENSSSSNFIIQGNSM
ISTPSGRNDLPDTSPMSSIQTASPPSQLLTDQGFADLDNFMSSL SEQ ID No 47 (=nucleic acids LEU2.K1)
ATGTCTAAGAATATCGTTGTCCTACCGGGTGATCACGTCGGTAAAGAAGT
TACTGACGAAGCTATTAAGGTCTTGAATGCCATTGCTGAAGTCCGTCCAG
AAATTAAGTTCAATTTCCAACATCACTTGATCGGGGTGCTGCCATCGAT
GCCACTGGCACTCCTTTACCAGATGAAGCTCTAGAAGCCTCTAAGAAAGC
CGATGCTGTCTTACTAGGTGCTGTTGGTGGTCCAAAATGGGGTACGGGCG
CAGTTCTAGACAGAACAAGGTCTATTGAAGATCAGAAAGGAATTGGGTCTA
TACGCCAACTTGAGACCATGTAACTTTGCTTCTGATTCTTTACTAGATCT
TTCTCCTTTGAAGCCTGAATATGCAAAGGGTACCGATTTCGTCGTCGTTA
GAGAATTGGTTGGTGGTATCTACTTTGGTGAAAGAAAAGAAGATGAAGGT
GACGGAGTTGCTTGGGACTCTGAGAAATACAGTGTTCCTGAAGTTCAAAG
AATTACAAGAATGGCTGCTTTCTTGGCATTGCAACAAACCCACCATTAC
CAATCTGGTCTCTTGACAAGGCTAACGTGCTTGCCTCTTCCAGATTGTGG
AGAAAGACTGTTGAAGAAACCATCAAGACTGAGTTCCCACAATTAACTGT
TCAGCACCAATTGATCGACTCTGCTGCTATGATTTTGGTTAAATCACCAA
CTAAGCTAAACGGTGTTGTTATTACCAACAACATGTTTGGTGATATTATC

SEQUENCE LISTING

```
TCCGATGAAGCCTCTGTTATTCCAGGTTCTTTGGGTTTATTACCTTCTGC
ATCTCTAGCTTCCCTACCTGACACTAACAAGGCATTCGGTTTGTACGAAC
CATGTCATGGTTCTGCCCCAGATTTACCAGCAAACAAGGTTAACCCAATT
GCTACCATCTTATCTGCAGCTATGATGTTGAAGTTATCCTTGGATTTGGT
TGAAGAAGGTAGGGCTCTTGAAGAAGCTGTTAGAAATGTCTTGGATGCAG
GTGTCAGAACCGGTGACCTTGGTGGTTCTAACTCTACCACTGAGGTTGGC
GATGCTATCGCCAAGGCTGTCAAGGAAATCTTGGCTTAA
```

SEQ ID No 48 (=amino acid LEU2.K1)
```
MSKNIVVLPGDHVGKEVTDEAIKVLNAIAEVRPEIKFNFQHHLIGGAAID
ATGTPLPDEALEASKKADAVLLGAVGGPKWGTGAVRPEQGLLKIRKELGL
YANLRPCNFASDSLLDLSPLKPEYAKGTDFVVVRELVGGIYFGERKEDEG
DGVAWDSEKYSVPEVQRITRMAAFLALQQNPPLPIWSLDKANVLASSRLW
RKTVEETIKTEFPQLTVQHQLIDSAAMILVKSPTKLNGVVITNNMFGDII
SDEASVIPGSLGLLPSASLASLPDTNKAFGLYEPCHGSAPDLPANKVNPI
ATILSAAMMLKLSLDLVEEGRALEEAVRNVLDAGVRTGDLGGSNSTTEVG
DAIAKAVKEILA
```

SEQ ID No 49 (=nucleic acid His 5)
```
ATGGGTAGGAGGGCTTTTGTAGAAAGAAATACGAACGAAACGAAAATCAG
CGTTGCCATCGCTTTGGACAAAGCTCCCTTACCTGAAGAGTCGAATTTTA
TTGATGAACTTATAACTTCCAAGCATGCAAACCAAAAGGGTGAACAAGTA
ATCCAAGTAGACACGGGAATTGGATTCTTGGATCACATGTATCATGCACT
GGCTAAACATGCAGGCTGGAGCTTACGACTTTACTCAAGAGGTGATTTAA
TCATCGATGATCATCACACTGCAGAAGATACTGCTATTGCACTTGGTATT
GCATTCAAGCAGGCTATGGGTAACTTTGCCGGCGTTAAAAGATTTGGACA
TGCTTATTGTCCACTTGACGAAGCTCTTTCTAGAAGCGTAGTTGACTTGT
CGGGACGGCCCTATGCTGTTATCGATTTGGGATTAAAGCGTGAAAAGGTT
GGGGAATTGTCCTGTGAAATGATCCCTCACTTACTATATTCCTTTTCGGT
AGCAGCTGGAATTACTTTGCATGTTACCTGCTTATATGGTAGTAATGACC
ATCATCGTGCTGAAAGCGCTTTTAAATCTCTGGCTGTTGCCATGCGCGCG
GCTACTAGTCTTACTGGAAGTTCTGAAGTCCCAAGCACGAAGGGAGTGTT
GTAA
```

SEQ ID No 50 (=amino acid His 5)
```
MGRRAFVERNTNETKISVAIALDKAPLPEESNFIDELITSKHANQKGEQV
IQVDTGIGFLDHMYHALAKHAGWSLRLYSRGDLIIDDHHTAEDTAIALGI
AFKQAMGNFAGVKRFGHAYCPLDEALSRSVVDLSGRPYAVIDLGLKREKV
GELSCEMIPHLLYSFSVAAGITLHVTCLYGSNDHHRAESAFKSLAVAMRA
ATSLTGSSEVPSTKGVL
```

SEQ ID No 51 (=nucleic acid Trp1 k1)
```
ATGCTCGTTAAAGTGTGTGGTTTGCAAACCGTTGAAGCTGCAAAGACTGC
TGTGGATGATGGTGCTGATTACTTAGGTATCATTTGTGTTCCCGGTAGGA
AAAGAACCATTGACTCATCTGTTGCGAAAGGTATTTCAACTGCAGTTCAC
CAACAAGAGAACGTGAAAGGTACTAAACTAGTCGGGGTGTTTAGAAATCA
GTCCGTTGATGATGTCCTTCAACTGTACCACGAATATAATCTAGATGTGA
TACAATTACATGGAGATGAAGATATTAAAGAATACAGATCTTTGATCCCA
TCTTCAATTCCAATCATTAAGAGGTTCCAGTTCCCACAGGATTGTGAATT
ACTACTGGACCTGTATGAACACGTAGACAATGTGCTGACGTTGTTCGATT
CTGGTGAAGGTGGCACTGGTGAGAATTGAATTGGAGTGCAATTTCCAGT
TGGTCTGCAAGTCATCCCGAGATAAAATTCATTATCGCTGGTGGATTGAA
TCCTGATAACGTTTCTGTTGCCATTAATATGTTACCAAATGCGATCGGTG
TCGATGTAAGTGGAGGAGTAGAGACTGATGGTATCAAGGATTTAGAAAAG
GTAAAGCTATTCATCCAGCAGGCCTCTCAATAG
```

SEQ ID No 52 (=amino acid Trp1 K1)
```
MLVKVCGLQTVEAAKTAVDDGADYLGIICVPGRKRTIDSSVAKGISTAVH
QQENVKGTKLVGVFRNQSVDDVLQLYHEYNLDVIQLHGDEDIKEYRSLIP
SSIPIIKRFQFPQDCELLLDLYEHVDNVLTLFDSGEGGTGEKLNWSAISS
WSASHPEIKFIIAGGLNPDNVSVAINMLPNAIGVDVSGGVETDGIKDLEK
VKLFIQQASQ
```

---

The invention claimed is:

1. A recombinant yeast having a reduced pyruvate decarboxylase activity, in the genome of which has been inserted:
   one or more nucleic acids encoding an acetolactate synthase or ALS,
   one or more nucleic acids encoding an acetolactate decarboxylase or ALD, and
   one or more copies of a nucleic acids encoding a NADH oxidase or NOXE.

2. The recombinant yeast according to claim 1, wherein the said recombinant yeast comprises one or more DNA constructs selected from a group comprising the following formulae:
   (I) A DNA construct comprising:
      a first DNA subconstruct comprising [Gene 1]$_{x1}$ and
      a second DNA subconstruct comprising [Gene 2]$_{x2}$ and
      a third DNA subconstruct comprising [Gene 3]$_{x3}$,
   (II) a DNA construct comprising:
      a first DNA subconstruct comprising [Gene 1]$_{x1}$-[Gene 2]$_{x2}$ and
      a second DNA subconstruct comprising [Gene 3]$_{x3}$,
   (IIa) a DNA construct comprising:
      a first DNA subconstruct comprising [prom5$_{y1}$-Gene 1-term5]$_{x5}$-[prom1-Gene 1-term1]$_{x1}$-[prom2-Gene 2-term2$_{z1}$]$_{x2}$ and
      a second DNA subconstruct comprising [prom3$_{y2}$-Gene 3-term3]$_{x3}$, and
   (IIb) a DNA construct comprising:
      a first DNA subconstruct comprising [prom5$_{y1}$-ALS-term5]$_{x5}$-[prom1-ALS-term1]$_{x1}$-[prom2-ALD-term2$_{z1}$]$_{x2}$ and
      a second DNA subconstruct comprising [prom3$_{y2}$-NOXE-term3$_{z2}$]$_{x3}$ and (III) a DNA subconstruct comprising [Gene 1]$_{x1}$-[Gene 2]$_{x2}$-[Gene 3]$_{x3}$, wherein:
   "Gene I" is a nucleic acid selected from a group comprising ALS, ALD, or NOXE;
   "Gene 2" is a nucleic acid selected from a group comprising ALS, ALD, or NOXE but different from gene 1;
   "Gene 3" is a nucleic acid selected from a group comprising ALS, ALD, or NOXE but different from genes I and 2; and wherein
   each of "x1", "x2" and "x3", represents an integer ranging from 1 to 50,
   "x5" represents an integer equal to 0 or I;
   "y1", "y2", "z1" and "z2" represent an integer equal to 0 or 1;
   "prom1" is a regulatory sequence which controls the expression of the sequence encoding the Gene 1;
   "prom2" is a regulatory sequence which controls the expression of the sequence encoding the Gene 2;
   "prom3" is a regulatory sequence which controls the expression of the sequence encoding the Gene 3;
   "prom5" is a regulatory sequence which controls the expression of Gene 1, said proms being identical or different from prom1;
   "termI" is a transcription terminator sequence that ends expression of the sequence encoding the Gene I;
   "term2" is a transcription terminator sequence that ends expression of the sequence encoding the Gene 2;
   "term3" is a transcription terminator sequence that ends expression of the sequence encoding the Gene 3;
   "term5" is a transcription terminator sequence that ends expression of Gene 1, said term5 being identical or different from term1.

3. The recombinant yeast according to claim 2, wherein the said recombinant yeast comprises at least one DNA construct of formula (II), wherein Gene 3 is a nucleic acid encoding NADH oxidase.

4. The recombinant yeast according to claim 2, wherein the said recombinant yeast comprises at least one DNA construct(s) of formula (IIa).

5. The recombinant yeast according to claim 2, wherein said recombinant yeast comprises at least one DNA construct(s) of formula (IIb).

6. The recombinant yeast according claim 2, wherein the recombinant yeast comprises at least two DNA constructs of formula (II), (IIa) or (IIb).

7. The recombinant yeast according to claim 2, wherein the said recombinant yeast comprises at least one DNA construct having formulae (IIb), and at least one DNA construct having formulae (IIb) wherein the second DNA subconstruct is absent.

8. The recombinant yeast according claim 2, wherein the DNA construct(s) selected from the group comprising formulae (I) to (IIb) comprising at least the NOXE gene(s) is/are inserted in the endogenous URA3 gene of said recombinant yeast.

9. The recombinant yeast claim 1, wherein the nucleic acid(s) encoding the acetolactate synthase or ALS is/are nucleic acid(s) selected from the group consisting of sequences having at least 65% nucleic acid identity with the nucleic acid sequences SEQ ID NO: 1, 3, and 5.

10. The recombinant yeast according to claim 1, wherein the nucleic acid(s) encoding the acetolactate decarboxylase or ALD is/are nucleic acid(s) selected from the group consisting of sequences having at least 36% nucleic acid identity with the nucleic acid sequences SEQ ID NO: 7, 9, and 11.

11. The recombinant yeast according to claim 1, wherein the nucleic acid(s) encoding the NADH oxidase or NOXE is/are nucleic acid(s) selected from the group consisting of sequences having at least 78% nucleic acid identity with the nucleic acid sequences SEQ ID NO: 21, 23, 25, and 27.

12. The recombinant yeast according to claim 1, wherein each of nucleic acids encoding acetolactate synthase, acetolactate decarboxylase, and NADH oxidase is under the control of a promoter, identical or different, said promoters being characterized by a sequence of nucleic acids selected from the group consisting of sequences having at least 80% nucleic acid identity with the nucleic acid sequences SEQ ID NO: 29 to 39, 49, and 50.

13. The recombinant yeast according to claim 1, wherein each of nucleic acids encoding acetolactate synthase, acetolactate decarboxylase, and NADH oxidase is under the control of a transcription terminator, identical or different, said transcription terminators being characterized by a sequence of nucleic acid selected from the group consisting of sequences having at least 80% nucleic acid identity with the nucleic acid sequence of SEQ ID NO: 40 to 48.

14. The recombinant yeast according to claim 1, wherein the pyruvate decarboxylase activity is reduced by disruption of at least one pdc gene.

15. The recombinant yeast according to claim 14, wherein the pyruvate decarboxylase activity is reduced by insertion of at least one DNA construct(s) selected from the group comprising formulae (I) to (III).

16. The recombinant yeast according to claim 1, wherein when the recombinant yeast belongs to the *Sacharomyces* genus, then the pyruvate decarboxylase activity is reduced by disruption of at least two pdc genes.

17. A method for producing acetoin, said method comprising the steps of:
   (a) culturing a recombinant yeast such as defined claim 1 in an appropriate culture medium; and
   (b) recovering the acetoin.

18. The method according to the precedent claim 17, wherein the said culture medium comprises a carbon source.

* * * * *